US012667688B2

(12) United States Patent
Wong et al.

(10) Patent No.: US 12,667,688 B2
(45) Date of Patent: Jun. 30, 2026

(54) HEAT AND MOISTURE EXCHANGER FOR PATIENT INTERFACE

(71) Applicant: RESMED PTY LTD, Bella Vista (AU)

(72) Inventors: Kevin Kai Yun Wong, Sydney (AU); James McKensey Bencke, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 841 days.

(21) Appl. No.: 17/614,895

(22) PCT Filed: May 29, 2020

(86) PCT No.: PCT/IB2020/055114
§ 371 (c)(1),
(2) Date: Nov. 29, 2021

(87) PCT Pub. No.: WO2020/240495
PCT Pub. Date: Dec. 3, 2020

(65) Prior Publication Data
US 2022/0233803 A1     Jul. 28, 2022

Related U.S. Application Data

(60) Provisional application No. 62/855,109, filed on May 31, 2019.

(51) Int. Cl.
*A61M 16/10*     (2006.01)
*A61M 16/00*     (2006.01)
(Continued)

(52) U.S. Cl.
CPC .... *A61M 16/1045* (2013.01); *A61M 16/0808* (2013.01); *A61M 16/0816* (2013.01);
(Continued)

(58) Field of Classification Search
CPC .......... A61M 16/1045; A61M 16/0808; A61M 16/0816; A61M 16/0875; A61M 2205/02;
(Continued)

(56) References Cited

U.S. PATENT DOCUMENTS

| | | |
|---|---|---|
| 1,679,839 A | 8/1928 | Mitchell |
| 2,435,721 A | 2/1948 | Lehman |

(Continued)

FOREIGN PATENT DOCUMENTS

| | | |
|---|---|---|
| WO | WO 98/004310 A1 | 2/1998 |
| WO | WO 98/034665 A1 | 8/1998 |

(Continued)

OTHER PUBLICATIONS

"*Respiratory Physiology*", by John B. West, Lippincott Williams & Wilkins, 9th edition published 2012 (8 pages).
(Continued)

*Primary Examiner* — Rachel T Sippel
*Assistant Examiner* — Gwynneth L Howell
(74) *Attorney, Agent, or Firm* — NIXON & VANDERHYE, PC

(57) ABSTRACT

A patient interface may include: a plenum chamber pressurisable to a therapeutic pressure; a seal-forming structure connected to the plenum chamber, the plenum chamber being constructed and arranged to seal with a region of the patients face; a positioning and stabilising structure configured to provide a force to hold the seal-forming structure in a therapeutically effective position on the patients head; a vent structure configured to allow a continuous flow of gases exhaled by the patient from an interior of the plenum chamber to ambient; and a material configured to adsorb water vapour from gases exhaled by the patient and desorb water vapour into the flow of air at the therapeutic pressure, the material being positioned within the plenum chamber.

21 Claims, 50 Drawing Sheets

(51) Int. Cl.
| | |
|---|---|
| *A61M 16/06* | (2006.01) |
| *A61M 16/08* | (2006.01) |
| *A61M 16/20* | (2006.01) |

(52) U.S. Cl.
CPC .............. *A61M 2016/0027* (2013.01); *A61M 2016/003* (2013.01); *A61M 16/0066* (2013.01); *A61M 16/06* (2013.01); *A61M 16/0875* (2013.01); *A61M 16/208* (2013.01)

(58) Field of Classification Search
CPC ........... A61M 2210/0618; A61M 16/06–0694; A62B 7/00–14; A62B 9/00–003; A62B 18/00; A62B 18/006–025; A62B 18/084
See application file for complete search history.

(56) References Cited

U.S. PATENT DOCUMENTS

| | | | |
|---|---|---|---|
| 2,845,927 A | 8/1958 | Hill | |
| 4,200,094 A | 4/1980 | Gedeon et al. | |
| 4,269,183 A | 5/1981 | Hunt | |
| 4,782,832 A | 11/1988 | Trimble et al. | |
| 4,944,310 A | 7/1990 | Sullivan | |
| 5,687,715 A | 11/1997 | Landis | |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,485,189 B2 | 7/2013 | Wallnewitz et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,844,533 B2 | 9/2014 | Allum et al. | |
| 9,038,634 B2 | 5/2015 | Brambilla et al. | |
| 2008/0060649 A1* | 3/2008 | Veliss ................... | A61M 16/06 128/207.18 |
| 2009/0032026 A1* | 2/2009 | Price ..................... | A61M 16/06 128/207.11 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2011/0108036 A1 | 5/2011 | Loescher | |
| 2011/0253147 A1 | 10/2011 | Gusky et al. | |
| 2012/0285448 A1* | 11/2012 | Dugan .............. | A61M 16/0605 128/202.16 |
| 2012/0325218 A1* | 12/2012 | Brambilla ......... | A61M 16/0833 128/205.25 |
| 2012/0330183 A1* | 12/2012 | Allum .................. | A61B 5/4836 128/205.24 |
| 2013/0190643 A1 | 7/2013 | Brambilla | |

| | | | |
|---|---|---|---|
| 2014/0182583 A1 | 7/2014 | Wondka et al. | |
| 2014/0276177 A1 | 9/2014 | Brambilla et al. | |
| 2015/0335846 A1 | 11/2015 | Romagnoli et al. | |
| 2016/0095996 A1 | 4/2016 | Gusky et al. | |
| 2016/0175552 A1 | 6/2016 | Harrington | |
| 2016/0193438 A1* | 7/2016 | White ................. | A61M 16/026 128/204.23 |
| 2016/0250438 A1* | 9/2016 | Harwood .......... | A61M 16/0875 128/201.13 |
| 2017/0035978 A1 | 2/2017 | Holley et al. | |
| 2017/0281898 A1* | 10/2017 | Dantanarayana ........................... | A61M 16/0825 |
| 2018/0133426 A1 | 5/2018 | Hallett et al. | |
| 2018/0200467 A1 | 7/2018 | Finch | |
| 2019/0151592 A1* | 5/2019 | Bornholdt ......... | A61M 16/0683 |

FOREIGN PATENT DOCUMENTS

| | | | |
|---|---|---|---|
| WO | WO 2000/078381 A1 | 12/2000 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/070495 A1 | 6/2010 | |
| WO | WO 2010/135785 A1 | 12/2010 | |
| WO | WO 2012/171072 A1 | 12/2012 | |
| WO | WO 2013/020167 A1 | 2/2013 | |
| WO | WO 2013/067592 A1 | 5/2013 | |
| WO | WO 2014/138820 A1 | 9/2014 | |
| WO | WO 2015/052681 A1 | 4/2015 | |
| WO | WO 2015/161345 A1 | 10/2015 | |
| WO | WO 2018/053589 A1 | 3/2018 | |
| WO | WO 2018/126295 A1 | 7/2018 | |
| WO | WO 2018/176094 A1 | 10/2018 | |
| WO | WO 2020/037359 A1 | 2/2020 | |
| WO | WO 2020/188495 A1 | 9/2020 | |

OTHER PUBLICATIONS

International Search Report mailed Jul. 28, 2020 issued in PCT/IB2020/055114 (7 pages).
Written Opinion of the International Search Authority mailed Jul. 28, 2020 issued in PCT/IB2020/055114 (9 pages).
Written Opinion of the International Search Authority mailed May 10, 2021 issued in PCT/IB2020/055114 (5 pages).
International Preliminary Report on Patentability mailed Sep. 14, 2021 issued in PCT/IB2020/055114 (24 pages).
Extended European Search Report dated Jul. 1, 2022 issued in European Application No. 20812570.8 (9 pages).

* cited by examiner

Nasal cavity

Oral cavity

Larynx

Vocal folds

Oesophagus

Trachea

Bronchus

Lung

Heart

Diaphragm

Alveolar sacs

Superior

Posterior ↔ Anterior

Inferior

Otobasion superior

Otobasion inferior

Alar crest point

Glabella

Sellion

Ridge

Pronasale

Subnasale

Lip superior

Lip Inferior

Supramenton

Copyright 2012 ResMed Limited

Frontal sinus

Nasal bone

Septum cartilage

Medial crus of greater alar cartilage

Anterior nasal spine

Frontal process of maxilla

Lesser alar cartilage

Fibrofatty tissue

Epidermis

Adipose tissue

Nasal bone

Lateral cartilage

Septum cartilage

Greater alar cartilage

Frontal bone

Supraorbital
foramen

Nasal bones

Septal cartilage

Lateral cartilage

Sesamoid
cartilage

Greater alar
cartilage

Medial crus
of greater alar
cartilage

Anterior nasal spine

Infraorbital
foramen

Lesser nasal
cartilage

Alar fibrofatty
tissue

Septal cartilage

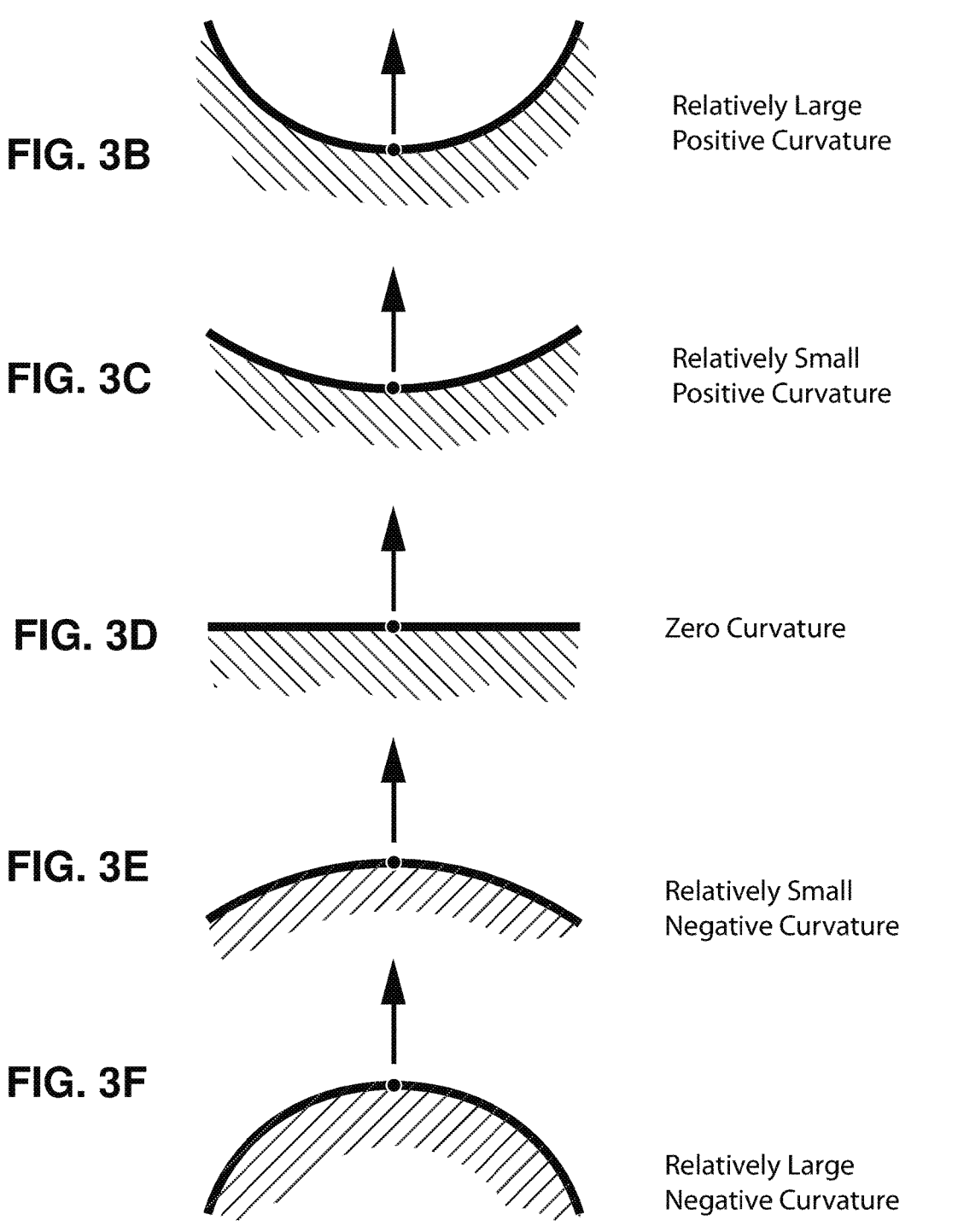
FIG. 3B                                          Relatively Large
                                                 Positive Curvature
FIG. 3C                                          Relatively Small
                                                 Positive Curvature
FIG. 3D                                          Zero Curvature
FIG. 3E                                          Relatively Small
                                                 Negative Curvature
FIG. 3F                                          Relatively Large
                                                 Negative Curvature

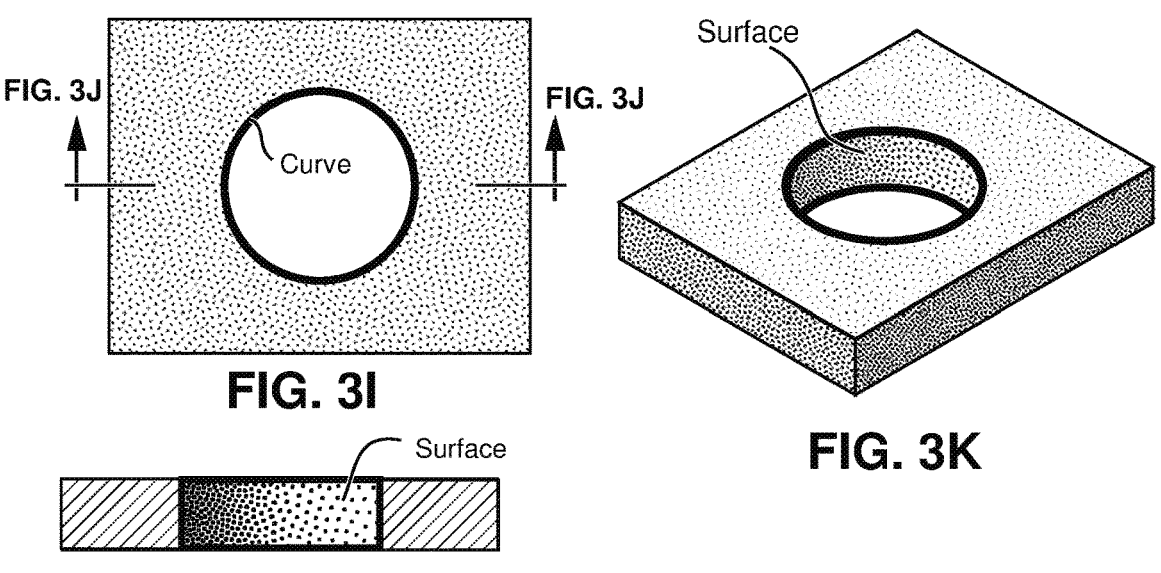
FIG. 3J
Curve
FIG. 3J
FIG. 3I
Surface
FIG. 3K
Surface
FIG. 3J
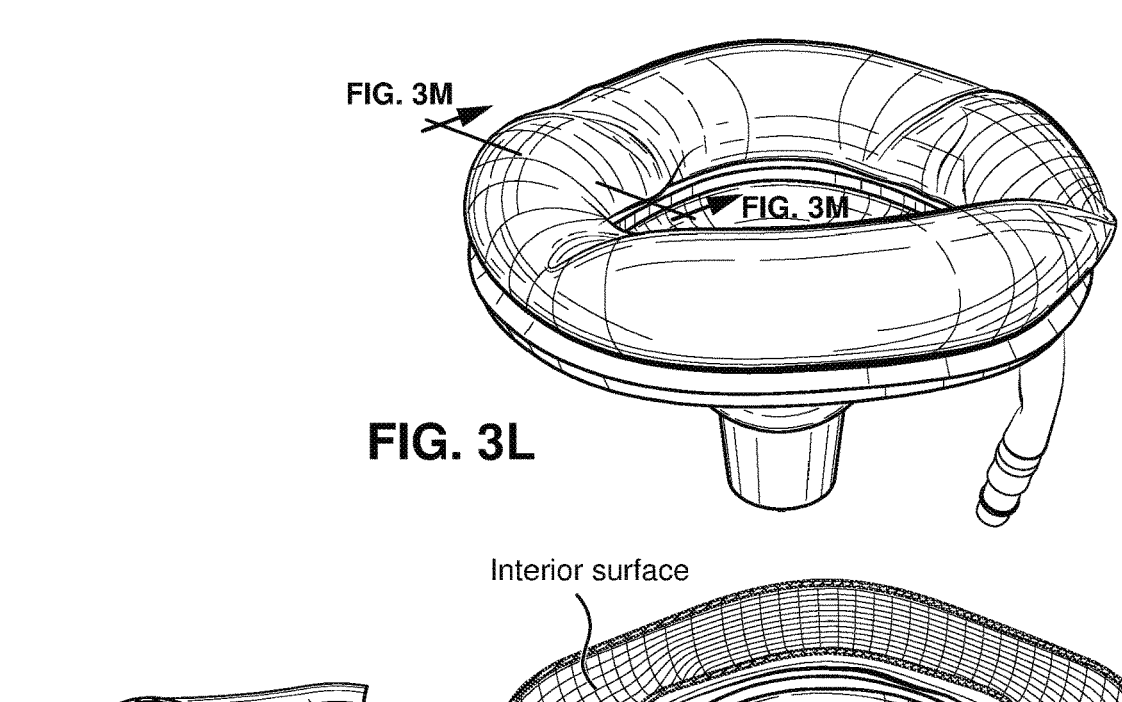
FIG. 3M
FIG. 3M
FIG. 3L
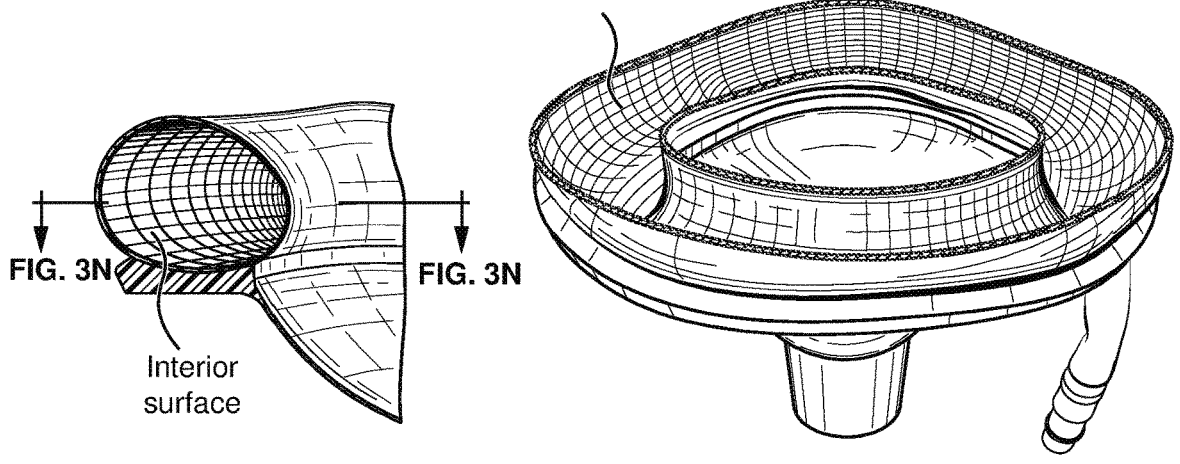
Interior surface
FIG. 3N
FIG. 3N
Interior surface
FIG. 3M          FIG. 3N

Left-hand rule
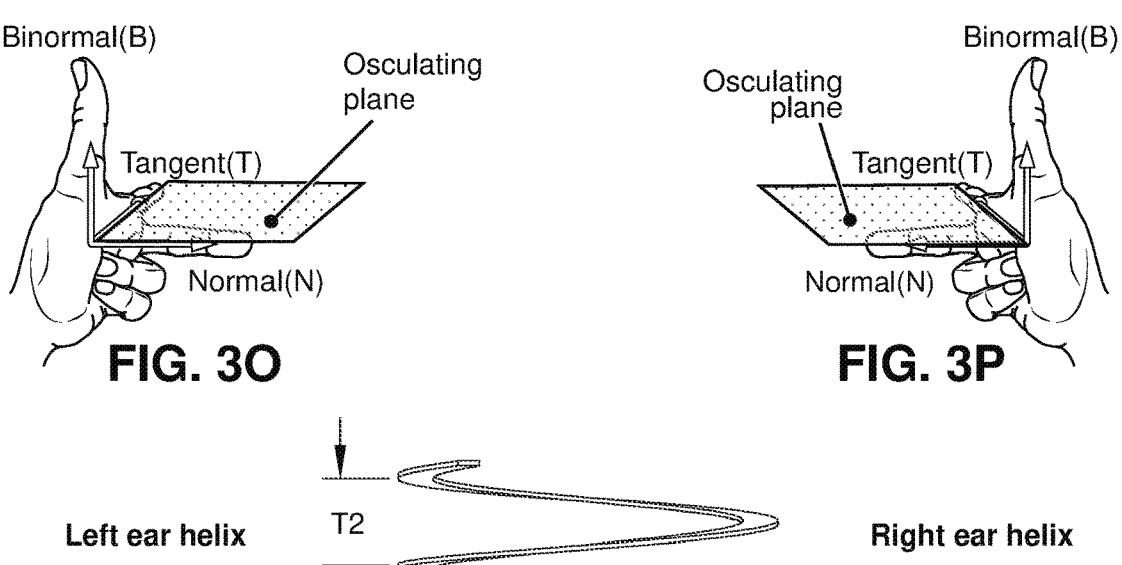
Binormal(B)
Osculating plane
Tangent(T)
Normal(N)
FIG. 3O
Right-hand rule
Binormal(B)
Osculating plane
Tangent(T)
Normal(N)
FIG. 3P
Left ear helix
FIG. 3Q
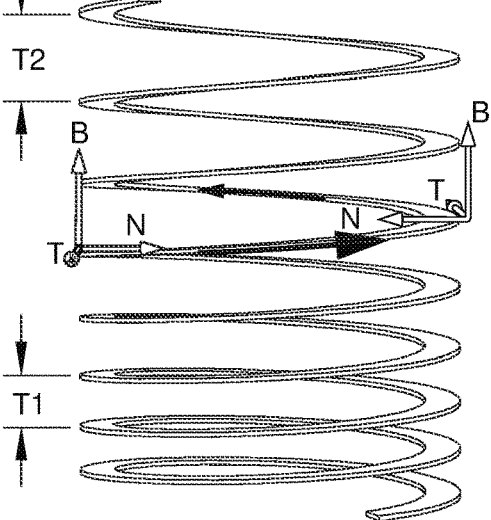
T2
B
N
N
T
T1
B
T
Right ear helix
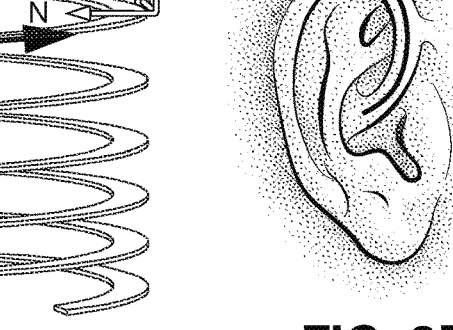
FIG. 3R
Right-hand helix
Right-hand positive
FIG. 3S
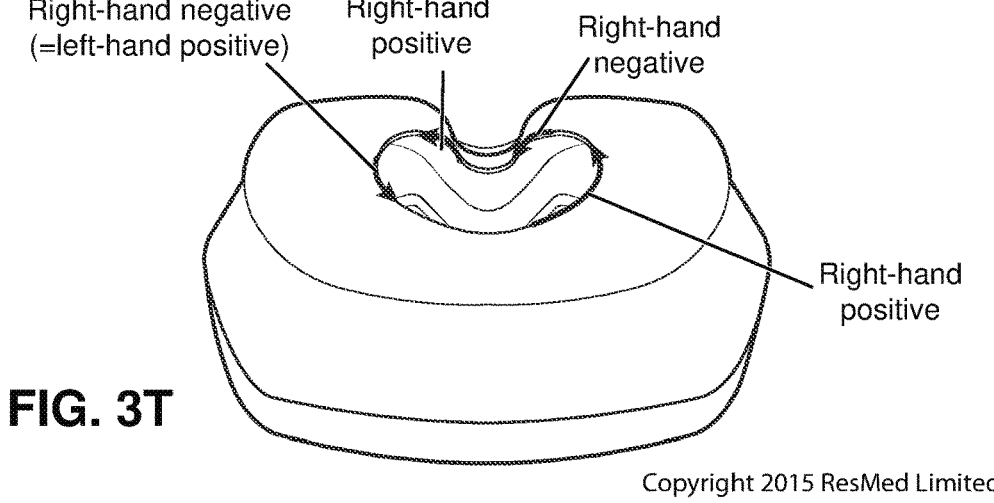
Right-hand negative
(=left-hand positive)
Right-hand positive
Right-hand negative
Right-hand positive
FIG. 3T 3214    3202    3208    3900    3904    3214

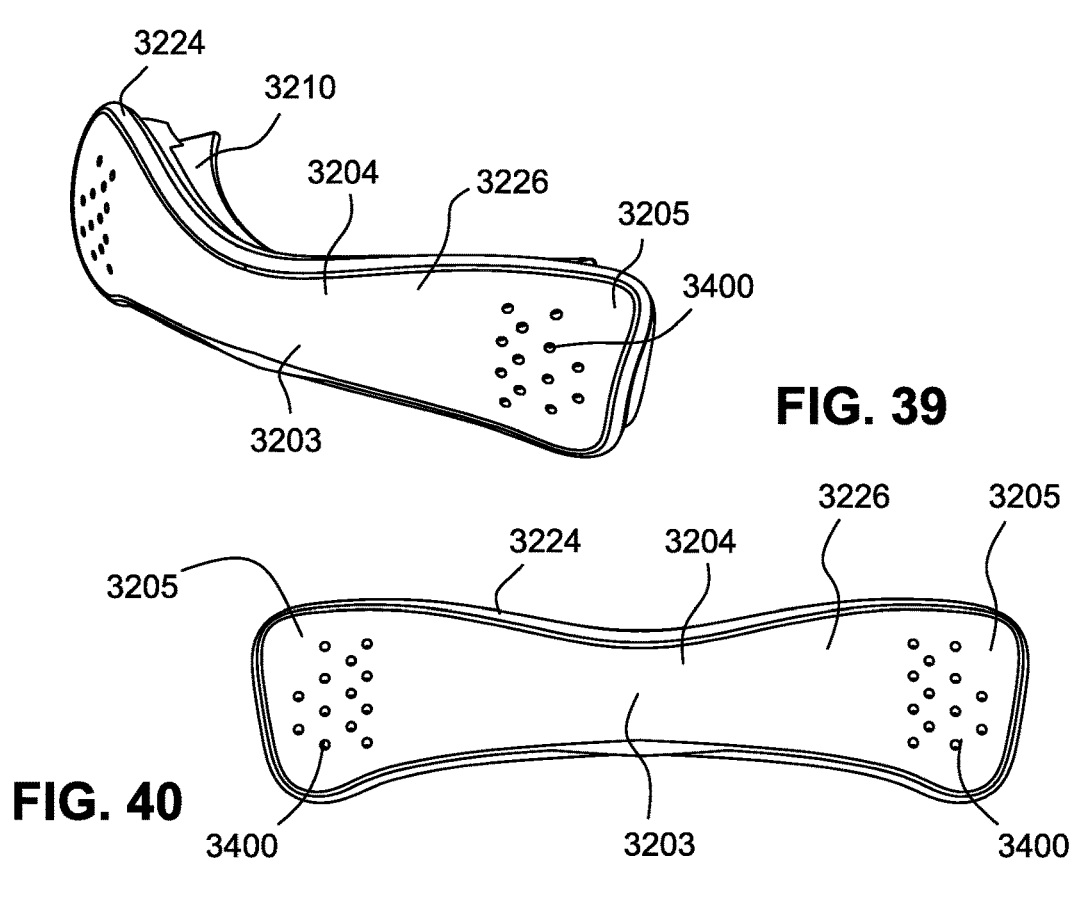
FIG. 39
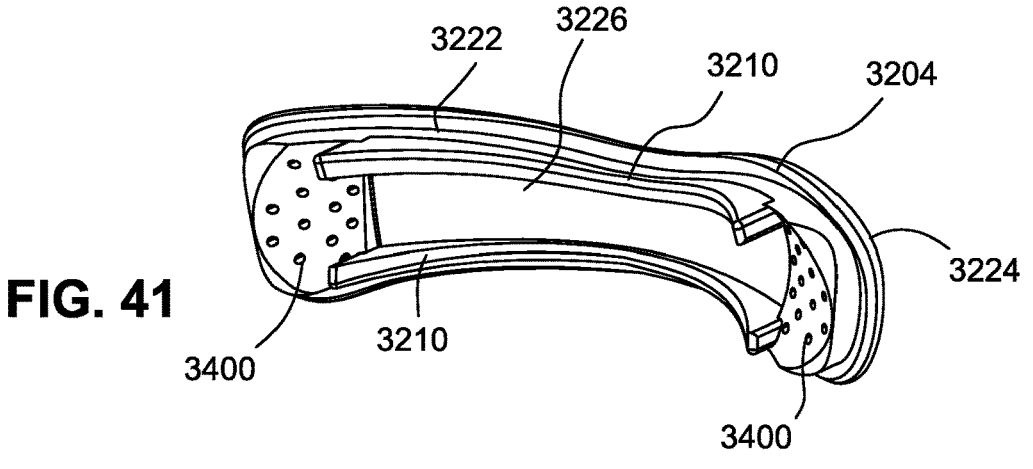
FIG. 40
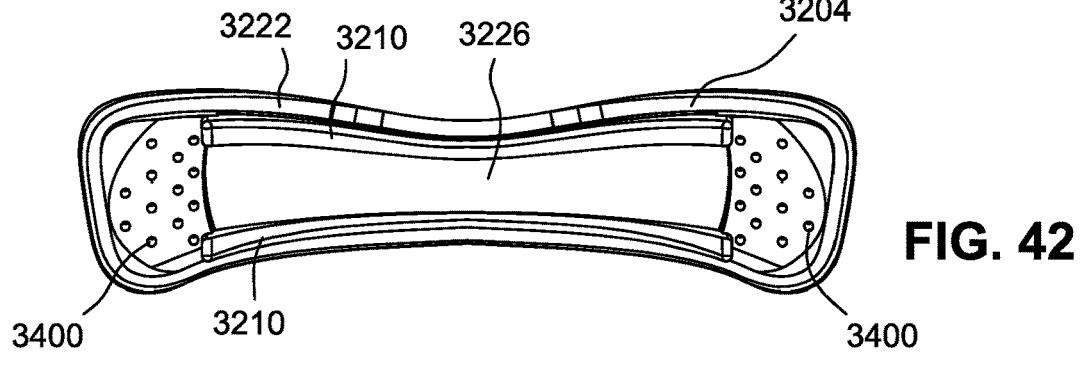
FIG. 41
FIG. 42

HEAT AND MOISTURE EXCHANGER FOR PATIENT INTERFACE

1 CROSS-REFERENCE TO RELATED APPLICATIONS

This application is the U.S. national phase of International Application No. PCT/IB2020/055114 filed May 29, 2020 which designated the U.S. and claims the benefit of U.S. Provisional Application No. 62/855,109, filed May 31, 2019, the entire contents of each of which are incorporated herein by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices
(one specimen only, measured using test method specified
in ISO 3744 in CPAP mode at 10 cmH₂O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |

-continued

Table of noise output levels of prior RPT devices
(one specimen only, measured using test method specified
in ISO 3744 in CPAP mode at 10 cmH₂O).

| RPT Device name | A-weighted sound pressure level dB(A) | Year (approx.) |
|---|---|---|
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical. Recently, companies that manufacture large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses or "boli", each bolus timed to coincide with the start of inspiration. This therapy mode is known as pulsed or demand (oxygen) delivery (POD), in contrast with traditional continuous flow delivery more suited to stationary oxygen concentrators.

2.2.3.6 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.7 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (™ J) side effects. Thus, it is configured to minimises or prevent any movement of one or more of the teeth.

2.2.3.8 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

Table of noise of prior masks (ISO 17510-2:
2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology is directed to a patient interface comprising: a plenum chamber; a seal-forming structure; and a positioning and stabilising structure. A vent structure may also be included.

A patient interface comprising: a plenum chamber pressurisable to a therapeutic pressure of at least 4 cmH$_2$O above ambient air pressure; a seal-forming structure constructed and arranged to seal with a region of the patient's face surrounding an entrance to the patient's airways; a positioning and stabilising structure to provide a force to hold the seal-forming structure in a therapeutically effective position on the patient's head; and a vent structure to allow a continuous flow of gases exhaled by the patient from an interior of the plenum chamber to ambient. The patient interface may also be configured to allow the patient to breath from ambient through their mouth in the absence of a flow of pressurised air through the plenum chamber inlet port, or the patient interface is configured to leave the patient's mouth uncovered.

A patient interface comprising: a plenum chamber pressurisable to a therapeutic pressure of at least 4 cmH$_2$O above ambient air pressure, said plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, said seal-forming structure having a hole therein such that the flow of air at said therapeutic pressure is delivered to at least the patient's nares, the seal-forming structure constructed and arranged to maintain said therapeutic pressure in the plenum chamber throughout the patient's respiratory cycle in use; a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

Another aspect of the present technology is directed to a patient interface comprising: a plenum chamber pressurisable to a therapeutic pressure; a seal-forming structure constructed and arranged to seal with a region of the patient's face; a positioning and stabilising structure configured to provide a force to hold the seal-forming structure in a therapeutically effective position on the patient's head; a vent structure configured to allow a continuous flow of gases exhaled by the patient from an interior of the plenum chamber to ambient; and a material configured to adsorb water vapour from gases exhaled by the patient and desorb water vapour into the flow of air at the therapeutic pressure. Additionally, the patient interface may be configured to leave the patient's mouth uncovered, or if the seal-forming structure is configured to seal around the patient's nose and mouth, the patient interface is configured to allow the patient to breath from ambient in the absence of a flow of pressurised air.

Another aspect of the present technology is directed to a patient interface comprising: a plenum chamber pressurisable to a therapeutic pressure of at least 4 cmH2O above ambient air pressure by a flow of air at the therapeutic pressure for breathing by a patient; a seal-forming structure constructed and arranged to seal with a region of the patient's face at least partly surrounding an entrance to the patient's airways, said seal-forming structure having a hole therein such that the flow of air at said therapeutic pressure is delivered to at least the patient's nares, the seal-forming structure constructed and arranged to maintain said therapeutic pressure in the plenum chamber throughout the patient's respiratory cycle in use; a positioning and stabilising structure configured to provide a force to hold the seal-forming structure in a therapeutically effective position on the patient's head; a vent structure configured to allow a continuous flow of gases exhaled by the patient from an interior of the plenum chamber to ambient, said vent structure being sized and shaped to maintain the therapeutic pressure in the plenum chamber in use; and a material configured to adsorb water vapour from gases exhaled by the patient and desorb water vapour into the flow of air at the therapeutic pressure, the material being positioned in communication with the plenum chamber inlet port; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air.

Another aspect of the present technology is directed to a patient interface comprising: a plenum chamber pressurisable to a therapeutic pressure of at least 4 cmH2O above ambient air pressure by a flow of air at the therapeutic pressure for breathing by a patient, the plenum chamber further comprising two plenum chamber connectors positioned on corresponding lateral sides of the plenum chamber and configured to receive the flow of air at the therapeutic pressure; a seal-forming structure connected to the plenum chamber, the seal-forming structure being constructed and arranged to seal with a region of the patient's face at least partly surrounding an entrance to the patient's airways, said seal-forming structure having a hole therein such that the flow of air at said therapeutic pressure is delivered to at least the patient's nares, the seal-forming structure constructed and arranged to maintain said therapeutic pressure in the plenum chamber throughout the patient's respiratory cycle in use; a positioning and stabilising structure configured to provide a force to hold the seal-forming structure in a therapeutically effective position on the patient's head, the positioning and stabilising structure further comprising two conduits, each of the conduits being configured to be positioned on a corresponding lateral side of the patient's head in use and configured to connect to a corresponding one of the plenum chamber connectors; a vent structure configured to allow a continuous flow of gases exhaled by the patient from an interior of the plenum chamber to ambient, said vent structure being sized and shaped to maintain the therapeutic pressure in the plenum chamber in use; and a material configured to adsorb water vapour from gases exhaled by the patient and desorb water vapour into the flow of air at the therapeutic pressure, the material being positioned within the plenum chamber such that at least a portion of the flow of air at the therapeutic pressure entering the plenum chamber from the plenum chamber connectors passes through the material before entering the patient's airways; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air.

In examples of any one of the aspects described in the preceding paragraphs: (a) the material may comprise foam or paper, (b) the material may comprise a salt applied to a surface of the material, (c) the material may be removable from the plenum chamber, (d) the plenum chamber may comprise a main frame and a removable frame that is removable from the main frame, (e) the material may be attached to the removable frame such that the removable frame and the material are removable from the main frame together, (f) the removable frame may comprise vent holes, (g) the vent holes may include two groups of vent holes, each of the groups of vent holes being positioned proximal to a corresponding lateral side of the removable frame, (h) the main frame may comprise the plenum chamber connectors, each of the plenum chamber connectors being positioned on a corresponding lateral side of the main frame, (i) the main frame may comprise vent holes, (j) the vent holes may include two groups of vent holes, each of the groups of vent holes being positioned proximal to a corresponding lateral side of the main frame, (k) the removable frame may comprise the plenum chamber connectors, each of the plenum chamber connectors being positioned on a corresponding lateral side of the removable frame, (l) two supports may extend from the removable frame, the material being attached to the supports such that the material is spaced from the removable frame and a void is at least partly formed by the removable frame, the material, and the supports, (m) the plenum chamber connectors may be pneumatically connected to the void to provide the flow of air at the therapeutic pressure to the void, (n) the vent holes may be pneumatically connected to the void to allow air in the void to pass through the vent holes to ambient, (o) the material may comprise a posterior surface that faces the patient's face in use, the posterior surface being positively curved to avoid contact with the patient's face during use, (p) the seal-forming structure may be configured to leave the patient's mouth uncovered and the seal-forming structure may comprise nasal pillows or a nasal cradle, (q) the seal-forming structure may be configured to seal around the patient's nose and mouth and the seal-forming structure may comprise a nasal hole or two nasal holes that are configured to pneumatically communicate with the patient's nares in use and a mouth hole that is configured to pneumatically communicate with the patient's mouth in use, (r) the material may be positioned within the plenum chamber so that the flow of air must pass through the material before entering the patient's airways, and/or (s) the material may be positioned within the plenum chamber so that gas exhaled by the patient must pass through the material before exiting to ambient through the vent holes.

Another aspect of the present technology is directed to a patient interface comprising: a plenum chamber pressurisable to a therapeutic pressure; a seal-forming structure connected to the plenum chamber, the seal-forming structure being constructed and arranged to seal with a region of the patient's face; a positioning and stabilising structure configured to provide a force to hold the seal-forming structure in a therapeutically effective position on the patient's head; a vent structure configured to allow a continuous flow of gases exhaled by the patient from an interior of the plenum chamber to ambient; and a material configured to adsorb water vapour from gases exhaled by the patient and desorb water vapour into the flow of air at the therapeutic pressure, the material being attached to the plenum chamber such that the plenum chamber holds the material in a predetermined shape.

Another aspect of the present technology is directed to a patient interface comprising: a plenum chamber pressurisable to a therapeutic pressure of at least 4 cmH2O above ambient air pressure by a flow of air at the therapeutic pressure for breathing by a patient; a seal-forming structure connected to the plenum chamber, the seal-forming structure being constructed and arranged to seal with a region of the patient's face at least partly surrounding an entrance to the patient's airways, said seal-forming structure having a hole therein such that the flow of air at said therapeutic pressure is delivered to at least the patient's nares, the seal-forming structure being constructed and arranged to maintain said therapeutic pressure in the plenum chamber throughout the patient's respiratory cycle in use; a positioning and stabilising structure configured to provide a force to hold the seal-forming structure in a therapeutically effective position on the patient's head; a vent structure configured to allow a continuous flow of gases exhaled by the patient from an interior of the plenum chamber to ambient, said vent structure being sized and shaped to maintain the therapeutic pressure in the plenum chamber in use; and a material configured to adsorb water vapour from gases exhaled by the patient and desorb water vapour into the flow of air at the therapeutic pressure, the material being attached to the plenum chamber such that the plenum chamber holds the material in a predetermined shape, and the material being positioned within the plenum chamber such that at least a portion of the flow of air at the therapeutic pressure entering the plenum chamber passes through the material before entering the patient's airways; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air.

In examples of any one of the aspects described in the preceding paragraphs: (a) the material may comprise foam or paper, (b) the material may comprise a salt applied to a surface of the material, (c) the material may be removable from the plenum chamber, (d) the plenum chamber may comprise a main frame and a removable frame that is removable from the main frame, (e) the material may be attached to the removable frame such that the removable frame and the material are removable from the main frame together, (f) the removable frame may comprise vent holes, (g) the vent holes may include two groups of vent holes, each of the groups of vent holes being positioned proximal to a corresponding lateral side of the removable frame, (h) the main frame may comprise the plenum chamber connectors, each of the plenum chamber connectors being positioned on a corresponding lateral side of the main frame, (i) the main frame may comprise vent holes, (j) the vent holes may include two groups of vent holes, each of the groups of vent holes being positioned proximal to a corresponding lateral side of the main frame, (k) the removable frame may comprise the plenum chamber connectors, each of the plenum chamber connectors being positioned on a corresponding lateral side of the removable frame, (l) two supports may extend from the removable frame, the material being attached to the supports such that the material is spaced from the removable frame and a void is at least partly formed by the removable frame, the material, and the supports, (m) the plenum chamber connectors may be pneumatically connected to the void to provide the flow of air at the therapeutic pressure to the void, (n) the vent holes may be pneumatically connected to the void to allow air in the void to pass through the vent holes to ambient, (o) the material may comprise a posterior surface that faces the patient's face in use, the posterior surface being positively curved to avoid contact with the patient's face during use, (p) the seal-forming structure may be configured to leave the patient's mouth uncovered and the seal-forming structure may comprise nasal pillows or a nasal cradle, (q) the seal-forming structure may be configured to seal around the patient's nose and mouth and the seal-forming structure may comprise a nasal hole or two nasal holes that are configured to pneumatically communicate with the patient's nares in use and a mouth hole that is configured to pneumatically communicate with the patient's mouth in use, (r) the material may be positioned within the plenum chamber so that the flow of air must pass through the material before entering the patient's airways, (s) the material may be positioned within the plenum chamber so that gas exhaled by the patient must pass through the material before exiting to ambient through the vent holes, (t) the plenum chamber may comprise two plenum chamber connectors positioned on corresponding lateral sides of the plenum chamber and configured to receive the flow of air at the therapeutic pressure, (u) the positioning and stabilising structure may comprise two conduits, each of the conduits being configured to be positioned on a corresponding lateral side of the patient's head in use and configured to connect to a corresponding one of the plenum chamber connectors, and/or (v) the material may be positioned within the plenum chamber such that at least a portion of the flow of air at the therapeutic pressure entering the plenum chamber from the plenum chamber connectors passes through the material before entering the patient's airways.

Another aspect of one form of the present technology is a respiratory pressure therapy (RPT) system that may include the patient interface of any one of the preceding aspects; a respiratory pressure therapy (RPT) device configured to generate the flow of air at the therapeutic pressure; and an air circuit configured to connect the RPT device and the patient interface to direct the flow of air at the therapeutic pressure from the RPT device to the patient interface, wherein the RPT system does not include a humidifier.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
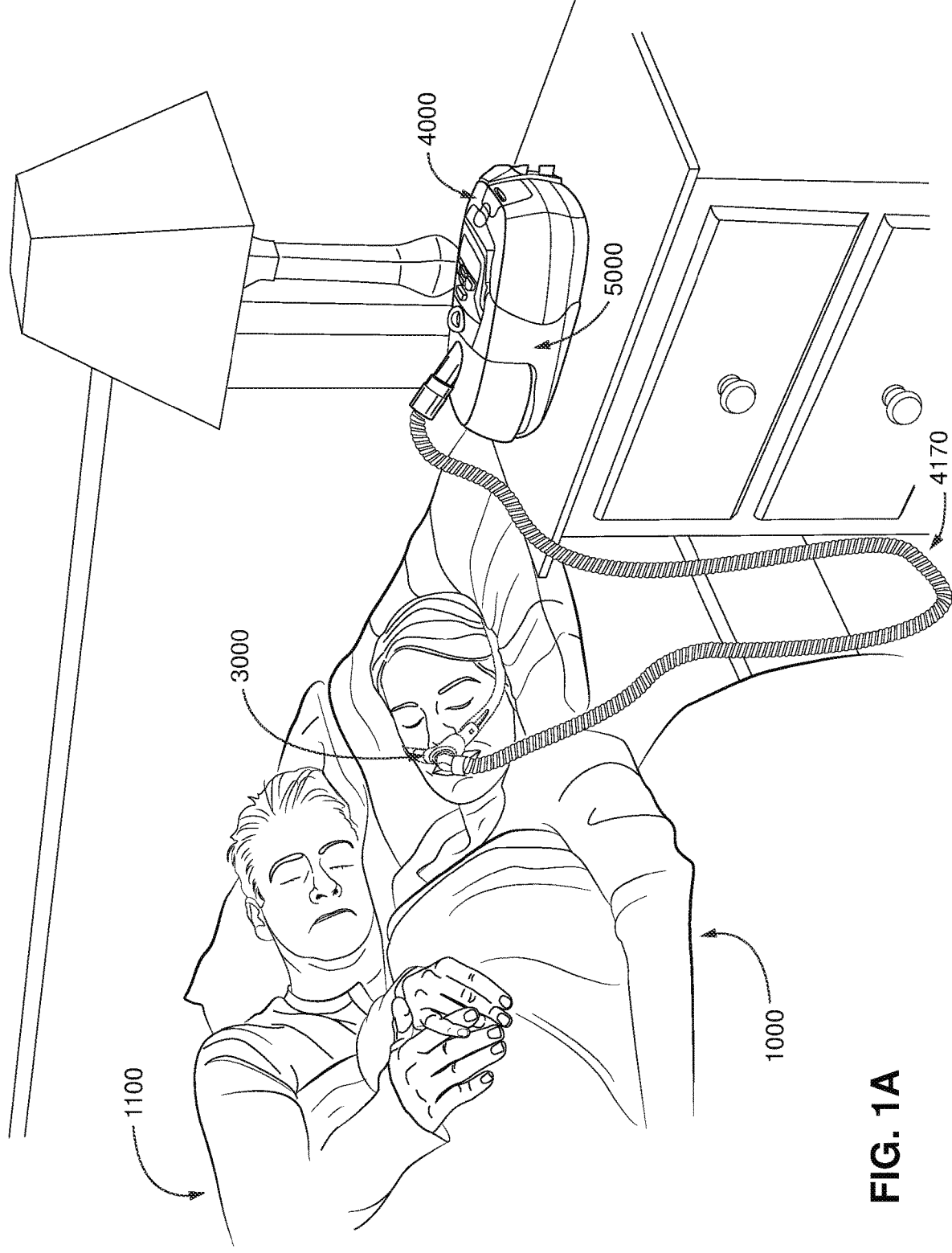
Figure 1B:
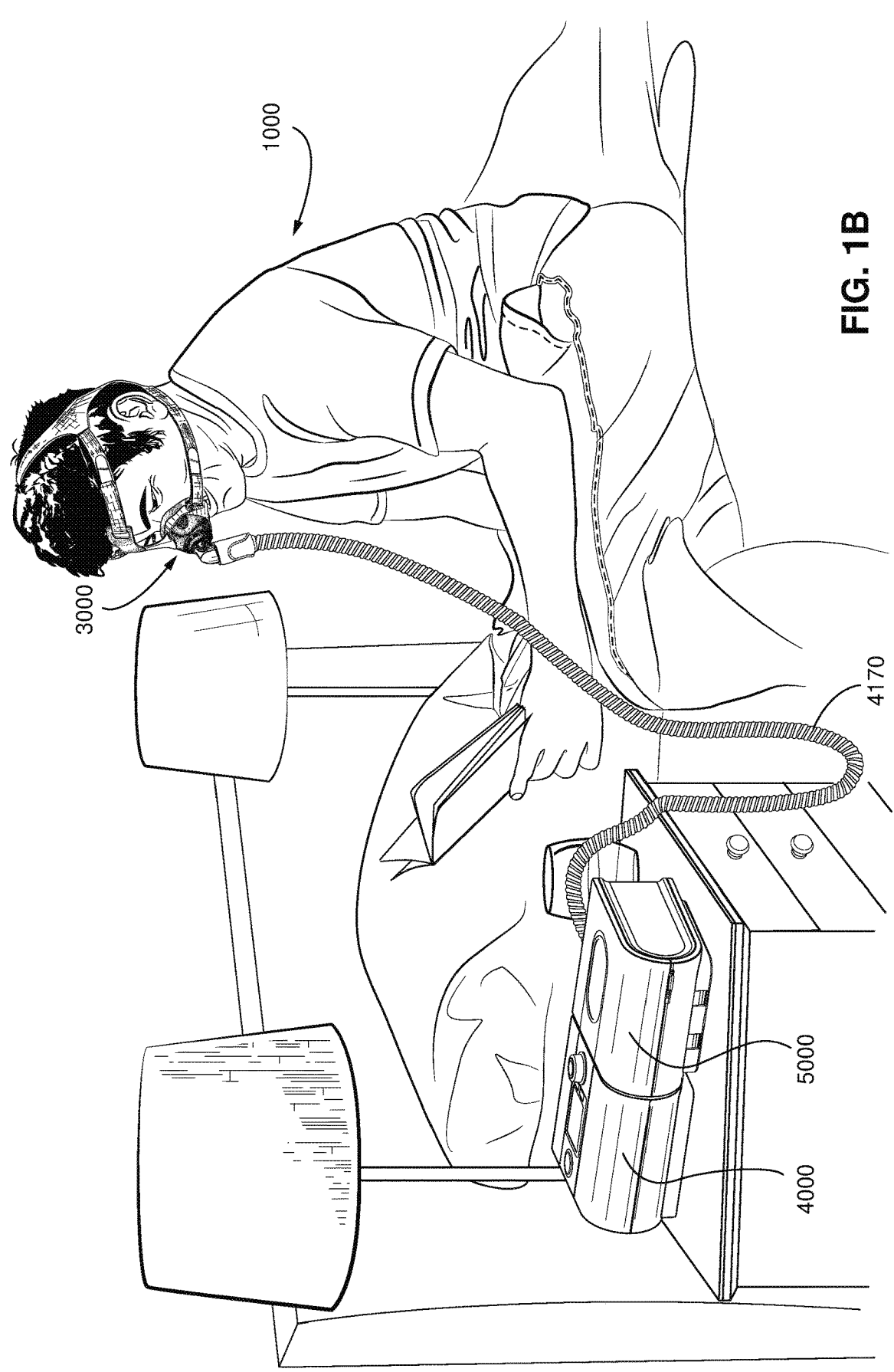
Figure 1C:
Figure 2A:
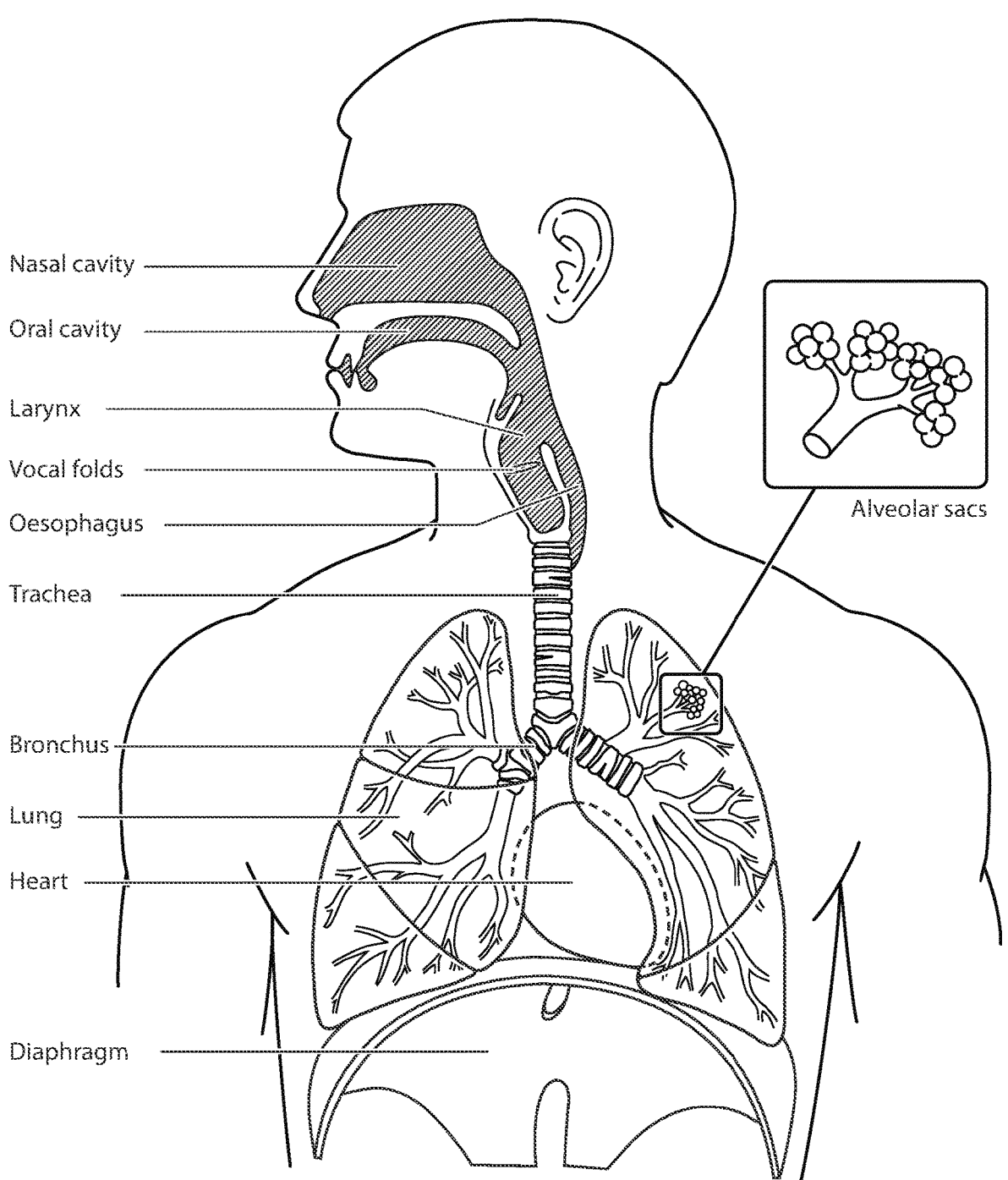
FIG. 2A shows an overview of a human respiratory system including the nasal and oral cavities, the larynx, vocal folds, oesophagus, trachea, bronchus, lung, alveolar sacs, heart and diaphragm.
Figure 2B:
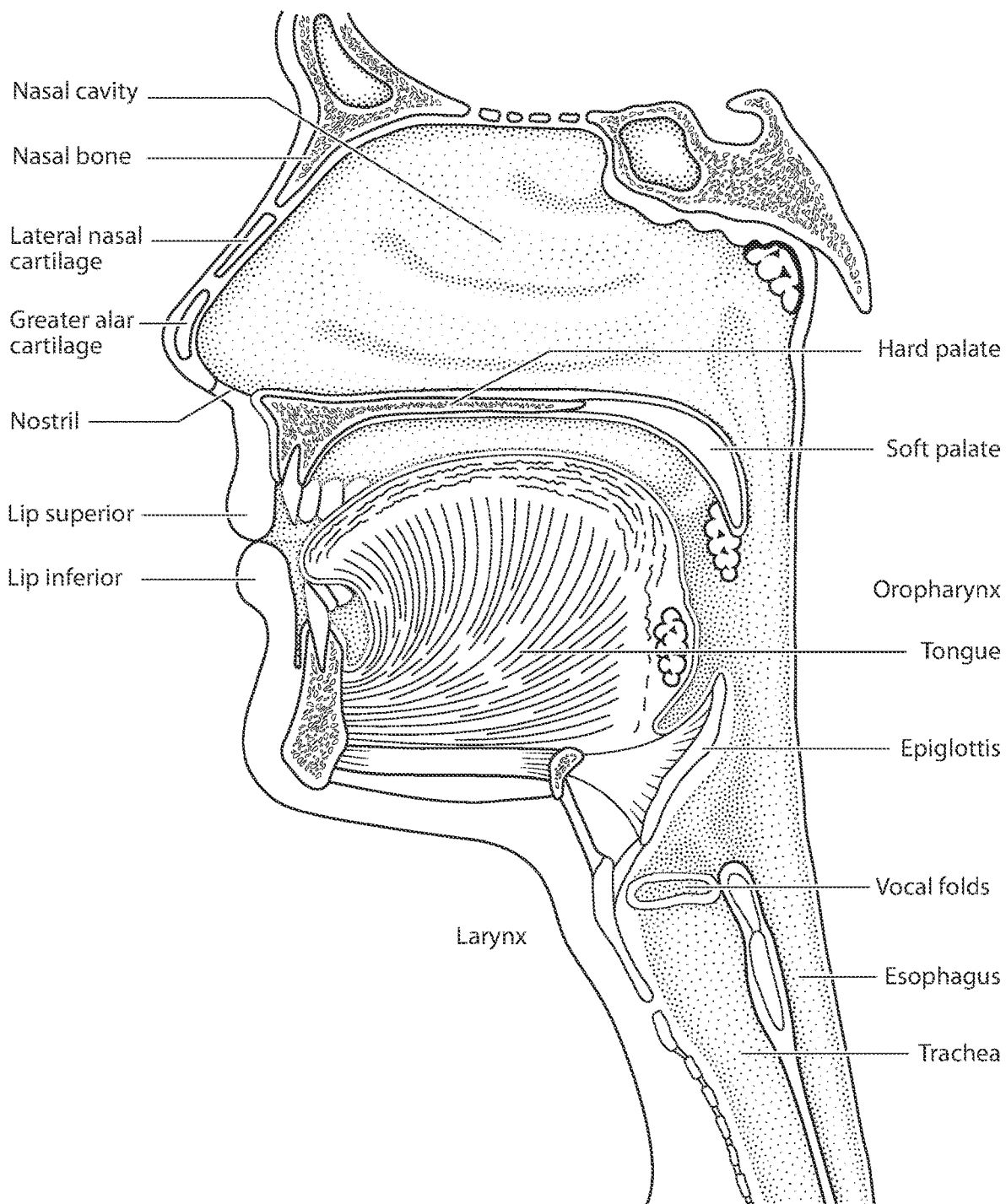
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
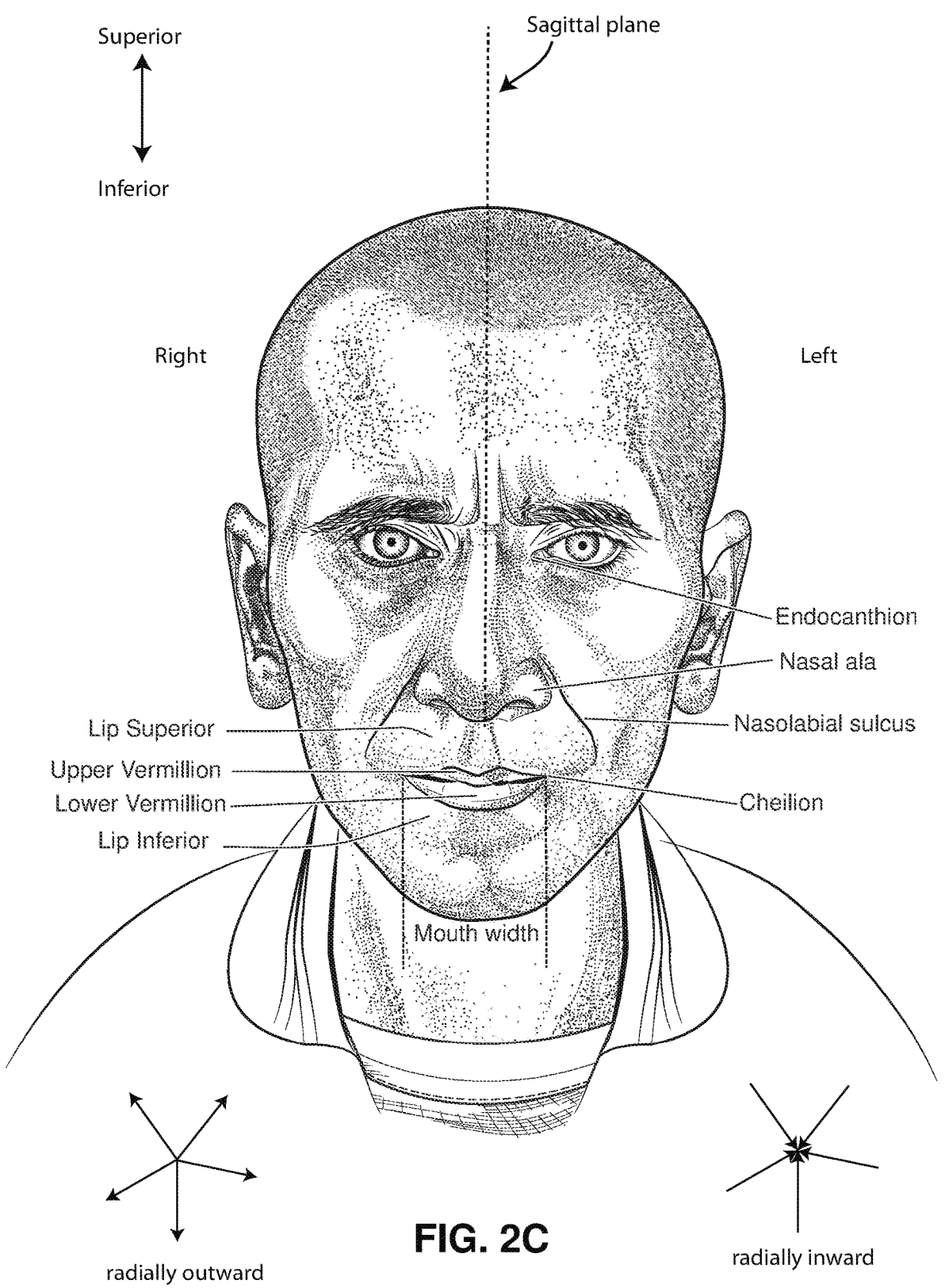
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
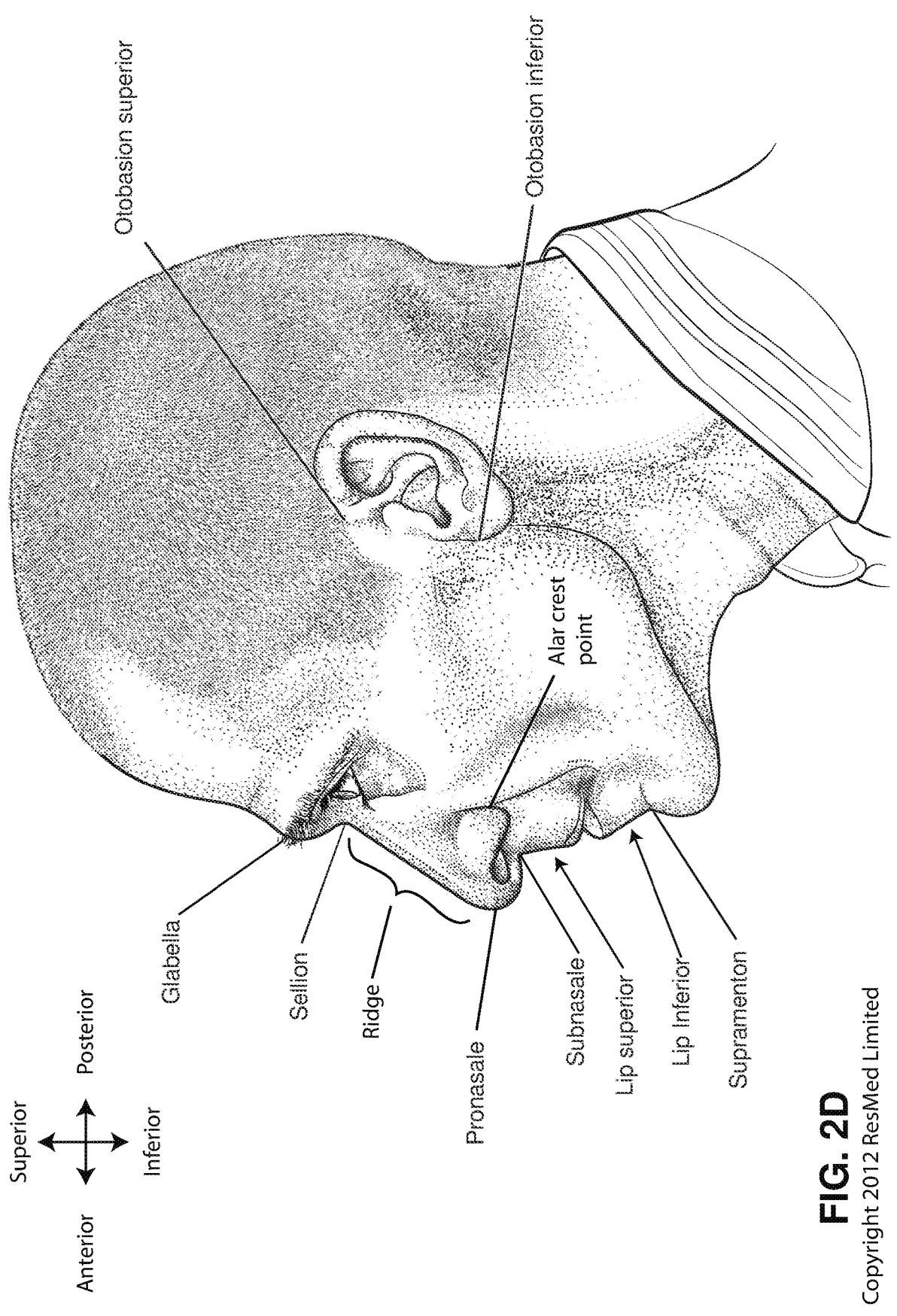
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
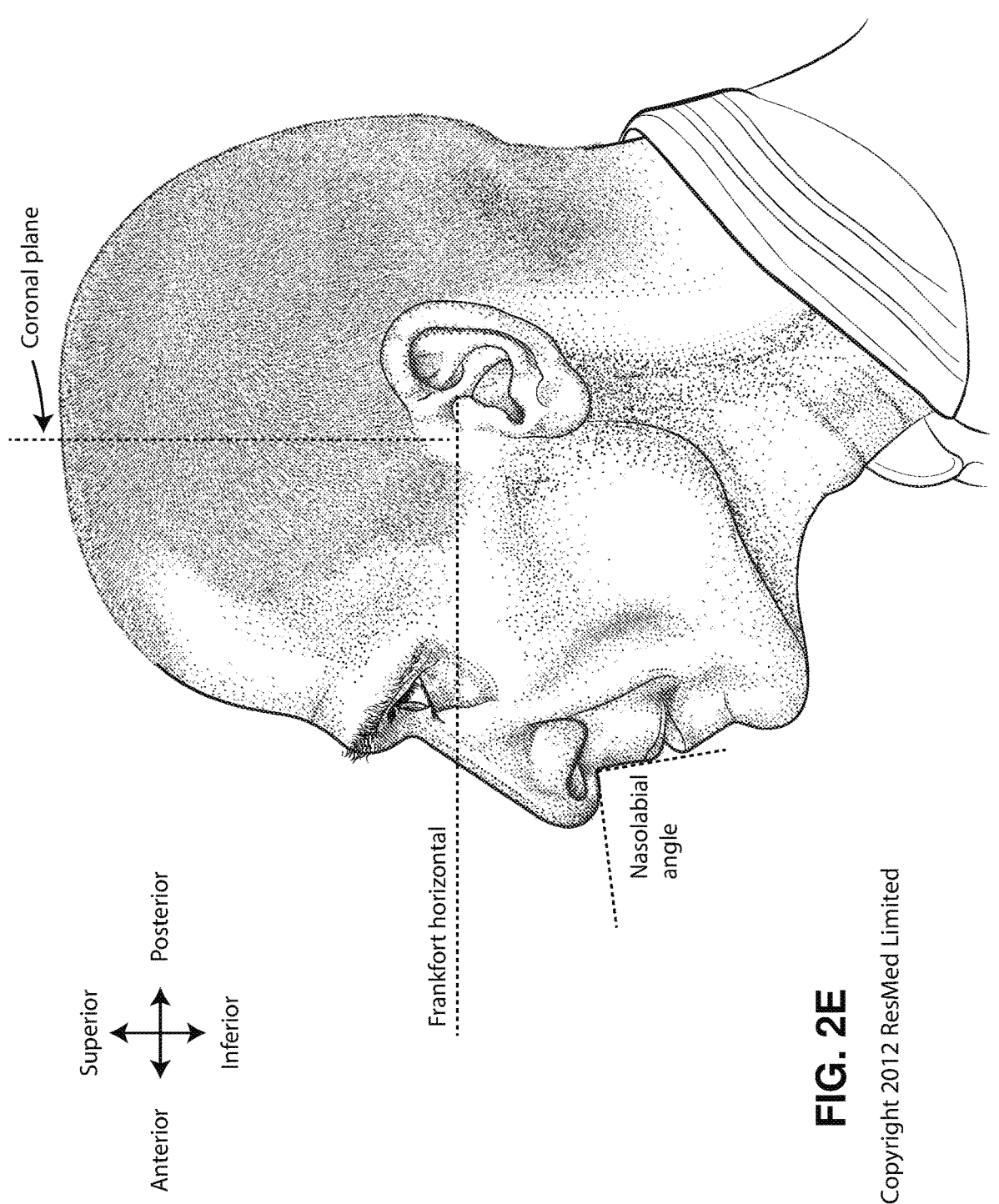

FIG. 2E is a further side view of a head. The approximate locations of the Frankfort horizontal and nasolabial angle are indicated. The coronal plane is also indicated.

Figure 2F:
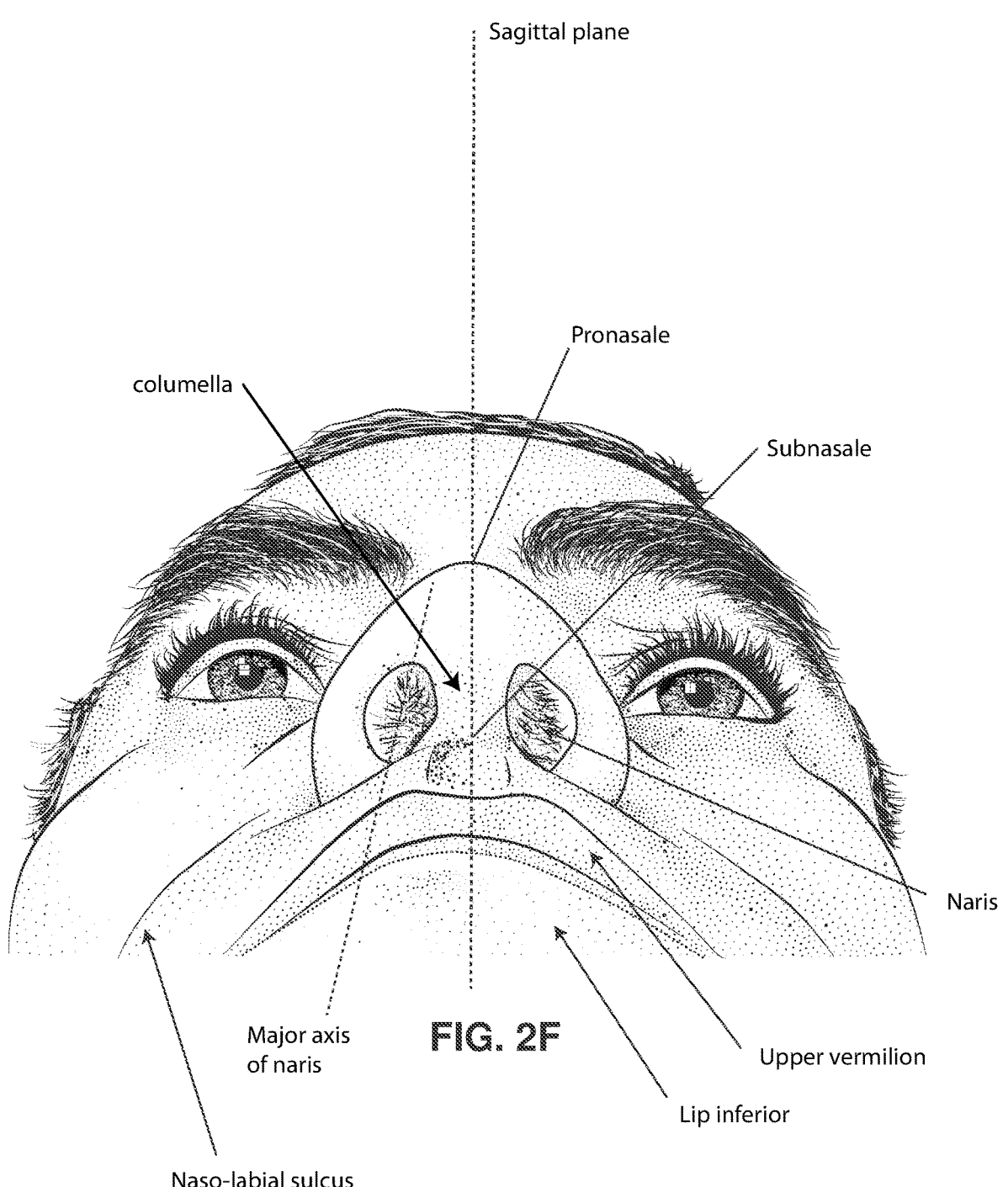

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
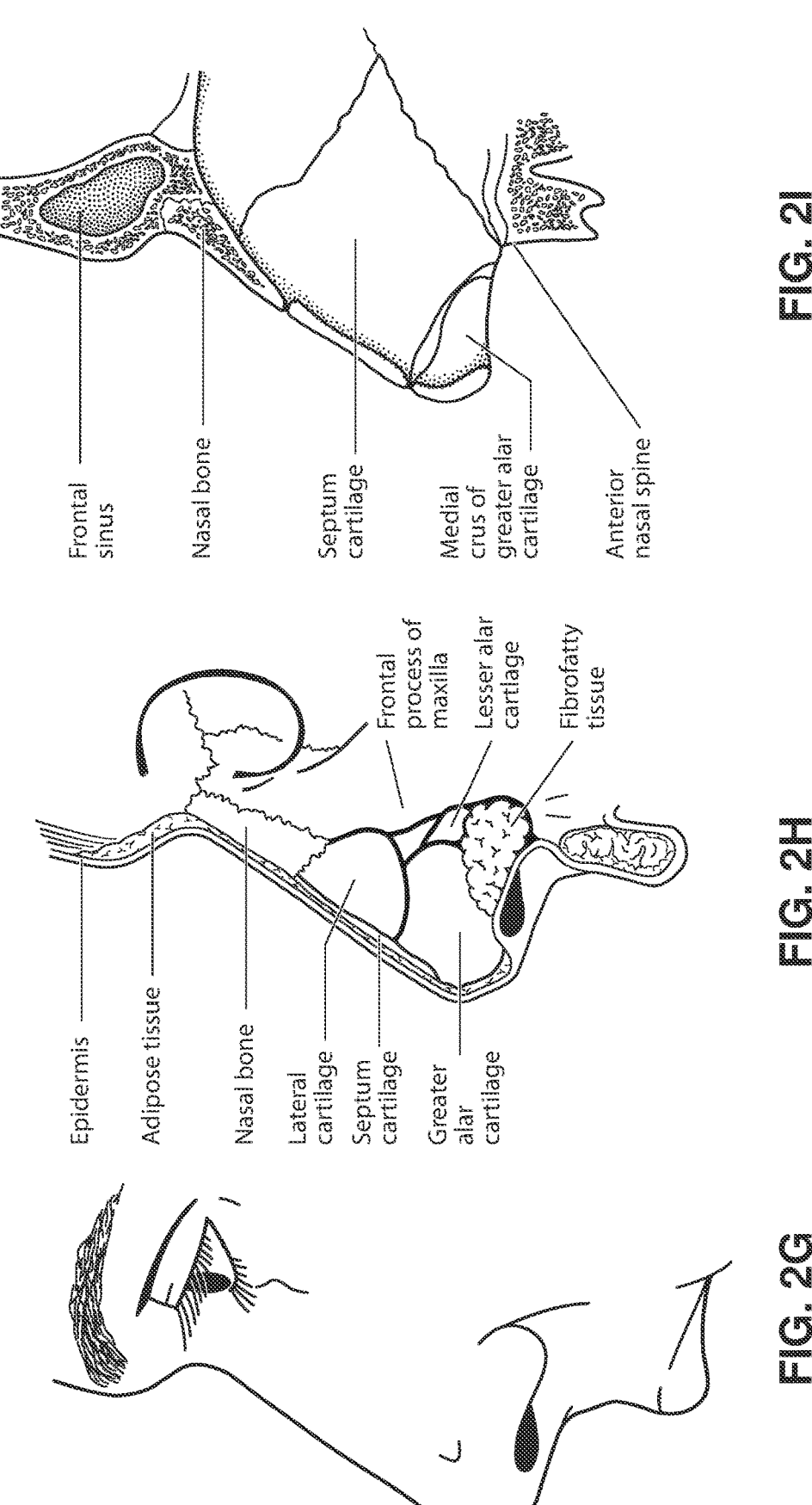

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
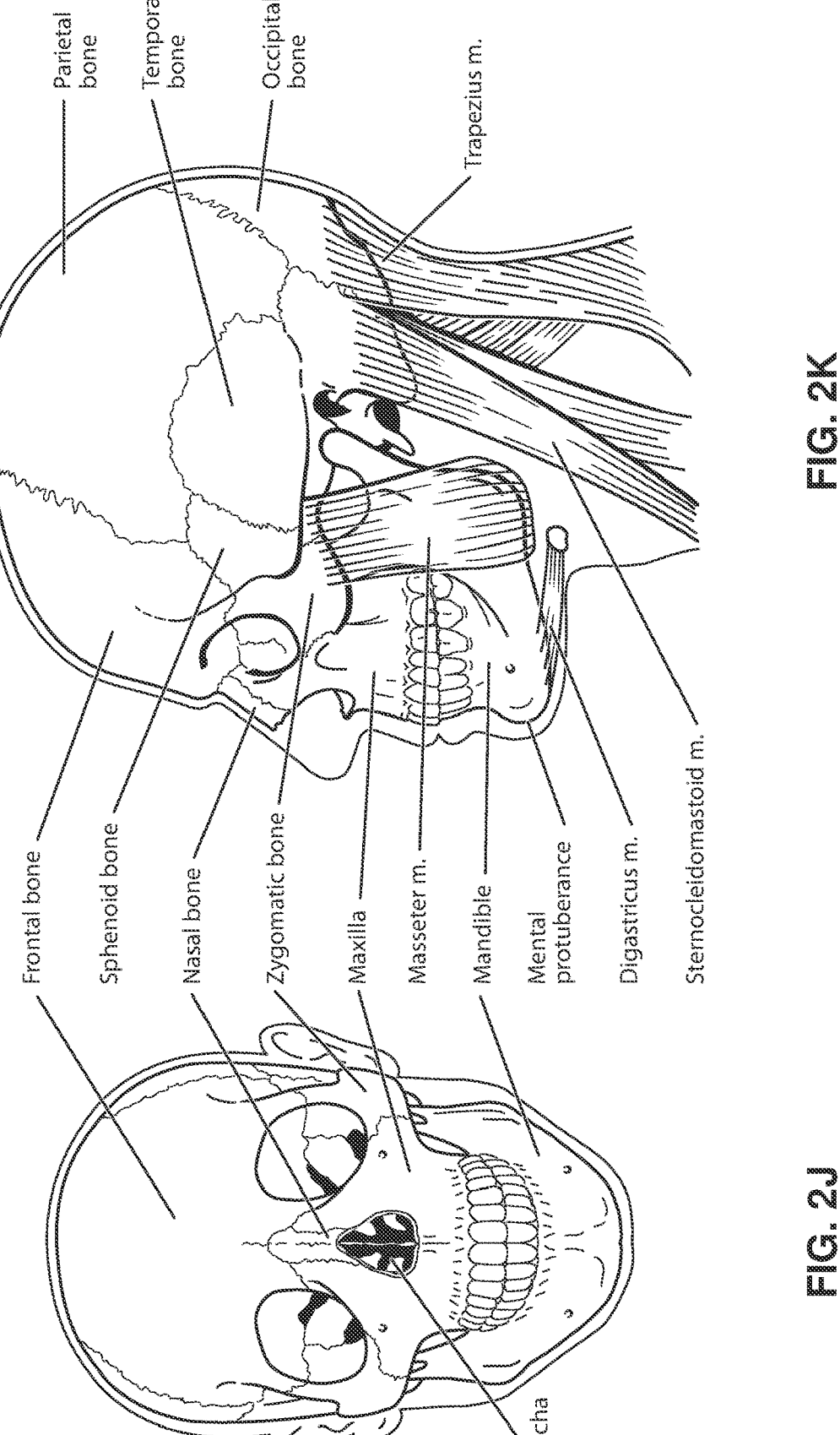

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
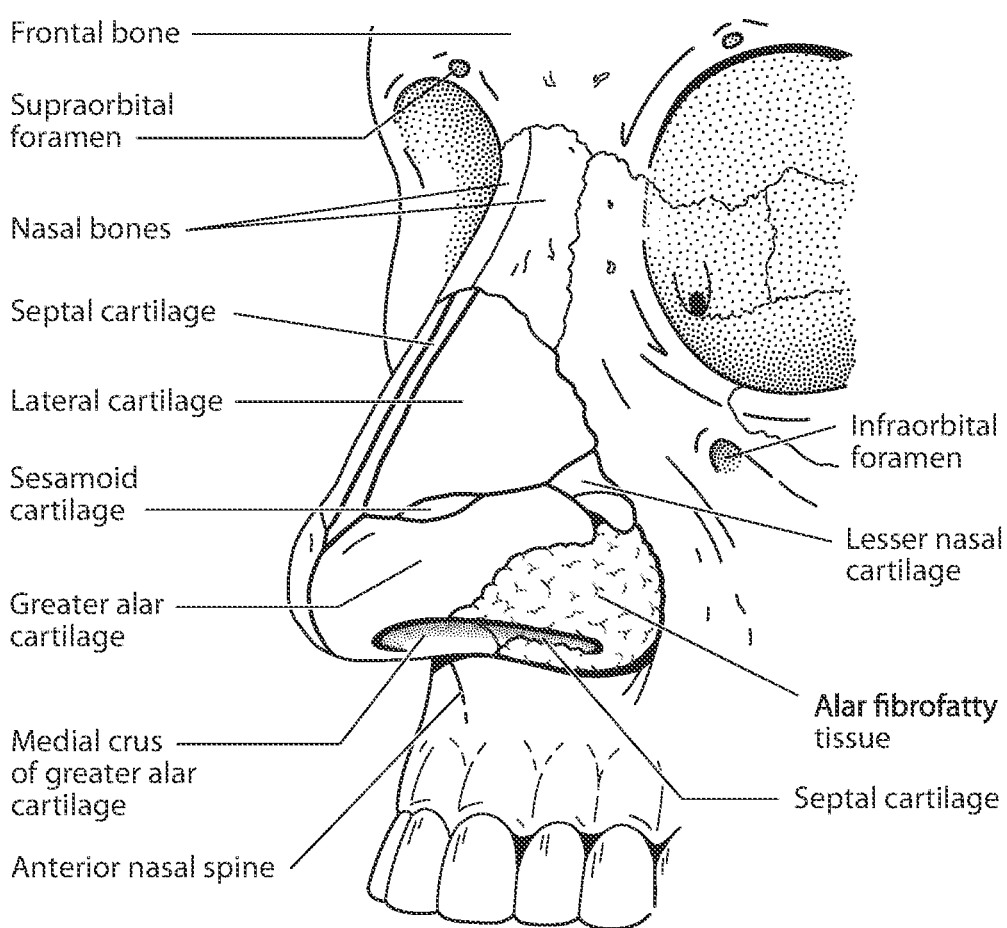

FIG. 2L shows an anterolateral view of a nose.

4.3 Patient Interface

Figure 3A:
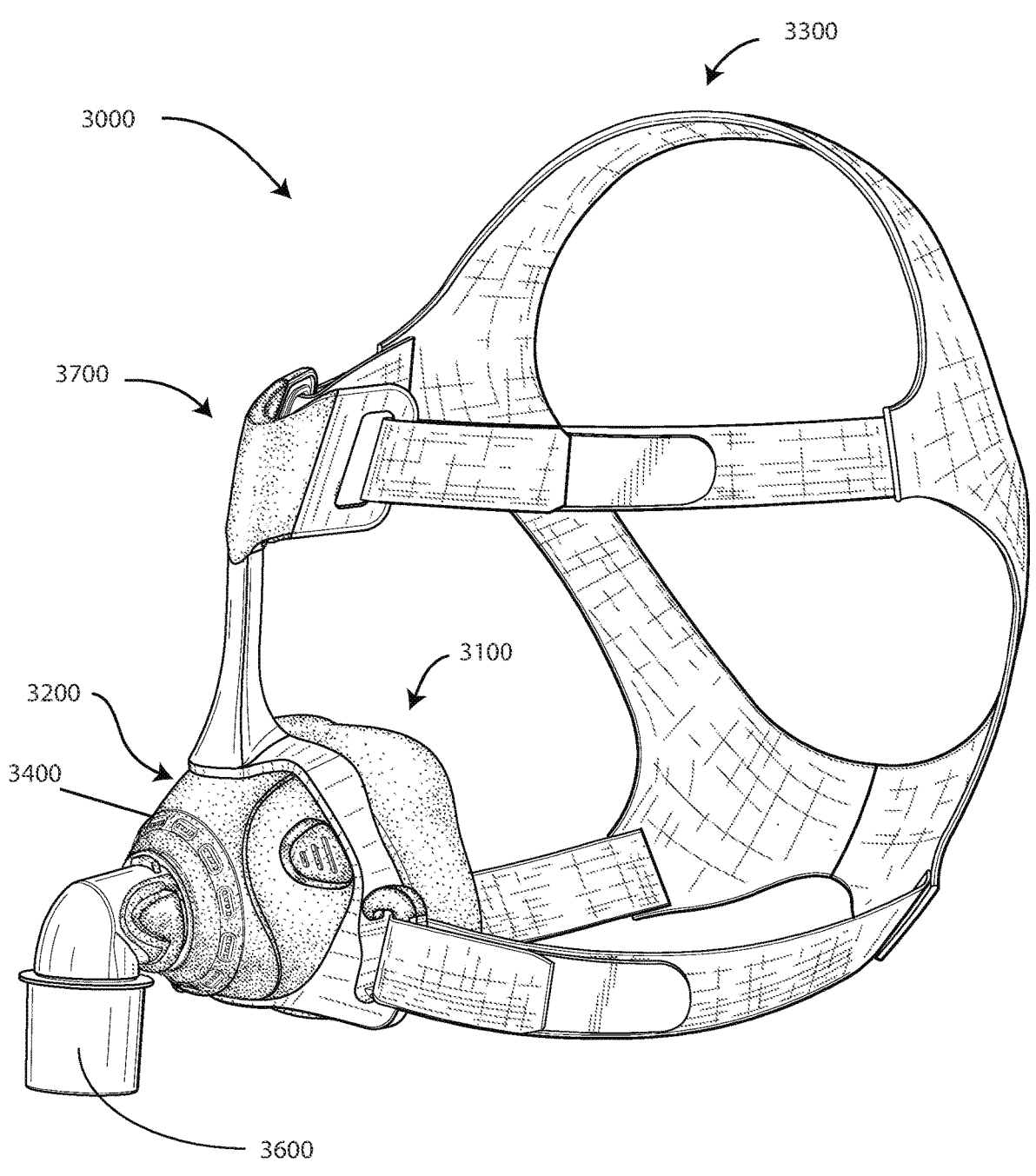

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
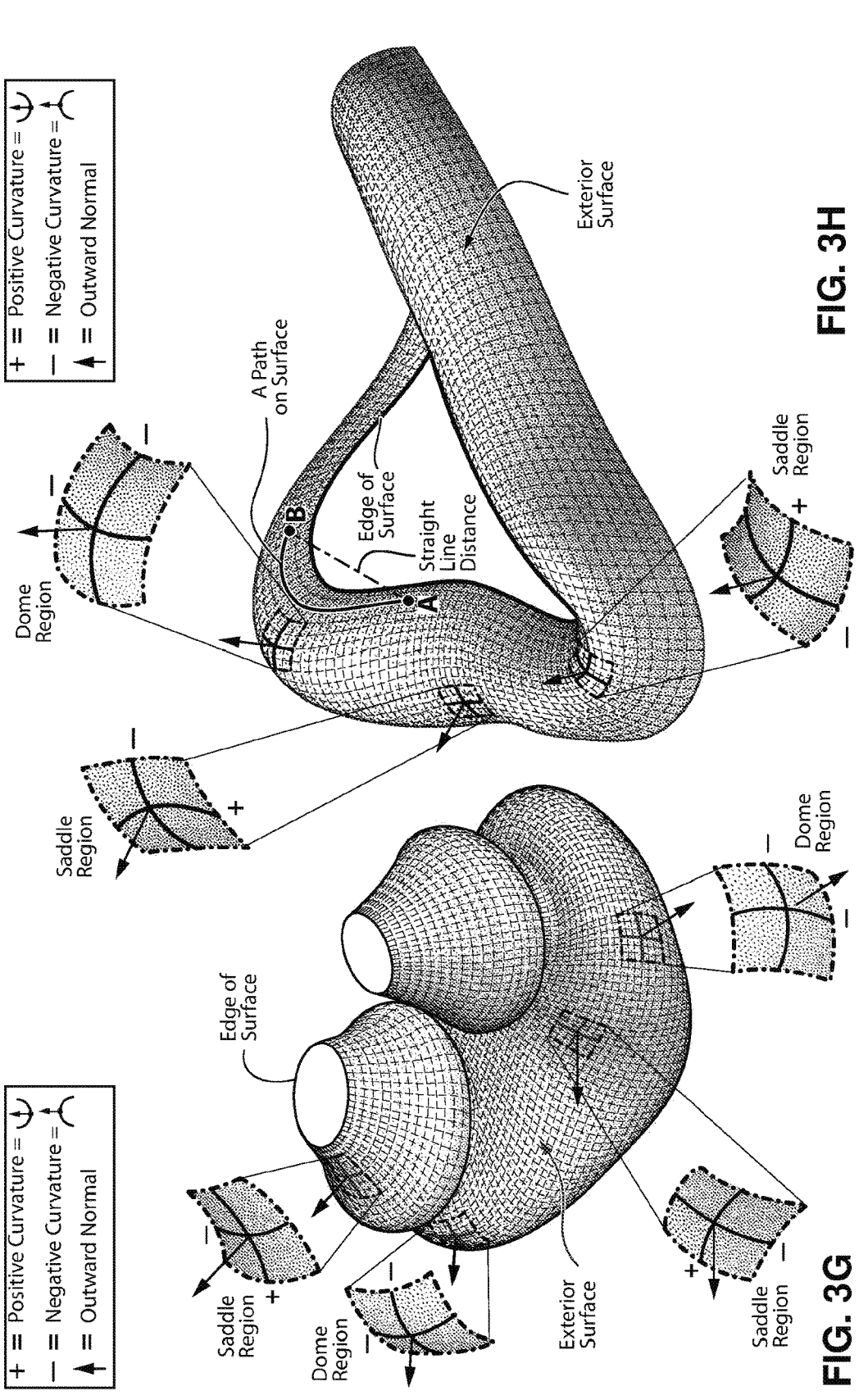

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
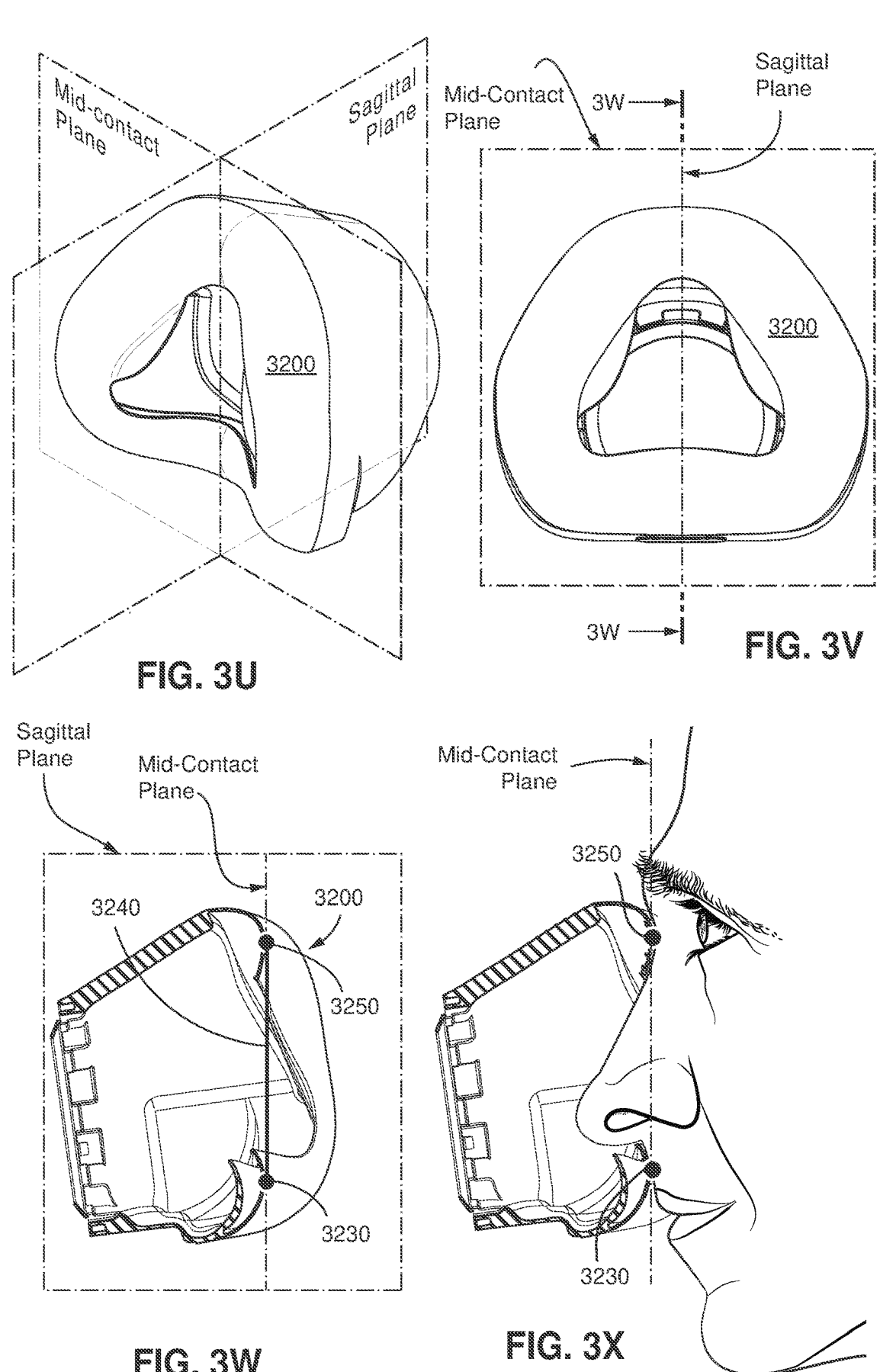

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3240 which lies on the sagittal plane and just touches the cushion of the plenum chamber at two points on the sagittal plane: a superior point 3250 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3250 sits approximately on the sellion, while the inferior point 3230 sits on the lip superior.

Figure 3Y:
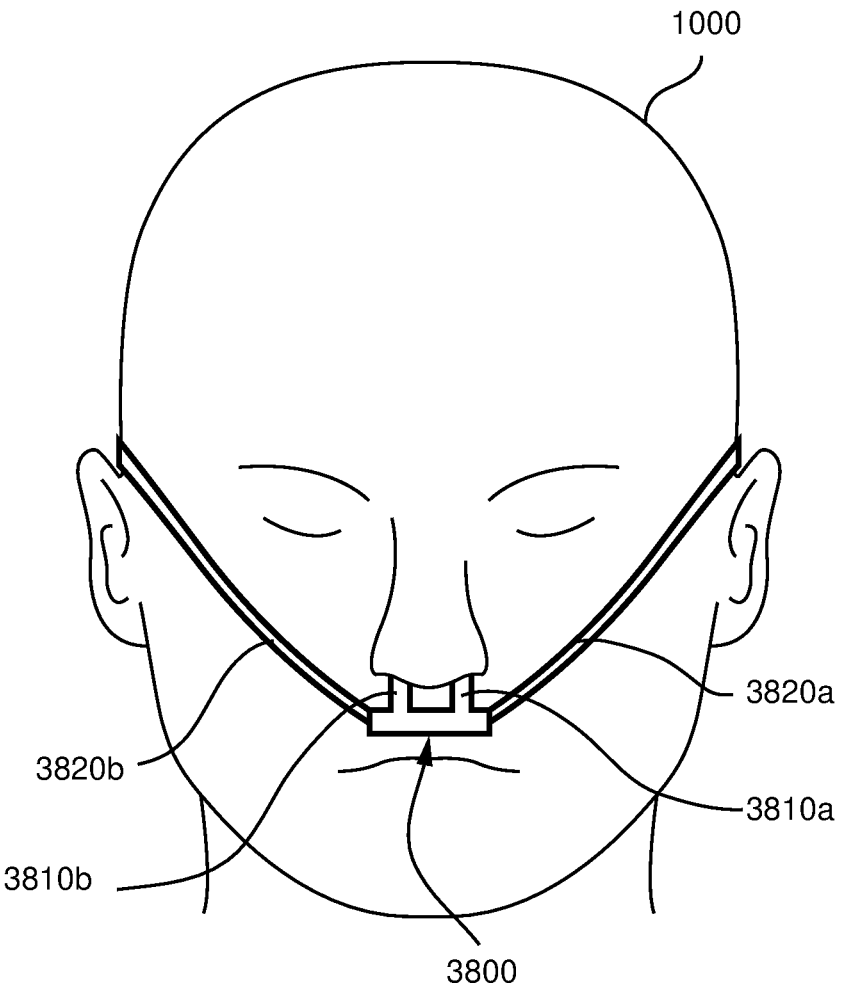

FIG. 3Y shows a patient interface in the form of a nasal cannula in accordance with one form of the present technology.

4.4 RPT Device

Figure 4A:
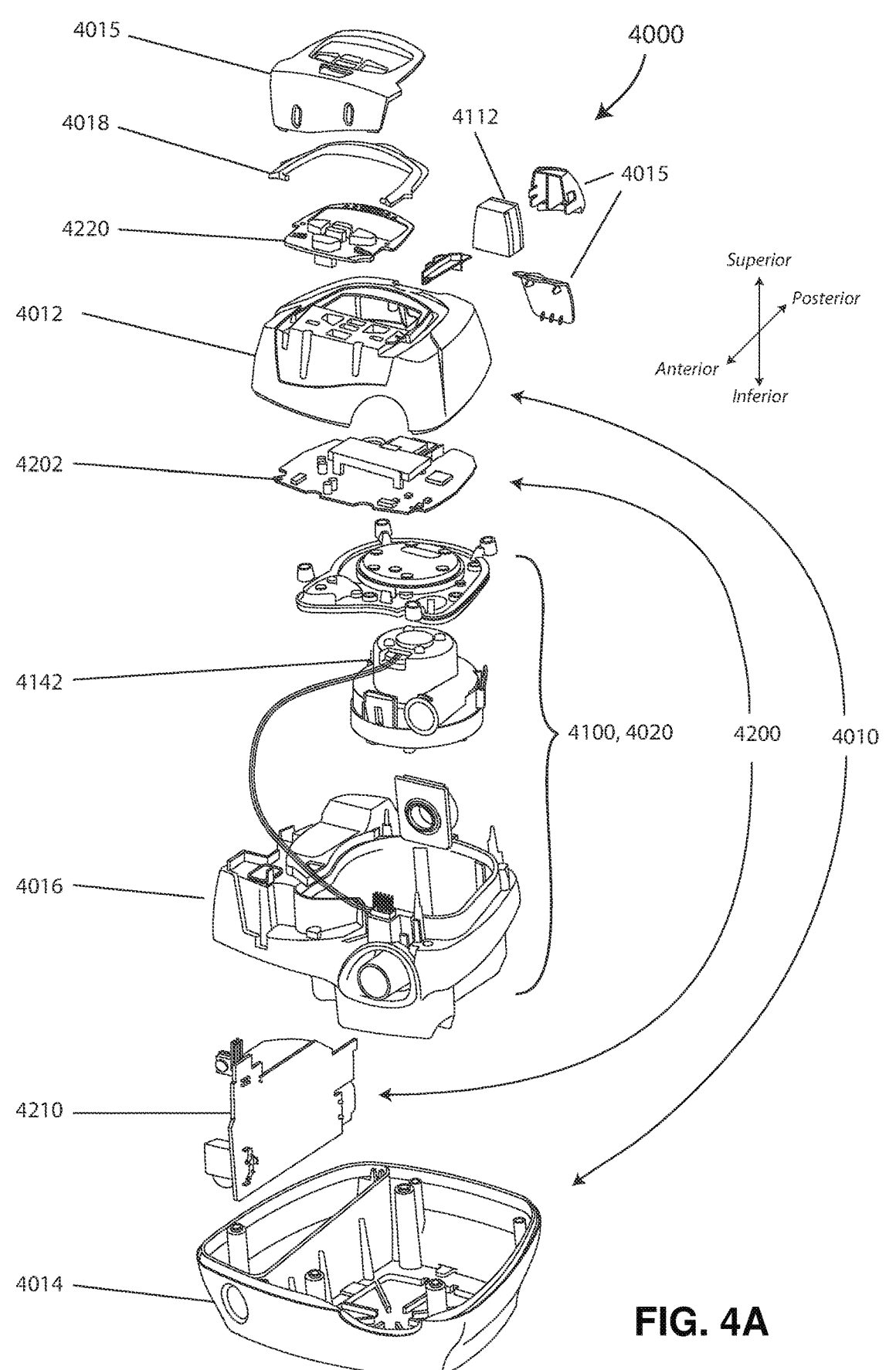

FIG. 4A shows an RPT device in accordance with one form of the present technology.

Figure 4B:
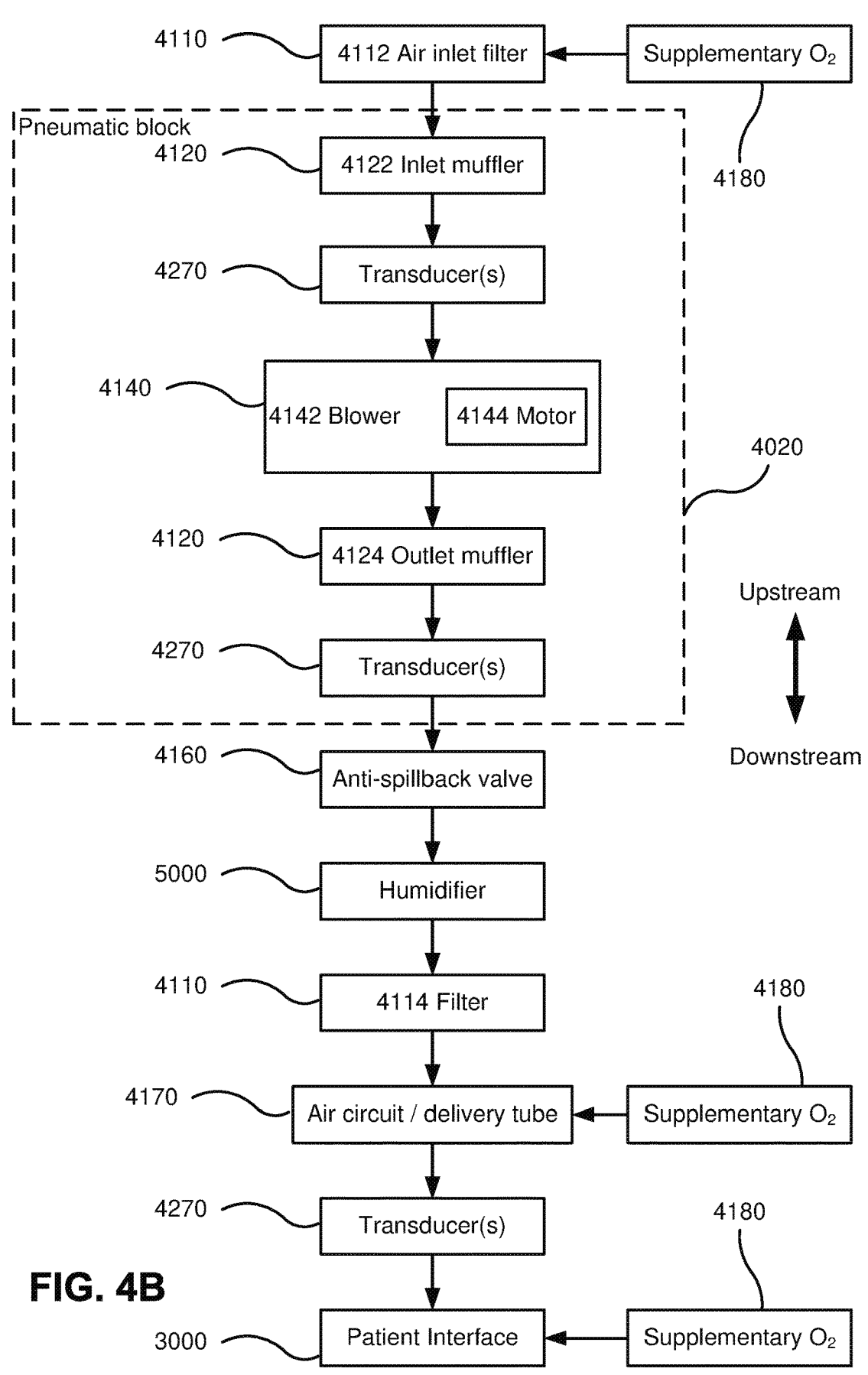

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
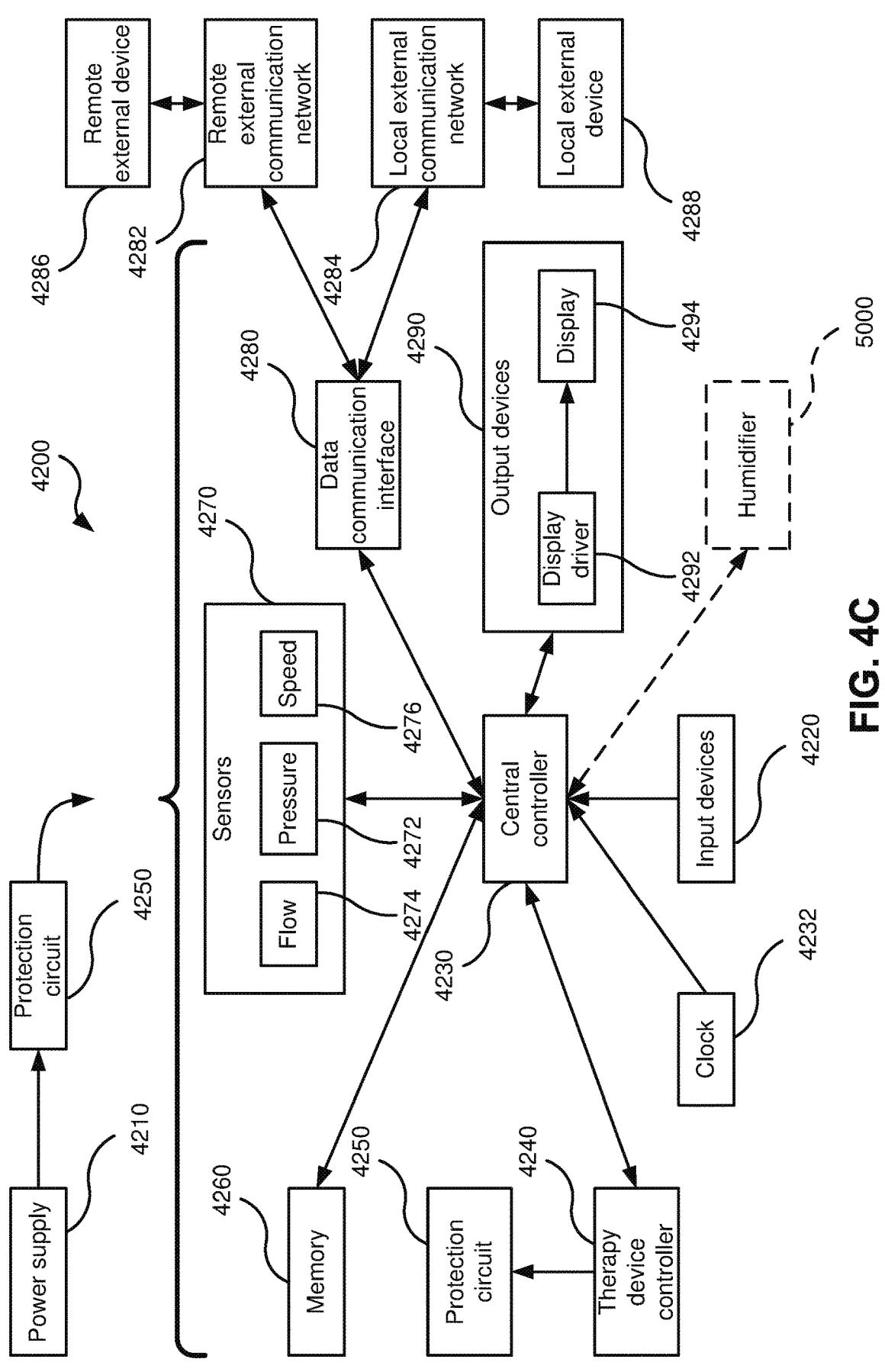

FIG. 4C is a schematic diagram of the electrical components of an RPT device in accordance with one form of the present technology.

4.5 Humidifier

Figure 5A:
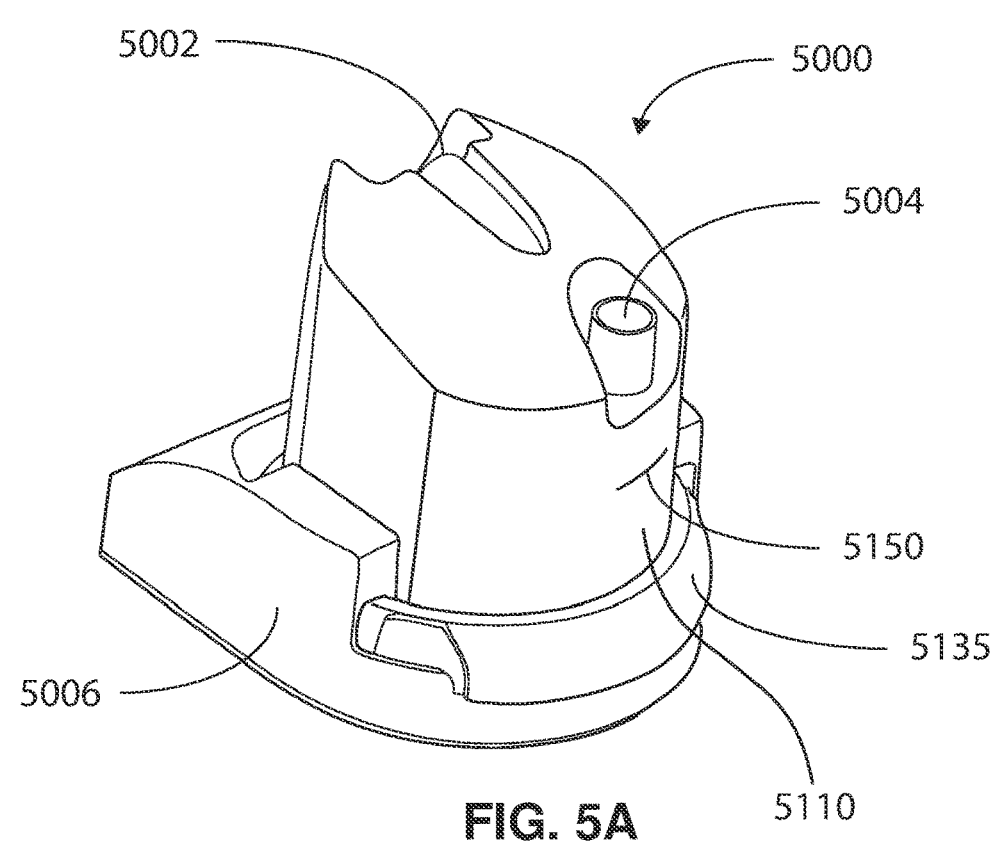

FIG. 5A shows an isometric view of a humidifier in accordance with one form of the present technology.

Figure 5B:
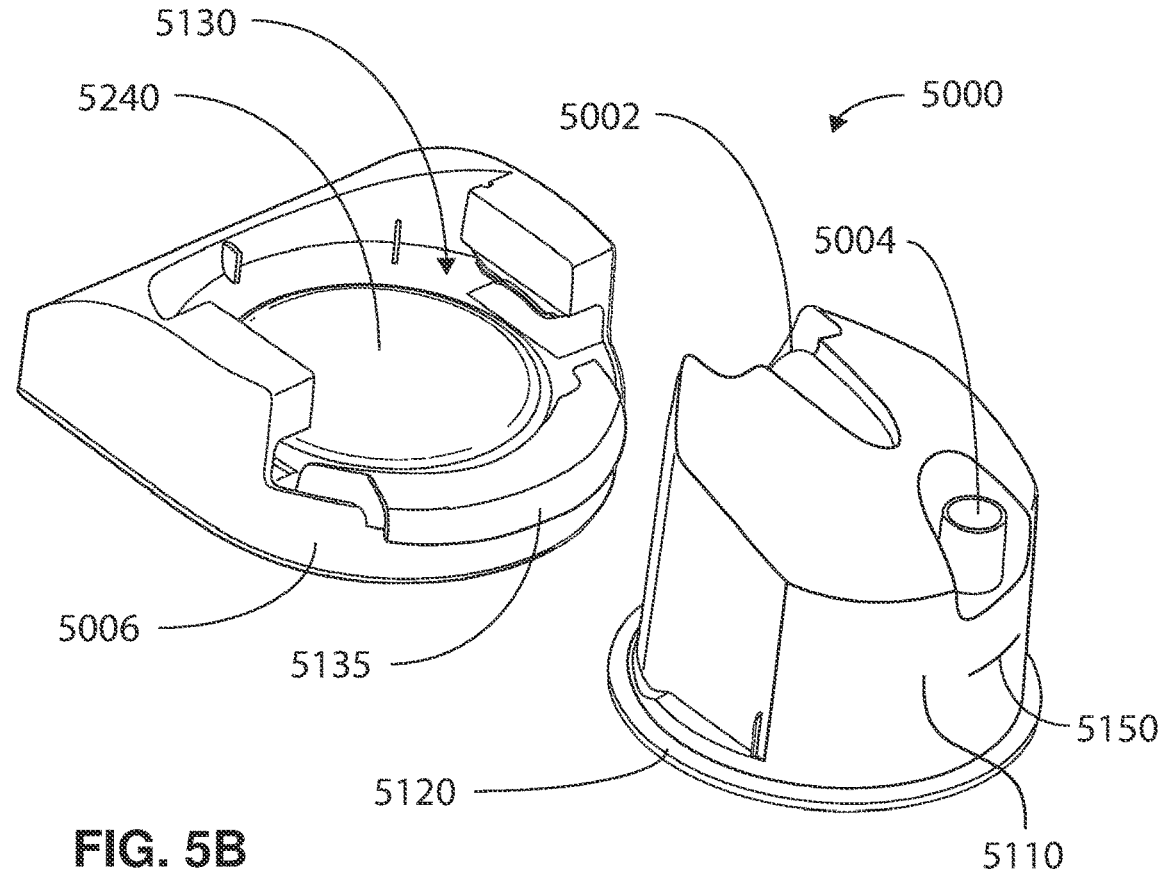

FIG. 5B shows an isometric view of a humidifier in accordance with one form of the present technology, showing a humidifier reservoir 5110 removed from the humidifier reservoir dock 5130.

Figure 5C:
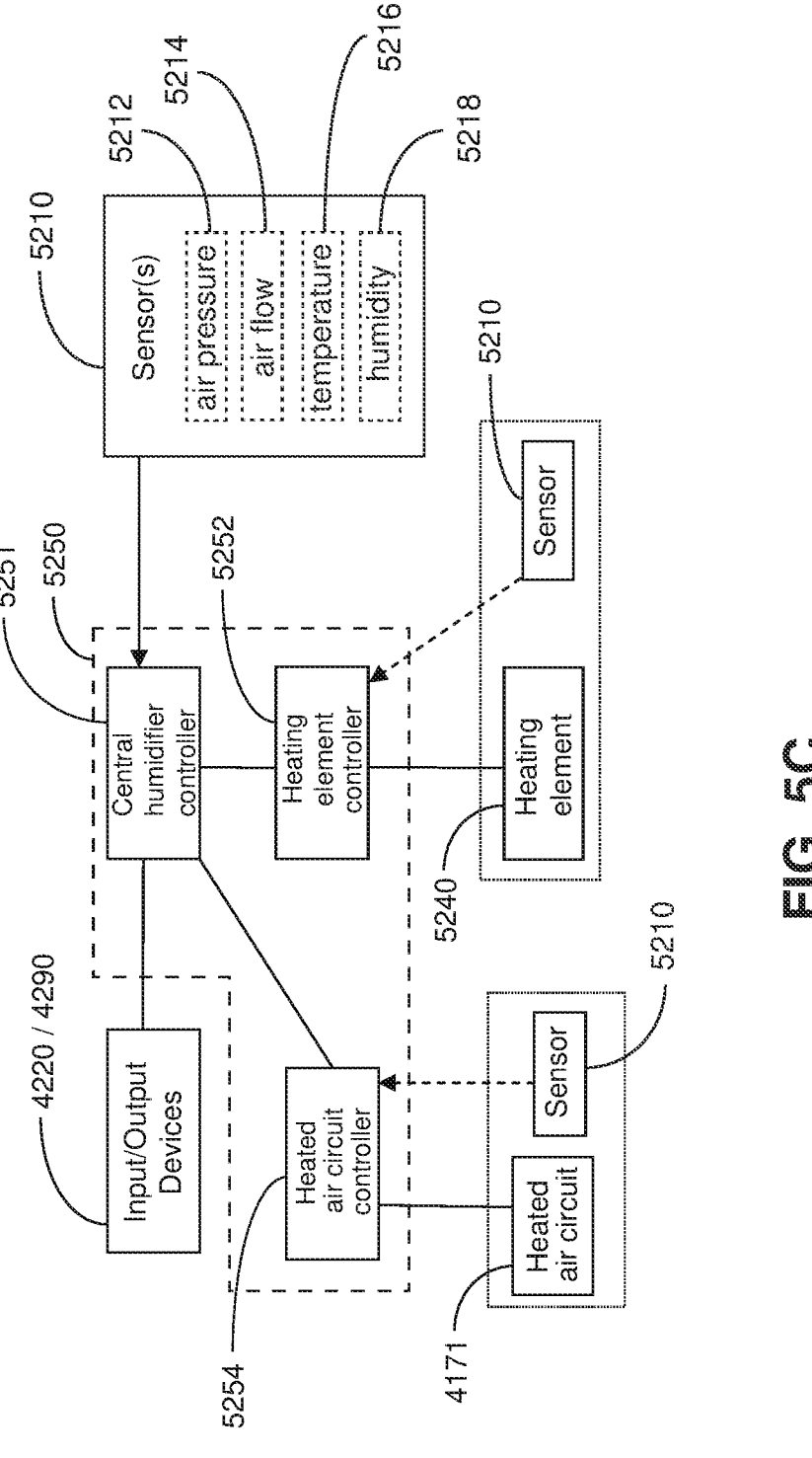

FIG. 5C shows a schematic of a humidifier in accordance with one form of the present technology.

4.6 Breathing Waveforms

Figure 6:
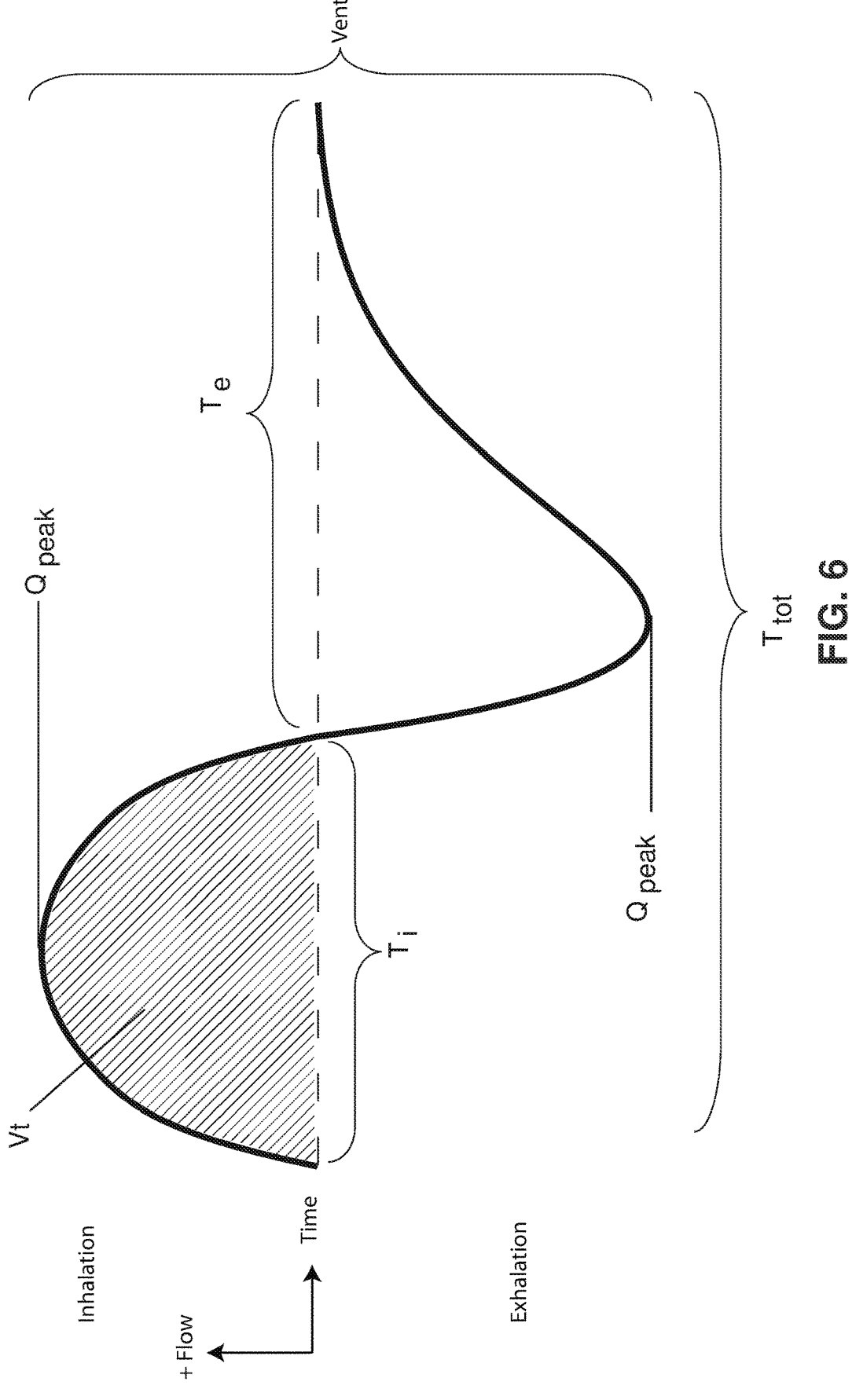

FIG. 6 shows a model typical breath waveform of a person while sleeping.

4.7 HME and Patient Interface of the Present Technology

Figure 7:
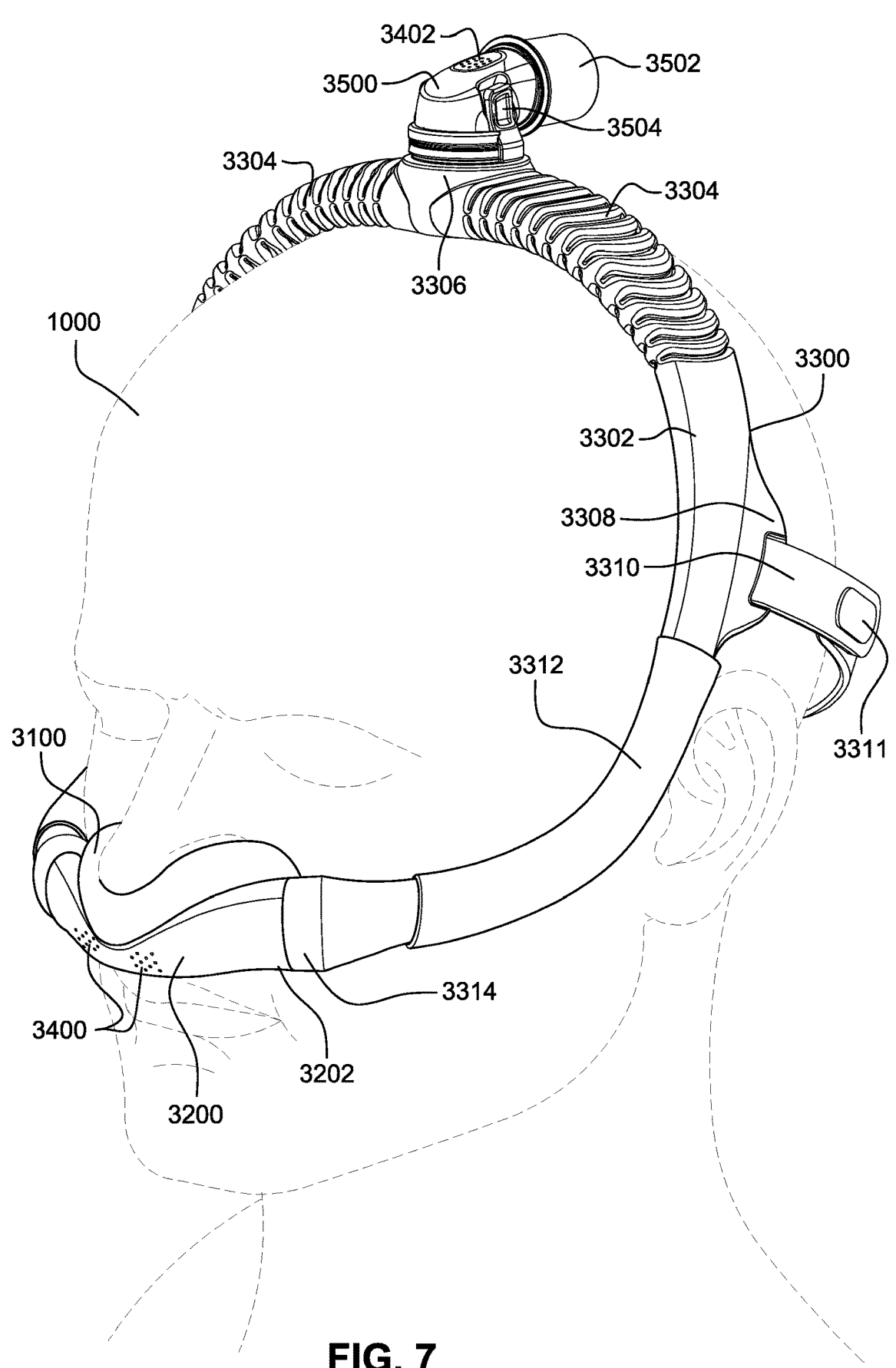

FIG. 7 is an anterolateral view from a superior position of a patient interface according to an example of the present technology worn by a patient.

Figure 8:
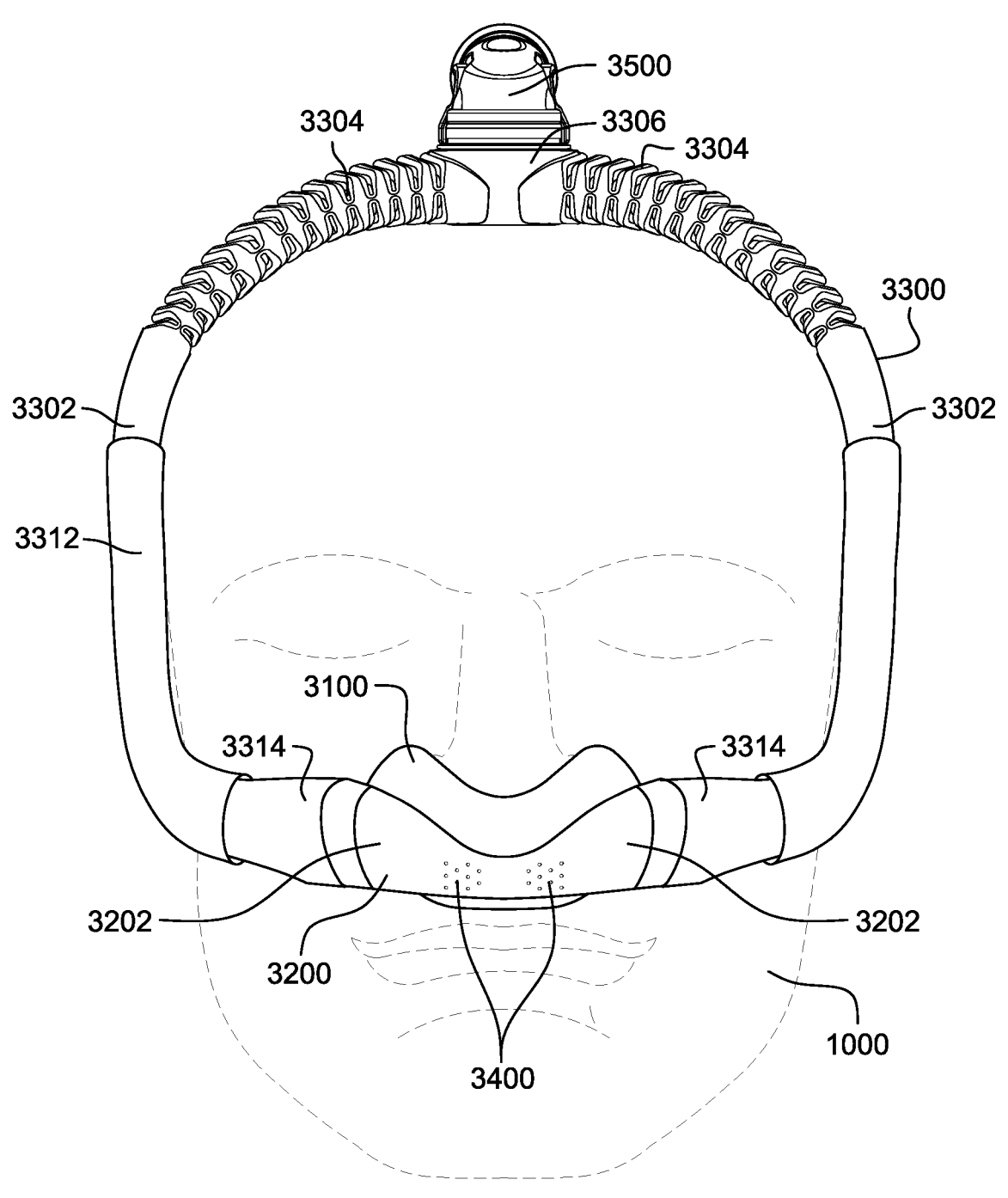

FIG. 8 is an anterior view of a patient interface according to an example of the present technology worn by a patient.

Figure 9:
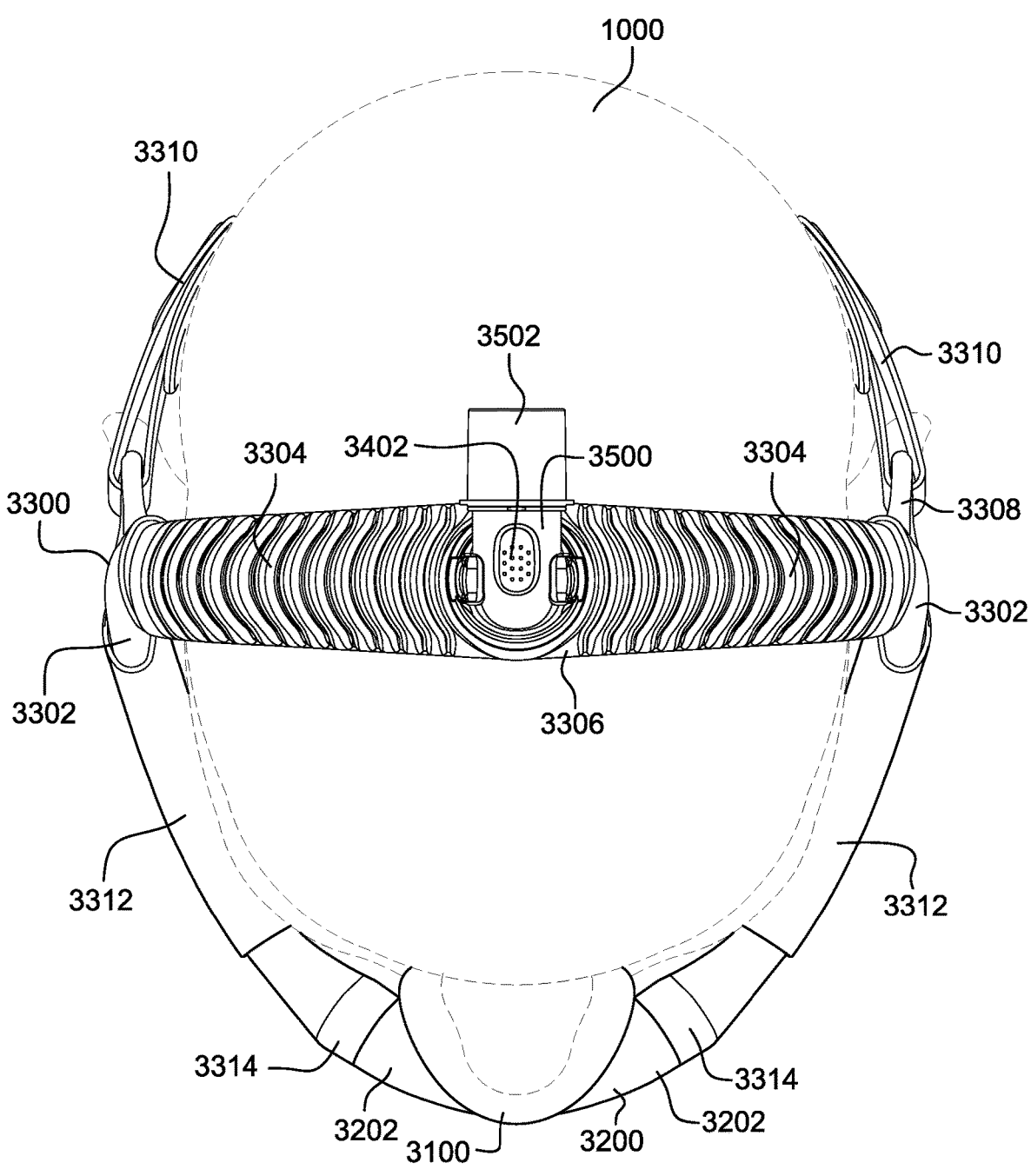

FIG. 9 is a superior view of a patient interface according to an example of the present technology worn by a patient.

Figure 10:
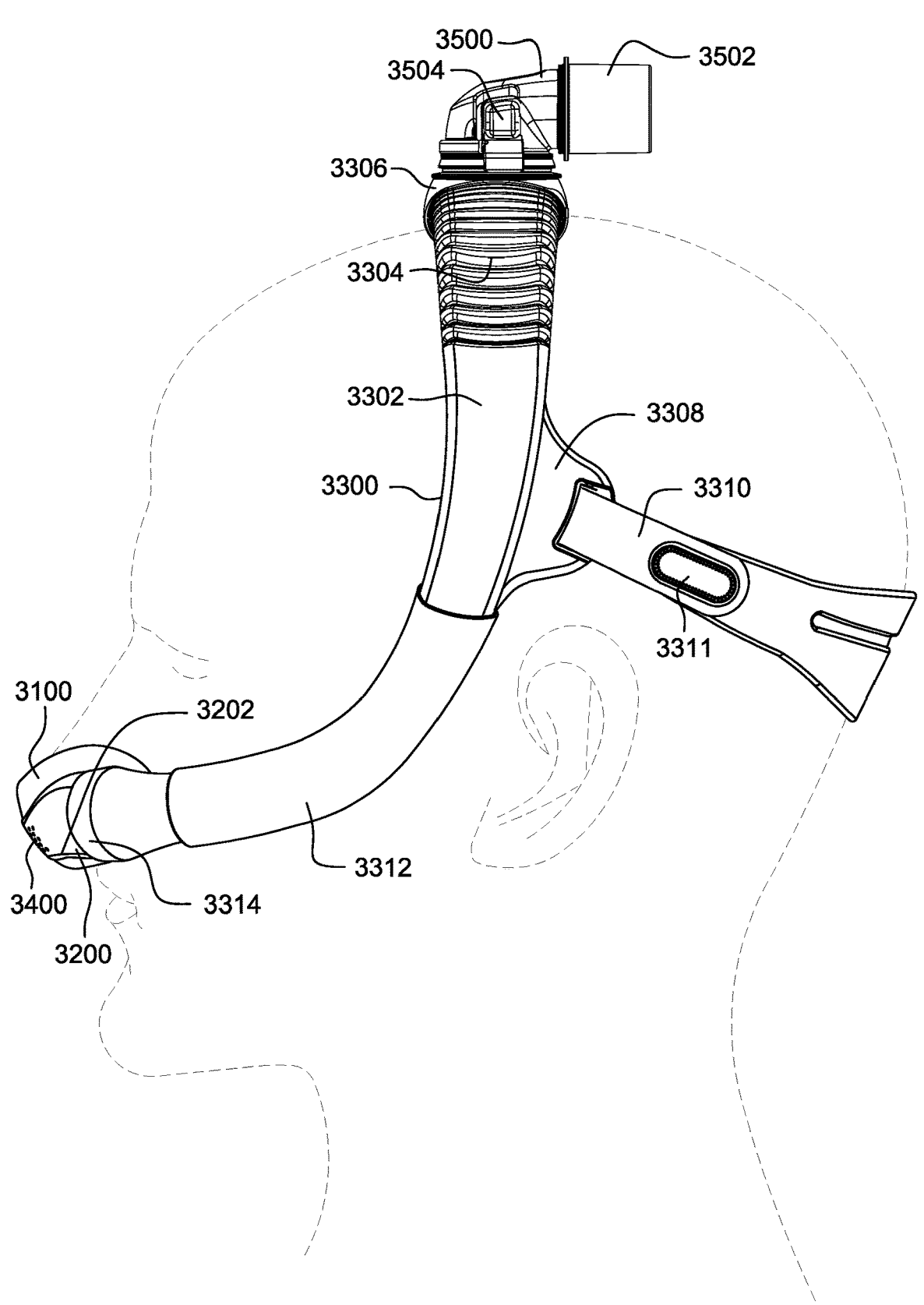

FIG. 10 is a lateral view of a patient interface according to an example of the present technology worn by a patient.

Figure 11:
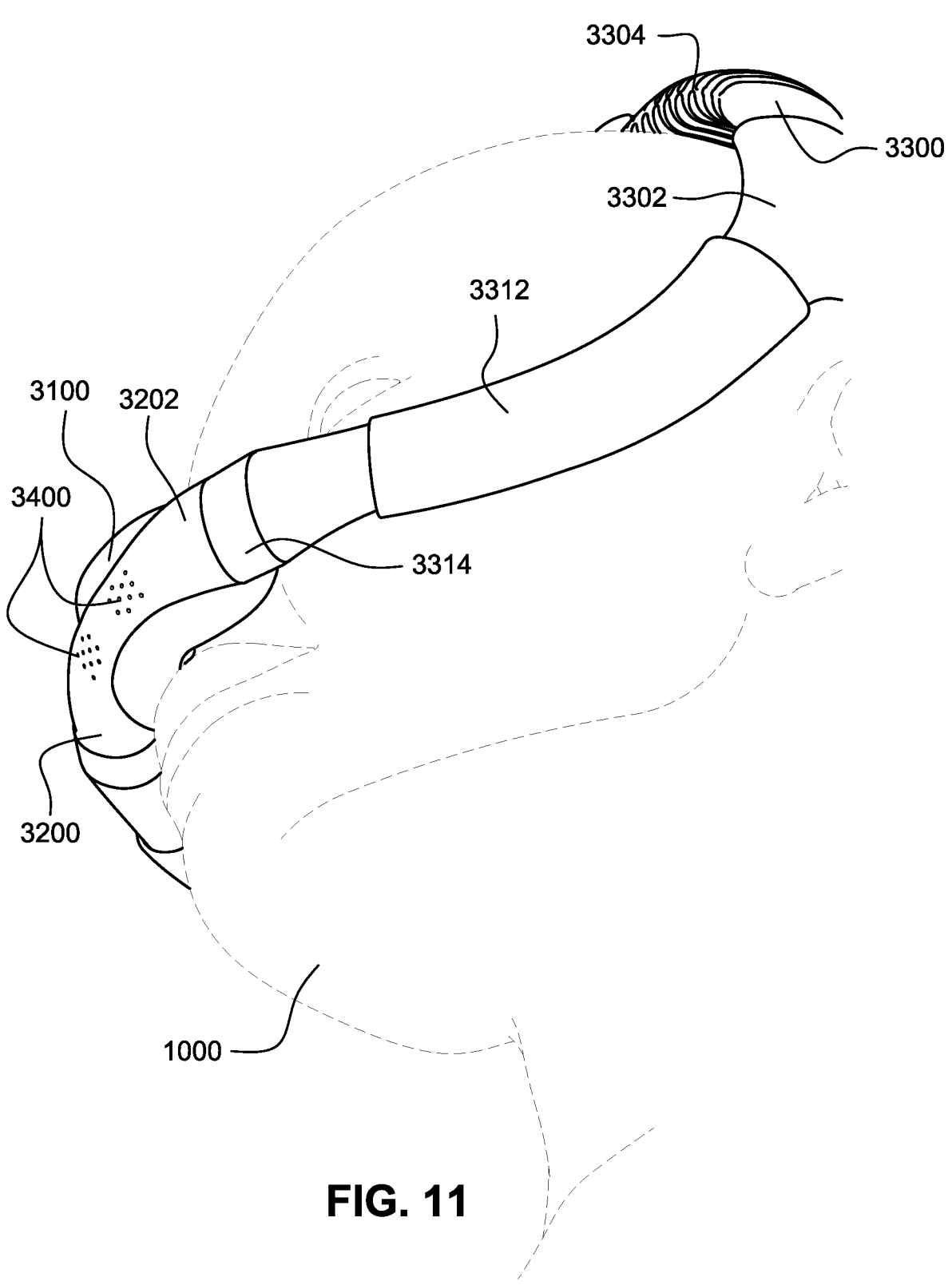

FIG. 11 is an anterolateral view from a superior position of a patient interface according to an example of the present technology worn by a patient.

Figure 12:
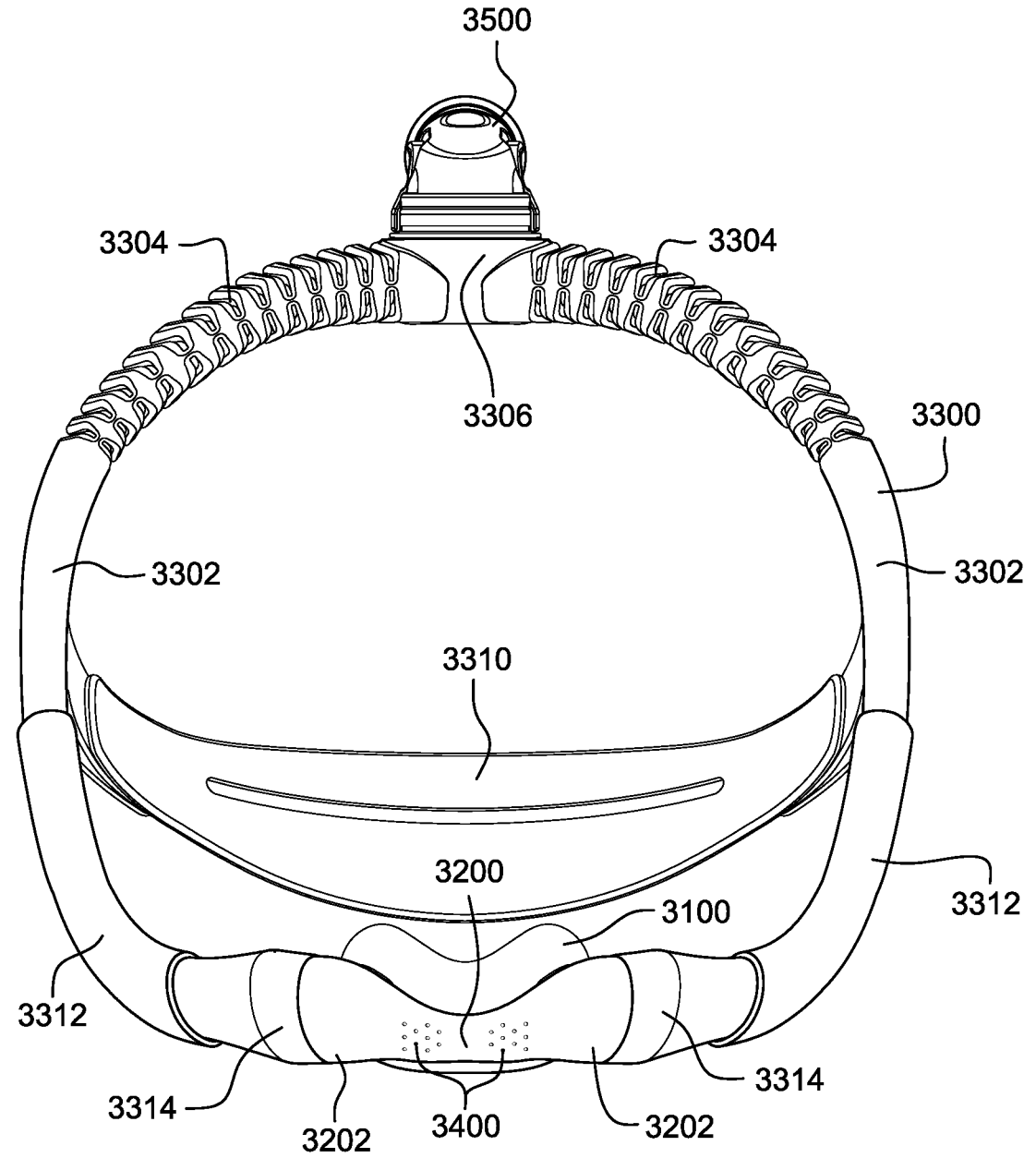

FIG. 12 is an anterior view of a patient interface according to an example of the present technology.

Figure 13:
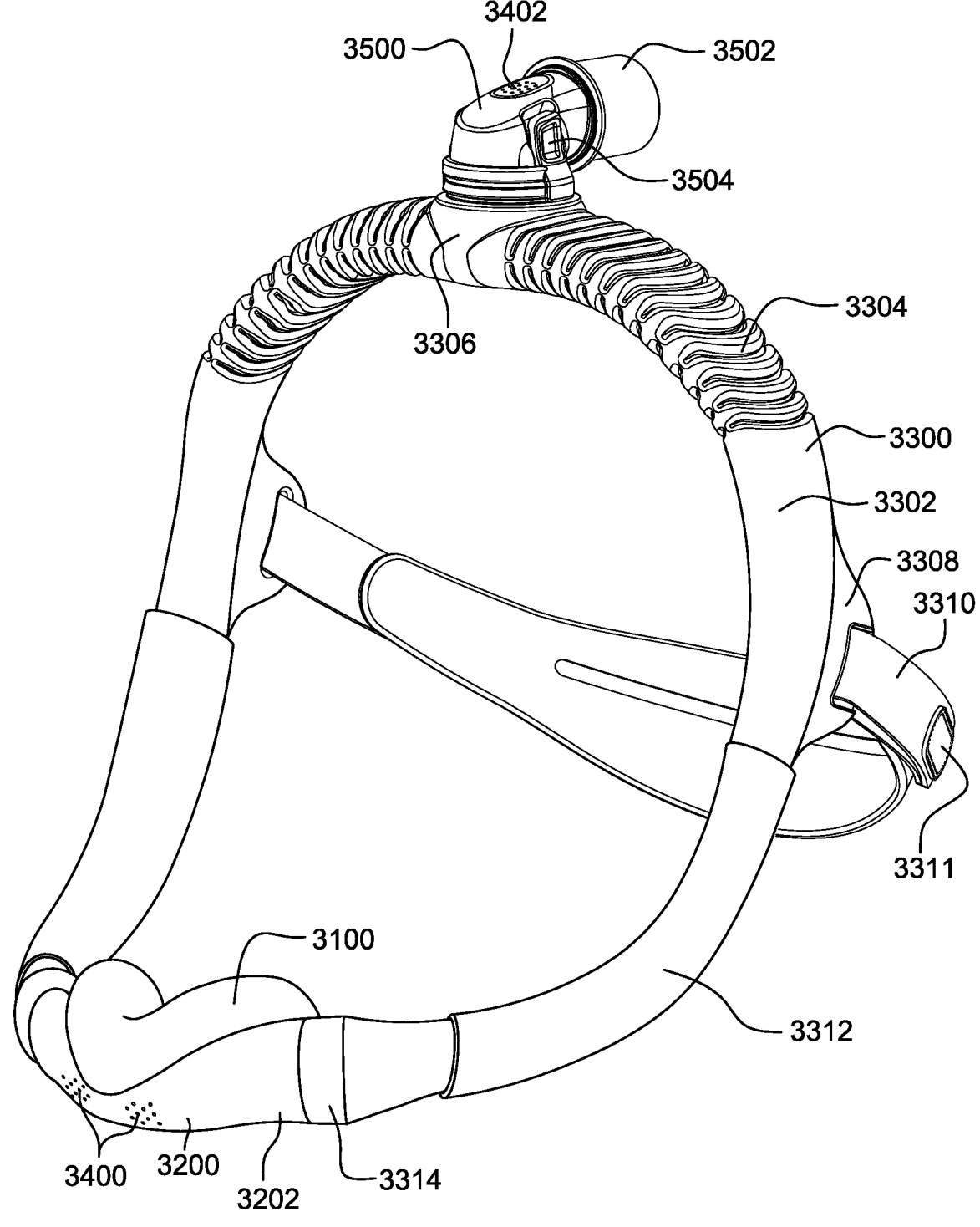

FIG. 13 is an anterolateral view from a superior position of a patient interface according to an example of the present technology.

Figure 14:
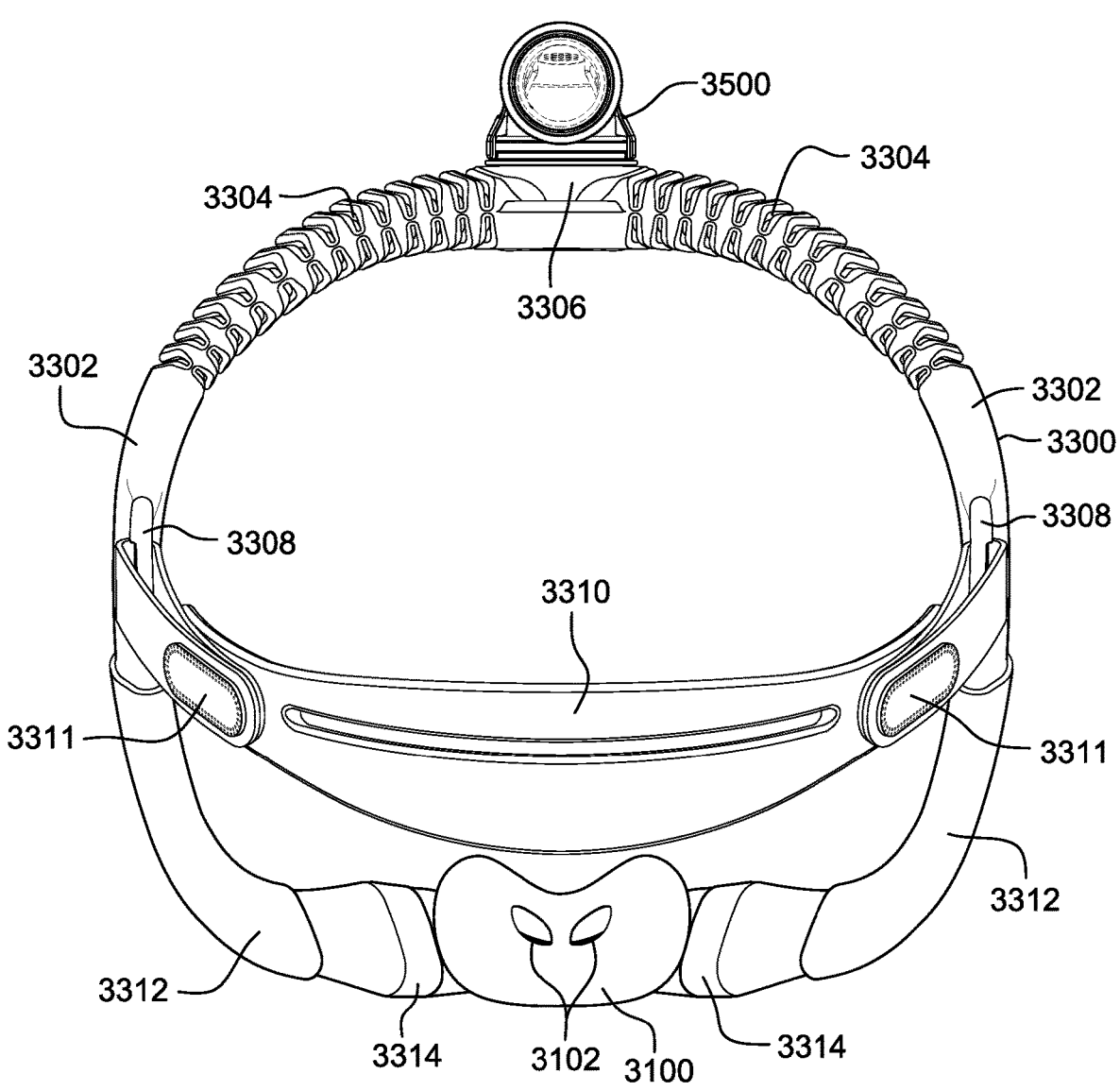

FIG. 14 is a posterior view of a patient interface according to an example of the present technology.

Figure 15:
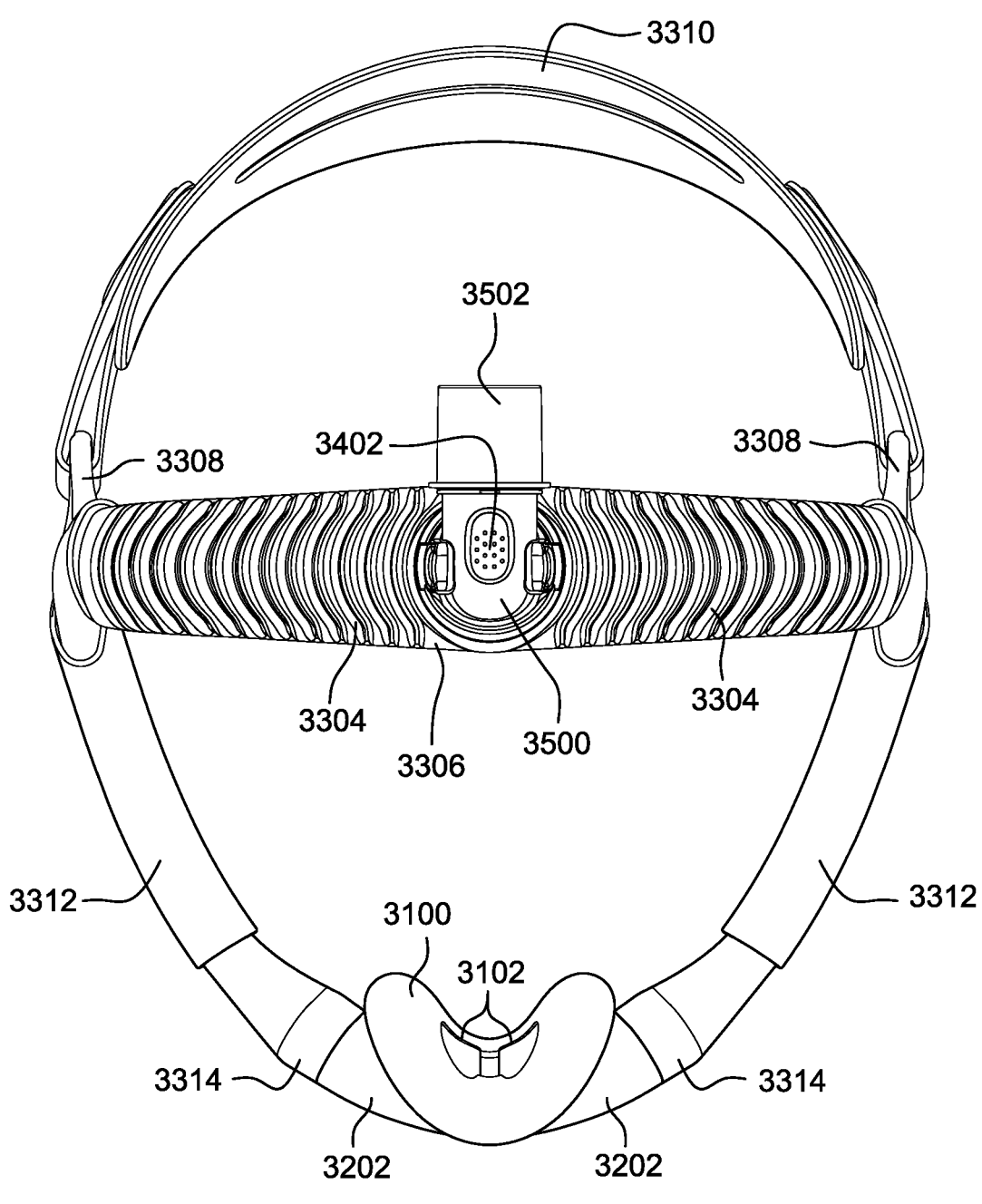

FIG. 15 is a superior view of a patient interface according to an example of the present technology.

Figures 16, 17, 18:
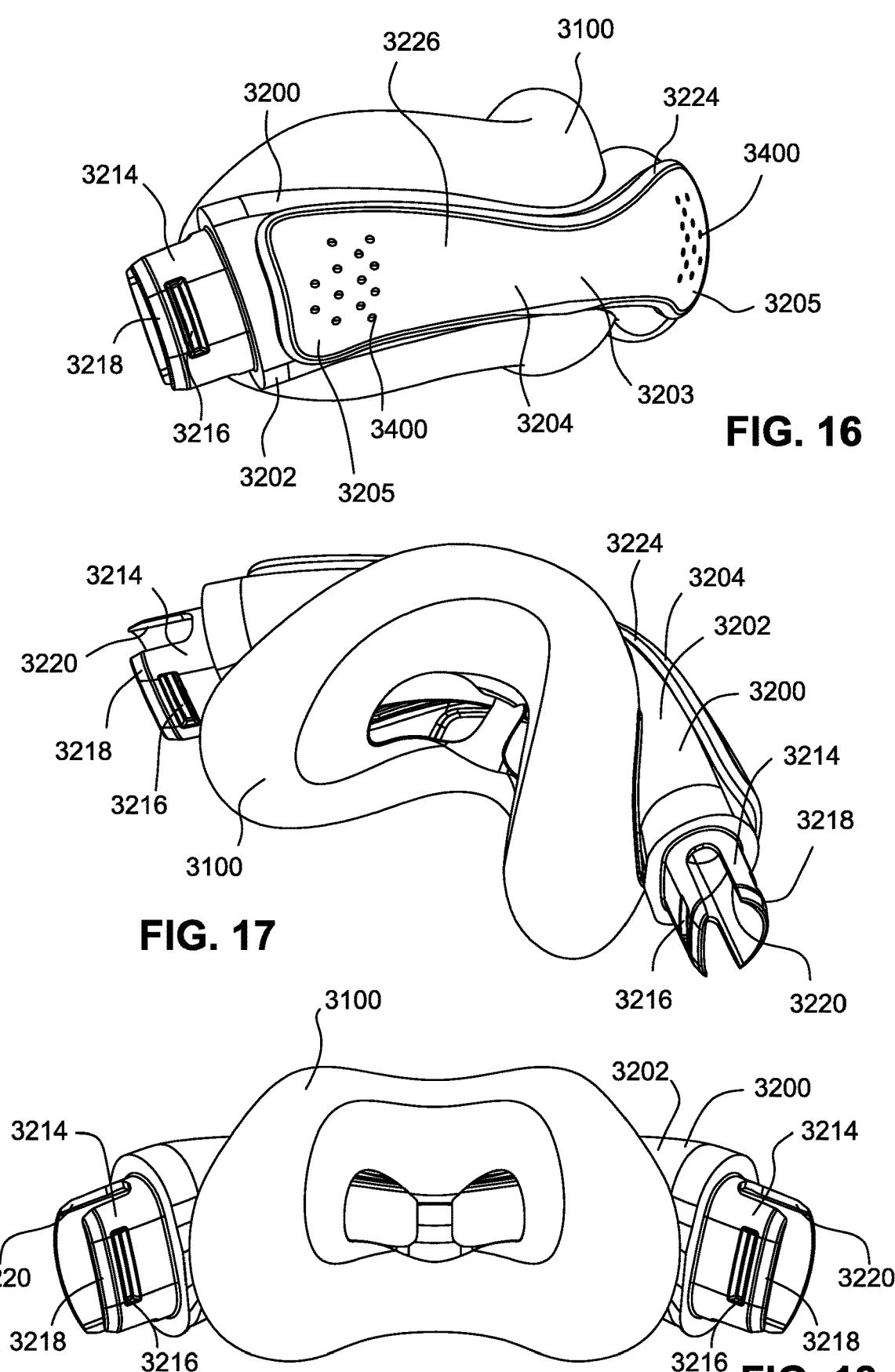

FIG. 16 is an anterior perspective view of a seal-forming structure and a plenum chamber of a patient interface according to an example of the present technology.

FIG. 17 is a posterior perspective view of a seal-forming structure and a plenum chamber of a patient interface according to an example of the present technology.

FIG. 18 is a posterior view of a seal-forming structure and a plenum chamber of a patient interface according to an example of the present technology.

Figure 19:
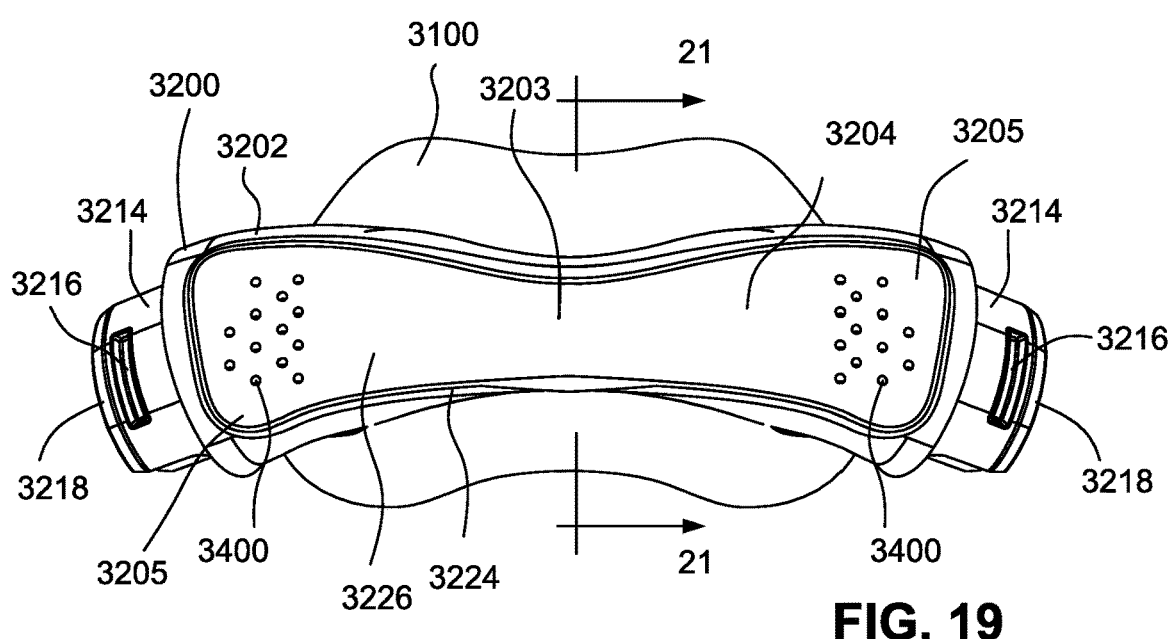

FIG. 19 is an anterior view of a seal-forming structure and a plenum chamber of a patient interface according to an example of the present technology.

Figure 20:
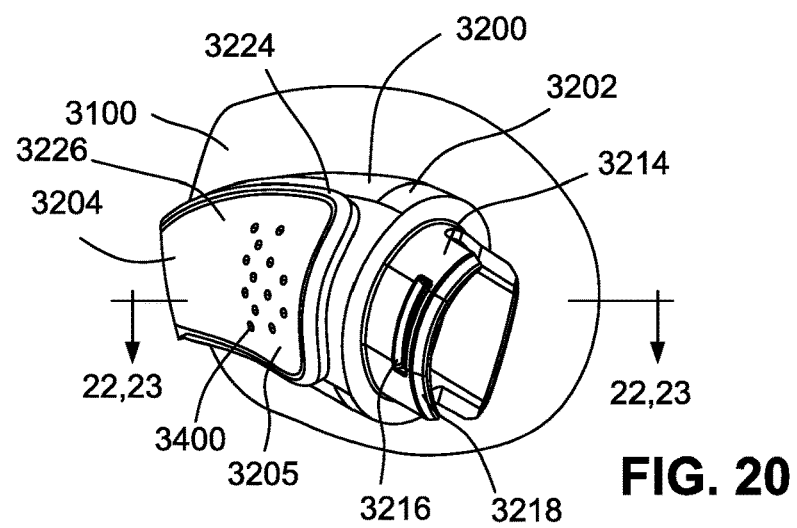

FIG. 20 is a lateral view of a seal-forming structure and a plenum chamber of a patient interface according to an example of the present technology.

Figure 21:
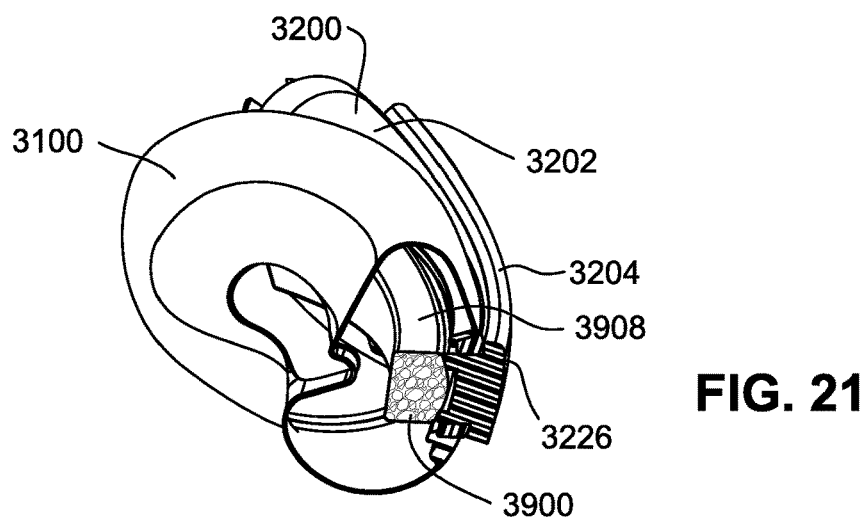

FIG. 21 is a cross-sectional view taken through line 21-21 of FIG. 19 of a seal-forming structure, a plenum chamber, and a heat and moisture exchanger of a patient interface according to an example of the present technology.

Figure 22:
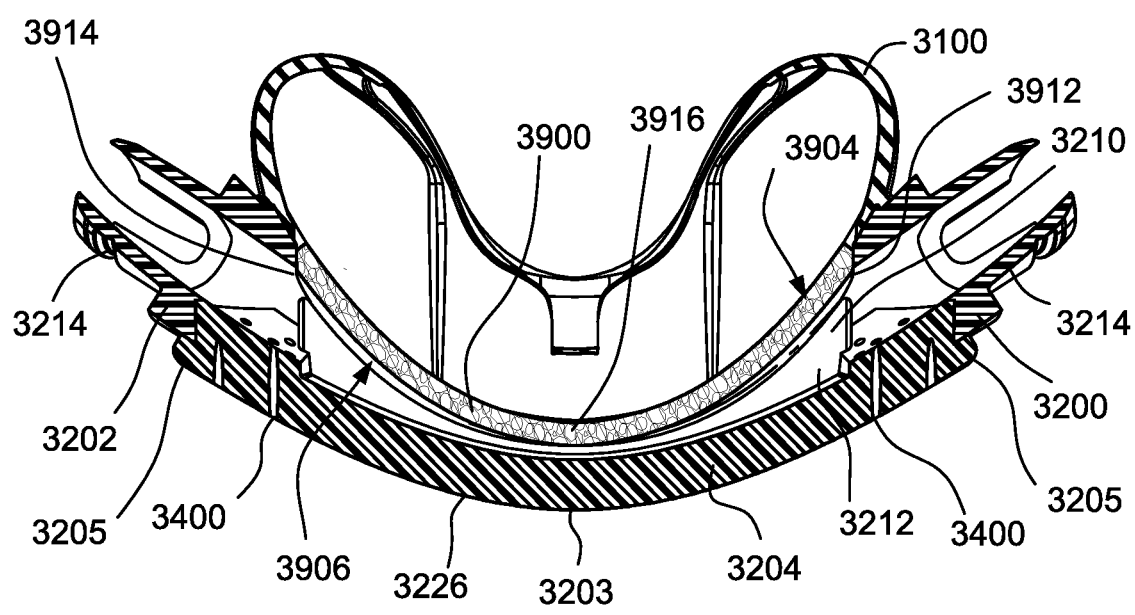

FIG. 22 is a cross-sectional view taken through line 22, 23-22, 23 of FIG. 20 of a seal-forming structure, a plenum chamber, and a heat and moisture exchanger of a patient interface according to an example of the present technology.

Figure 23:
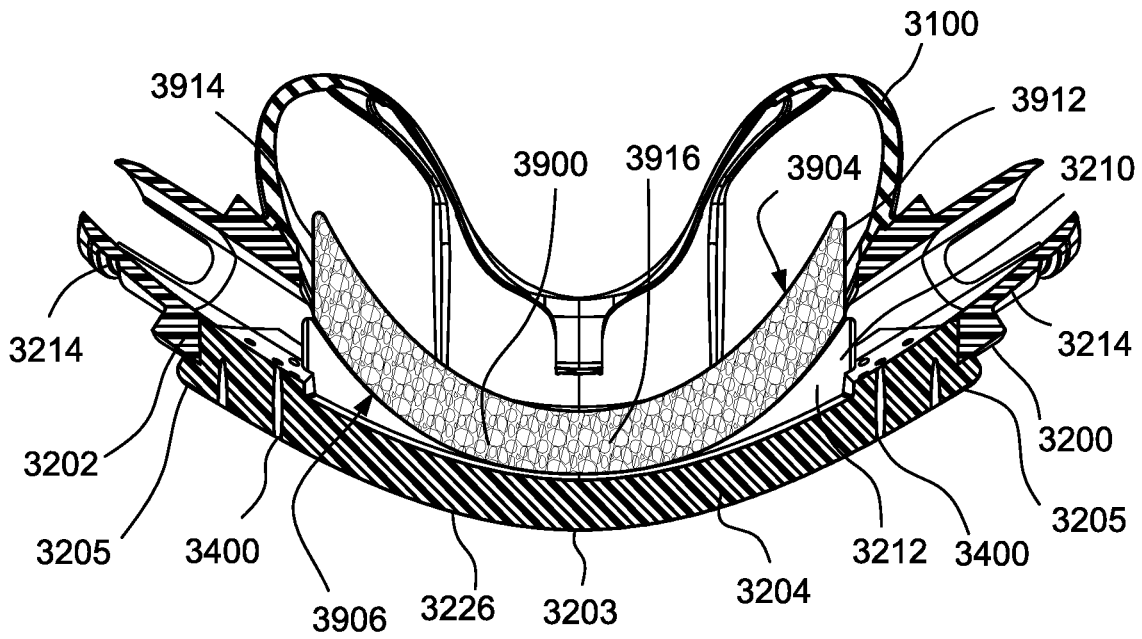

FIG. 23 is a cross-sectional view taken through line 22, 23-22, 23 of FIG. 20 of a seal-forming structure, a plenum chamber, and a heat and moisture exchanger of a patient interface according to an example of the present technology.

Figure 24:
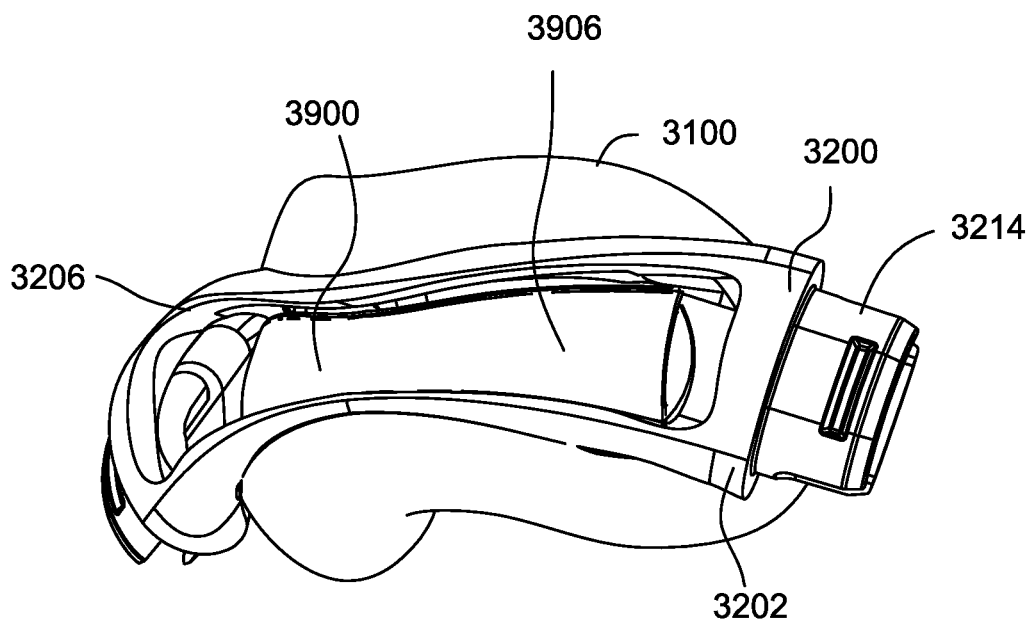

FIG. 24 is an anterior perspective view of a seal-forming structure and a plenum chamber of a patient interface with a removable frame removed according to an example of the present technology.

Figure 25:
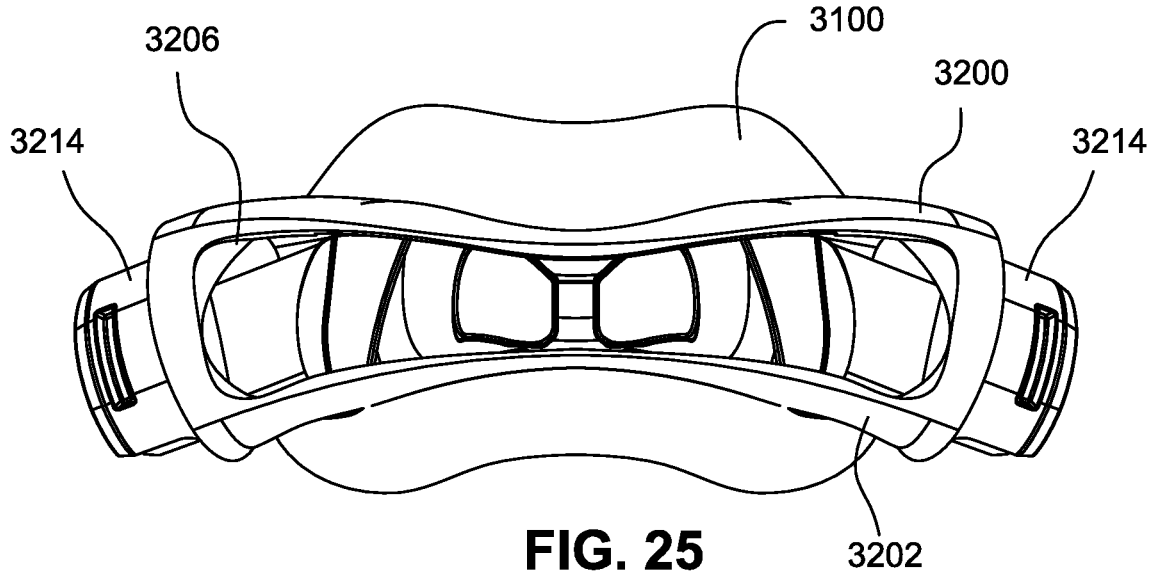

FIG. 25 is an anterior view of a seal-forming structure and a plenum chamber of a patient interface with a removable frame and a heat and moisture exchanger removed according to an example of the present technology.

Figure 26:
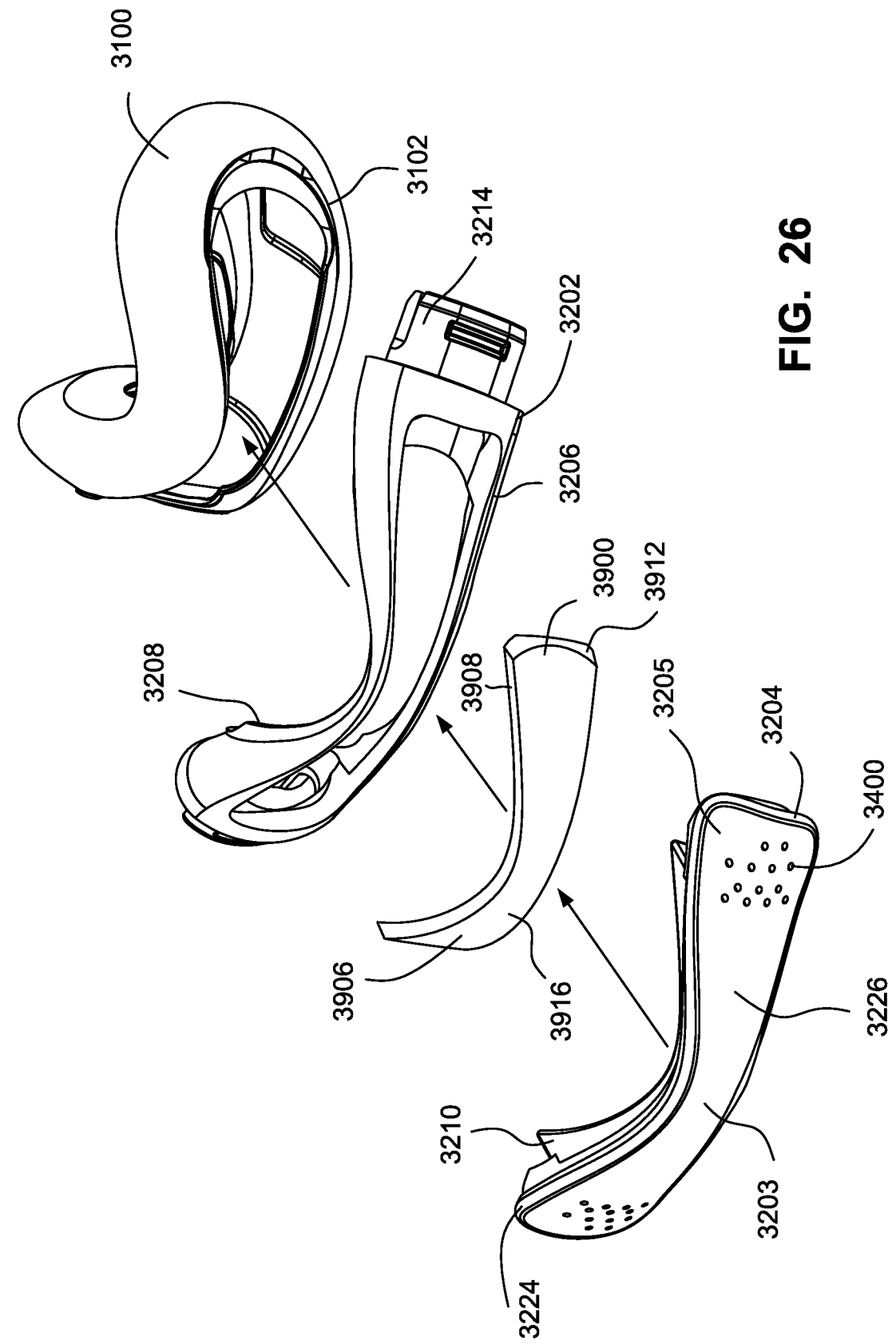

FIG. 26 is an exploded view of a seal-forming structure, a plenum chamber, and a heat and moisture exchanger of a patient interface according to an example of the present technology.

Figure 27:
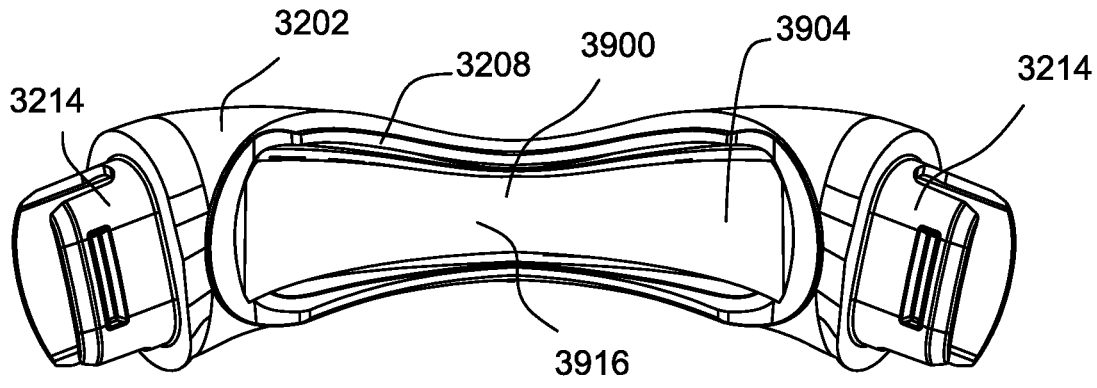

FIG. 27 is a posterior view of a plenum chamber and a heat and moisture exchanger of a patient interface with a seal-forming structure removed according to an example of the present technology.

Figure 28:
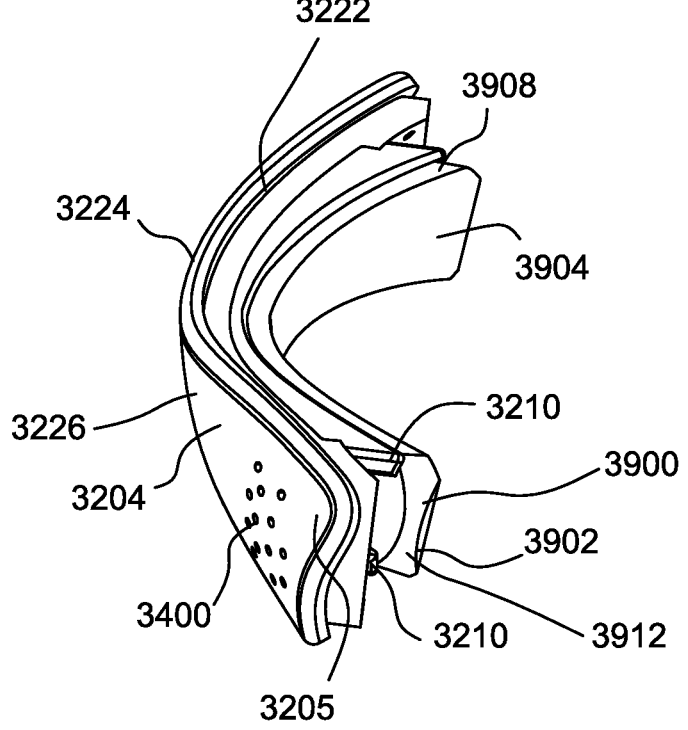

FIG. 28 is a perspective view of a removable frame and a heat and moisture exchanger for a patient interface according to an example of the present technology.

Figure 29:
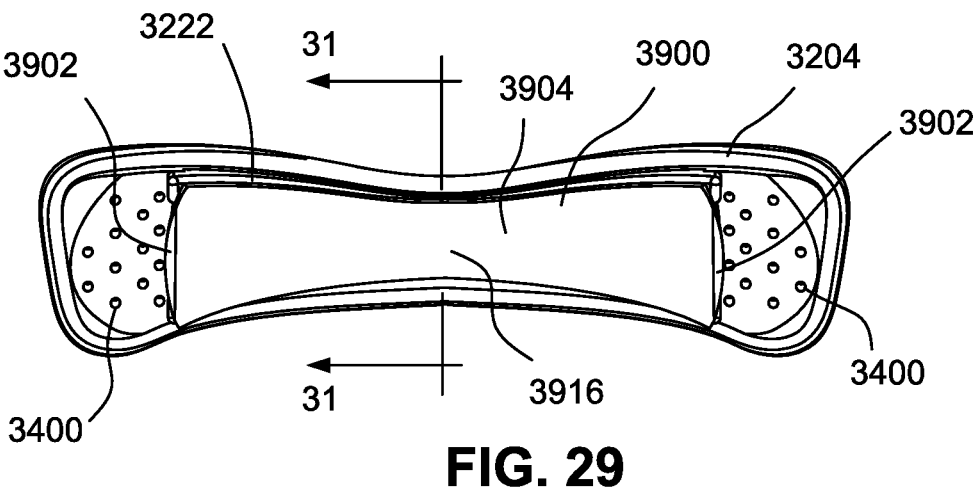

FIG. 29 is a posterior view of a removable frame and a heat and moisture exchanger for a patient interface according to an example of the present technology.

Figure 30:
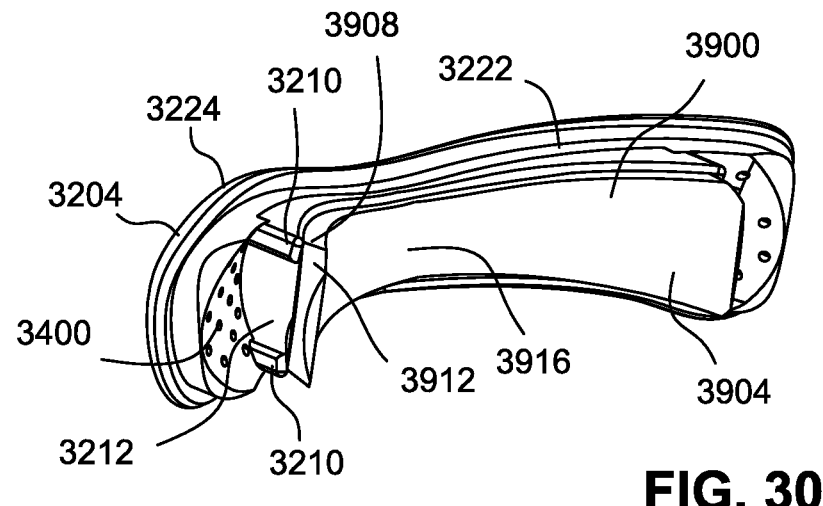

FIG. 30 is another perspective view of a removable frame and a heat and moisture exchanger for a patient interface according to an example of the present technology.

Figure 31:
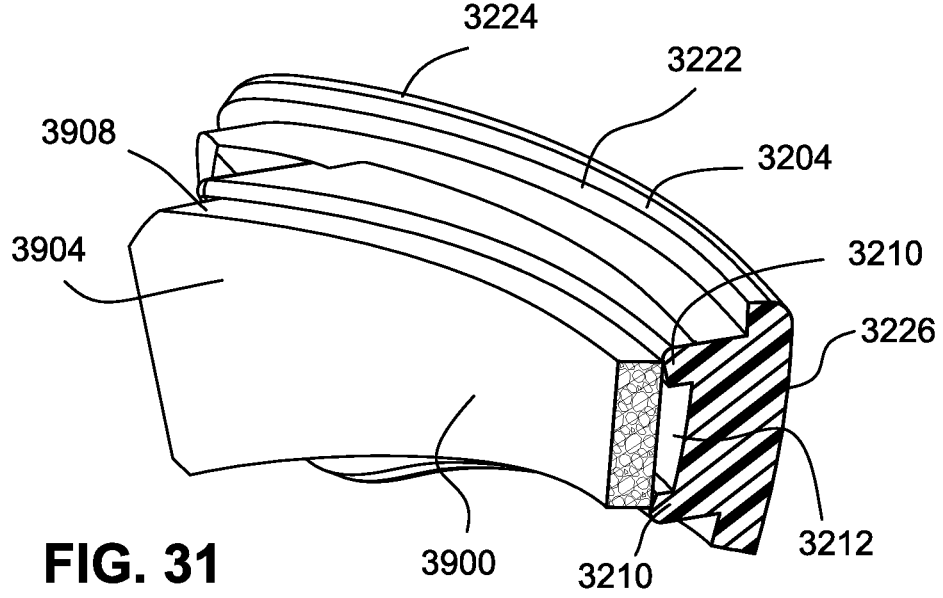

FIG. 31 is a cross-sectional view taken through line 31-31 of FIG. 29 of a removable frame and a heat and moisture exchanger for a patient interface according to an example of the present technology.

Figure 32:
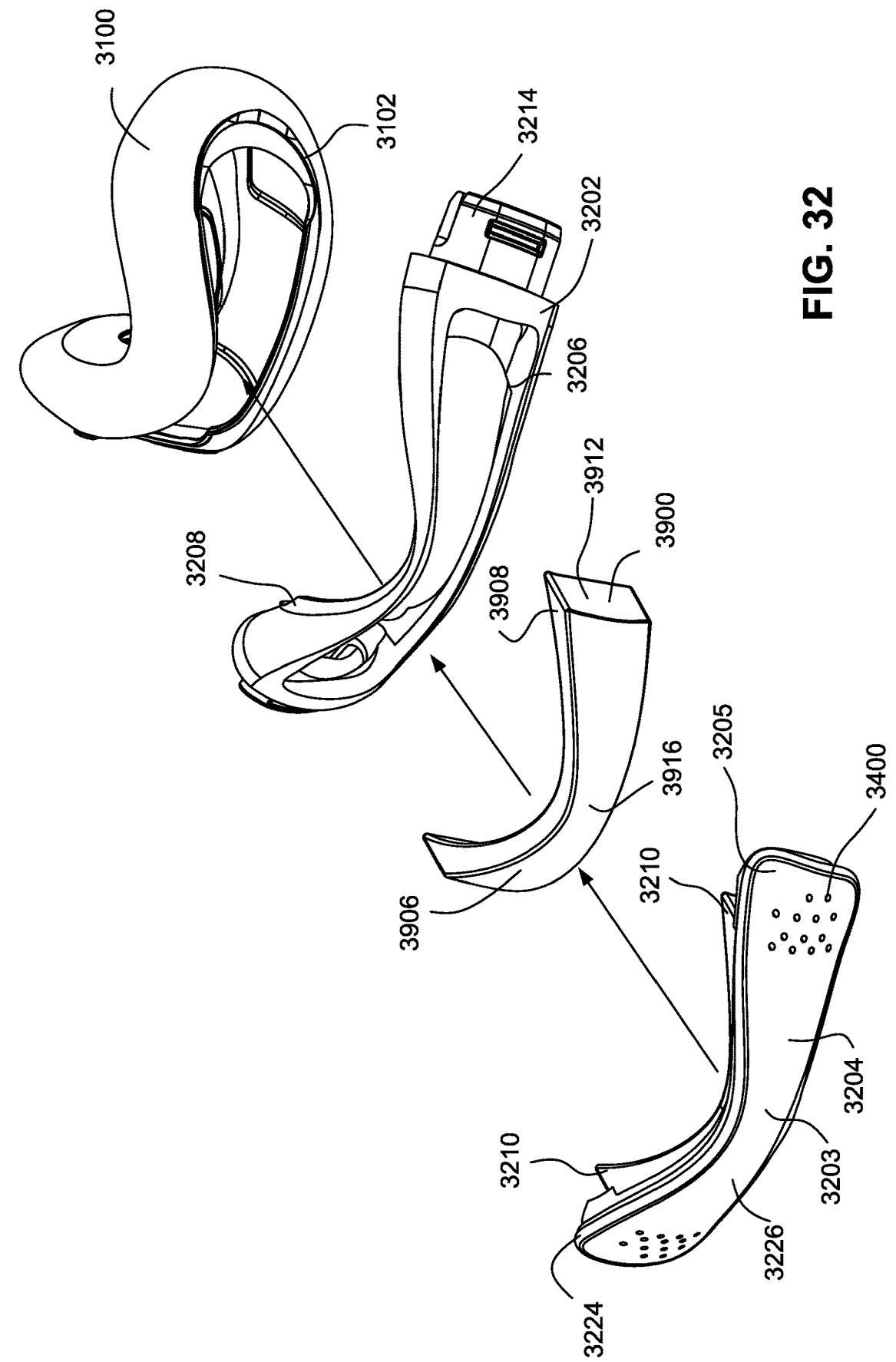

FIG. 32 is an exploded view of a seal-forming structure, a plenum chamber, and a heat and moisture exchanger of a patient interface according to an example of the present technology.

FIG. 33 is a posterior view of a plenum chamber and a heat and moisture exchanger of a patient interface with a seal-forming structure removed according to an example of the present technology.

Figure 34:
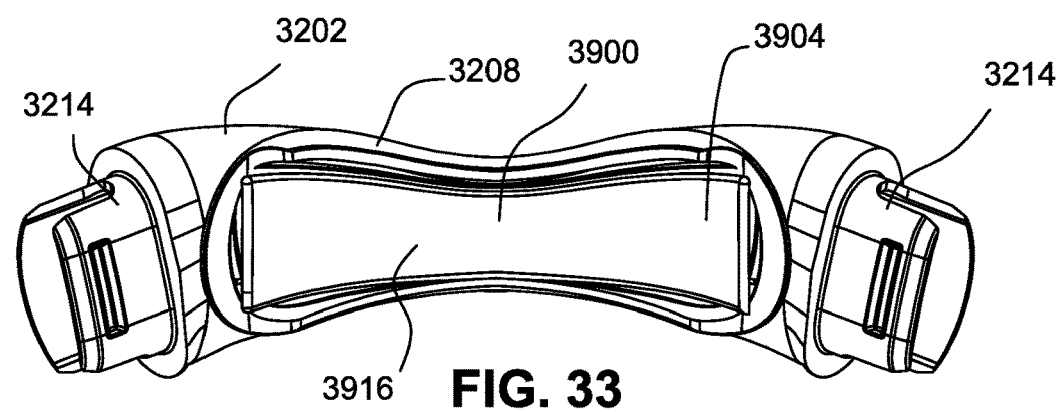

FIG. 34 is a perspective view of a removable frame and a heat and moisture exchanger for a patient interface according to an example of the present technology.

FIG. 35 is another perspective view of a removable frame and a heat and moisture exchanger for a patient interface according to an example of the present technology.

Figure 36:
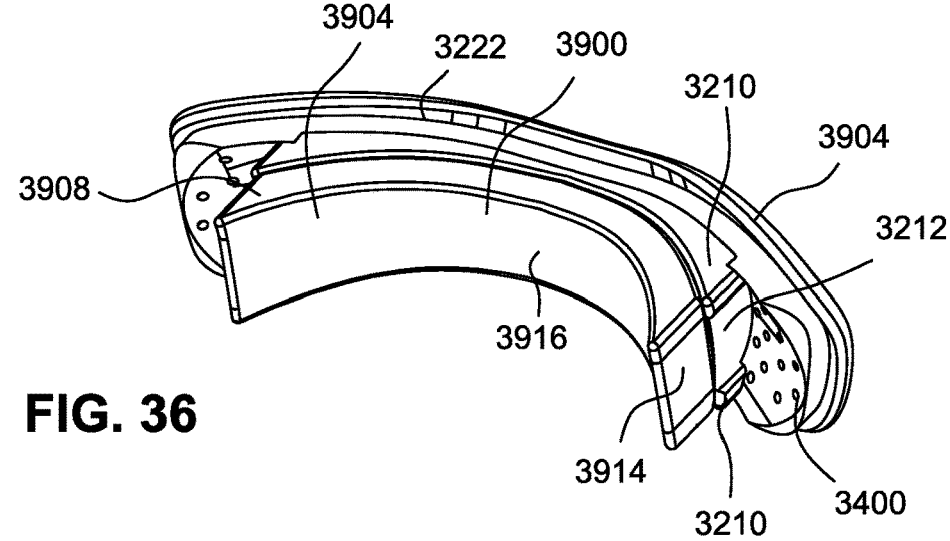

FIG. 36 is another perspective view of a removable frame and a heat and moisture exchanger for a patient interface according to an example of the present technology.

Figure 37:
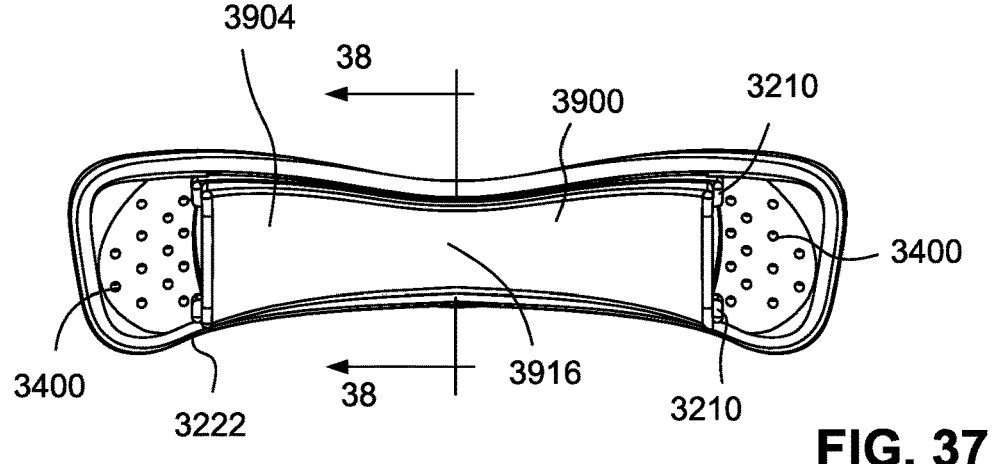

FIG. 37 is a posterior view of a removable frame and a heat and moisture exchanger for a patient interface according to an example of the present technology.

Figure 38:
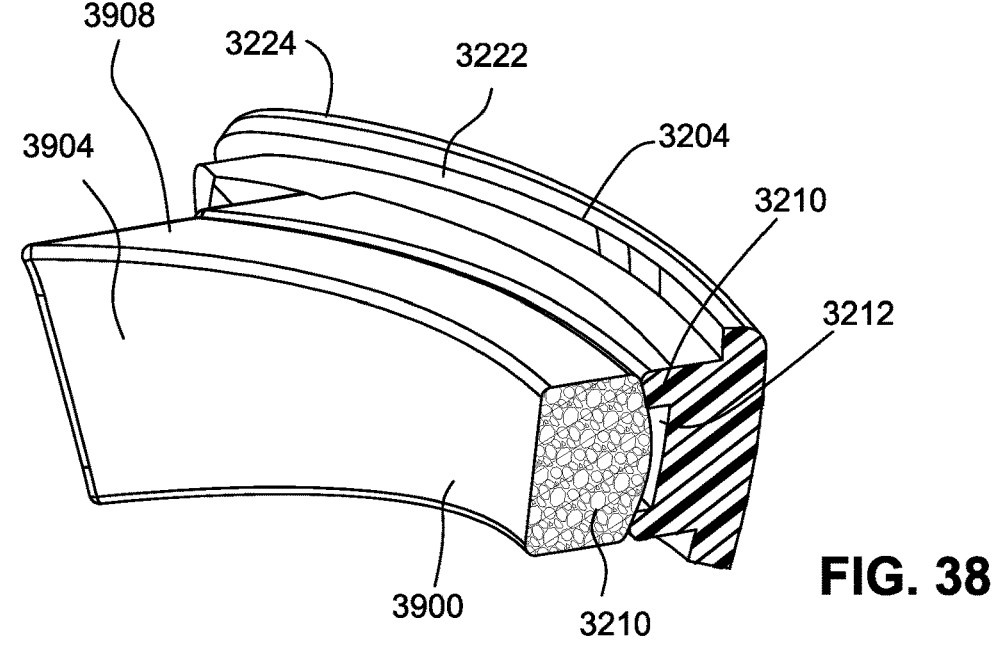

FIG. 38 is a cross-sectional view taken through line 38-38 of FIG. 27 of a removable frame and a heat and moisture exchanger for a patient interface according to an example of the present technology.

FIG. 39 is an anterior perspective view of a removable frame for a patient interface according to an example of the present technology.

FIG. 40 is an anterior view of a removable frame for a patient interface according to an example of the present technology.

FIG. 41 is a posterior perspective view of a removable frame for a patient interface according to an example of the present technology.

FIG. 42 is a posterior view of a removable frame for a patient interface according to an example of the present technology.

Figure 43:
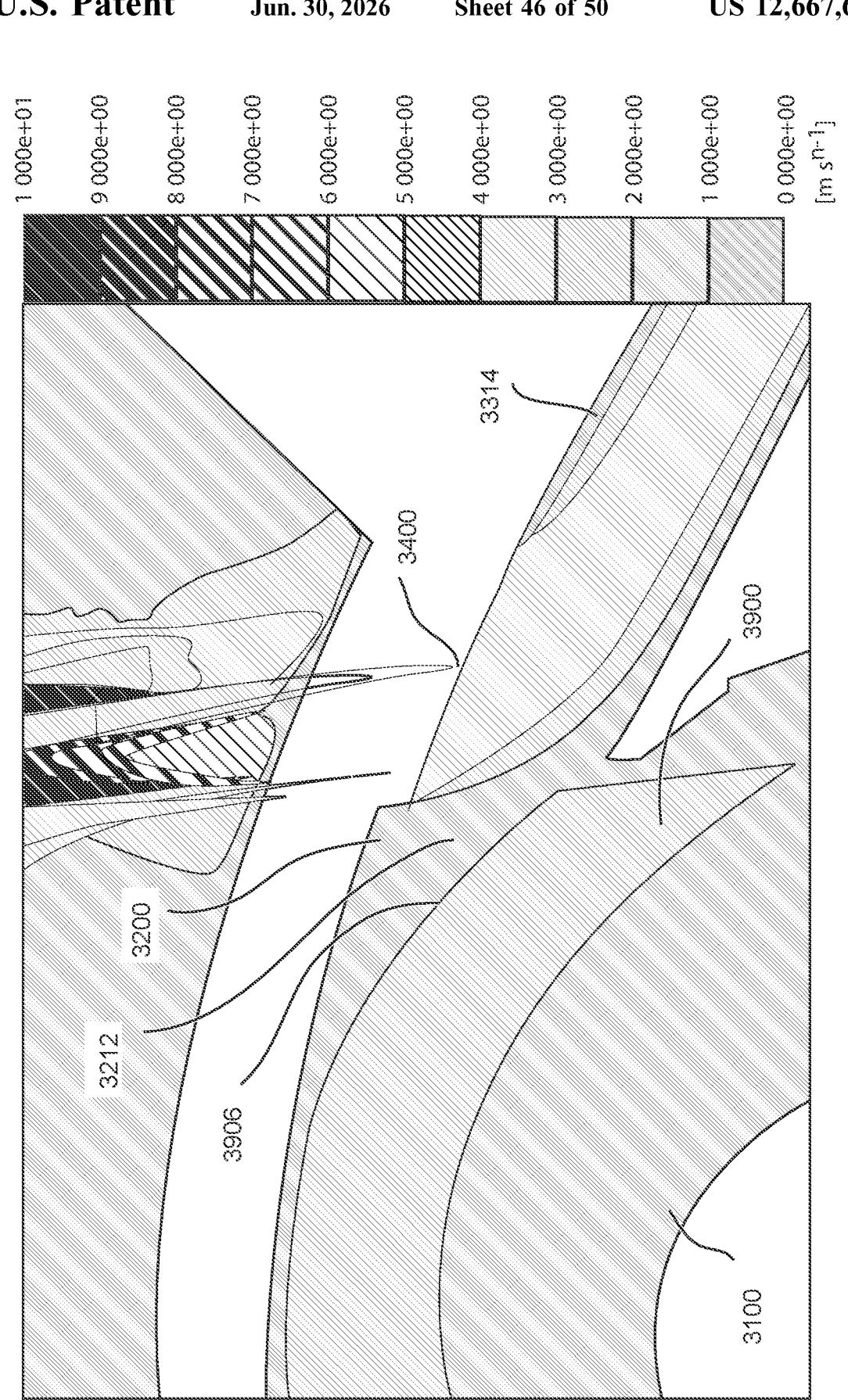

FIG. 43 is a detailed cross-sectional view of a patient interface according to an example of the present technology based on FIG. 22 and showing airflow through the patient interface during breath pause.

Figure 44:
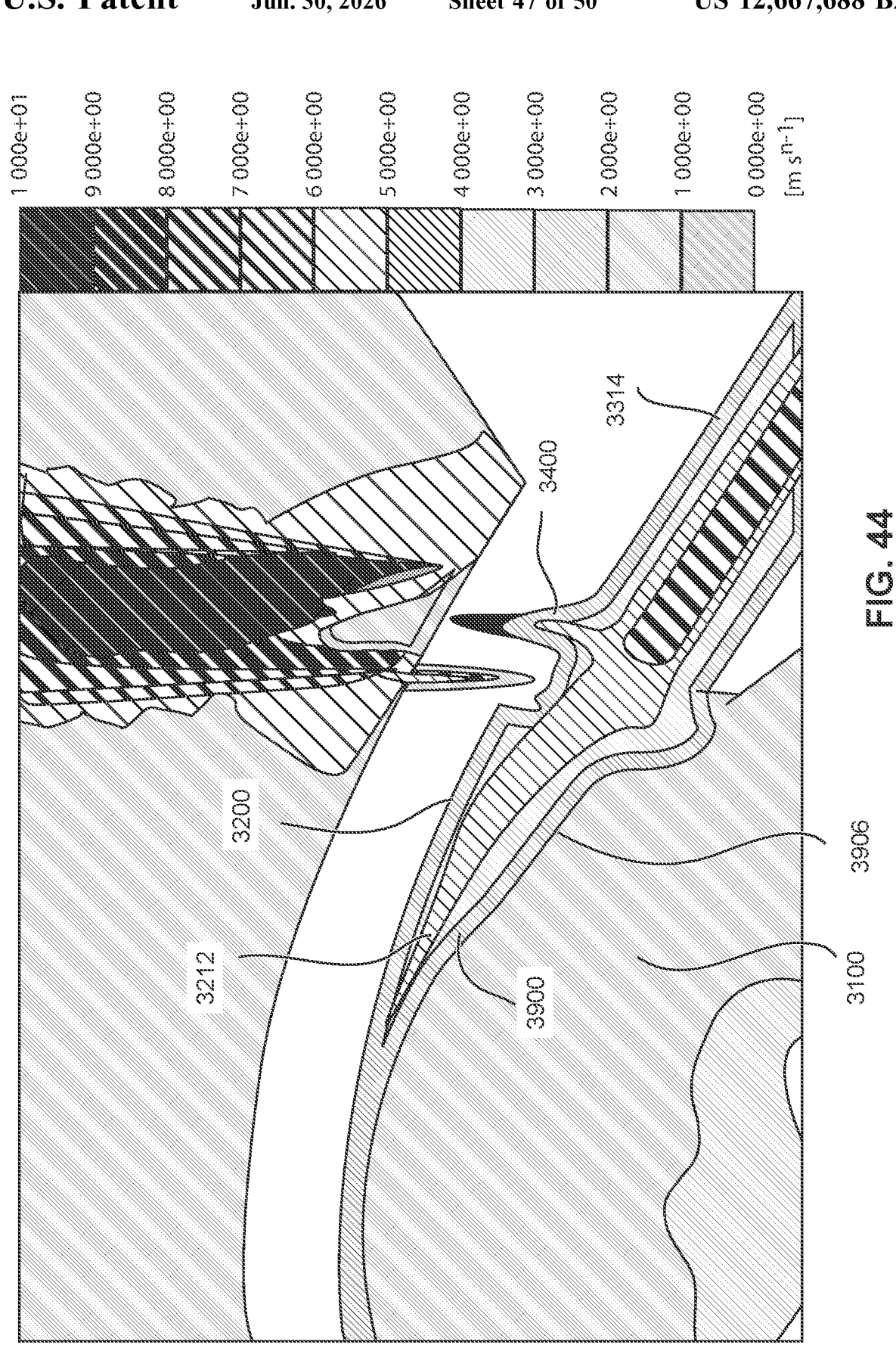

FIG. 44 is a detailed cross-sectional view of a patient interface according to an example of the present technology based on FIG. 22 and showing airflow through the patient interface during inhalation.

Figure 45:
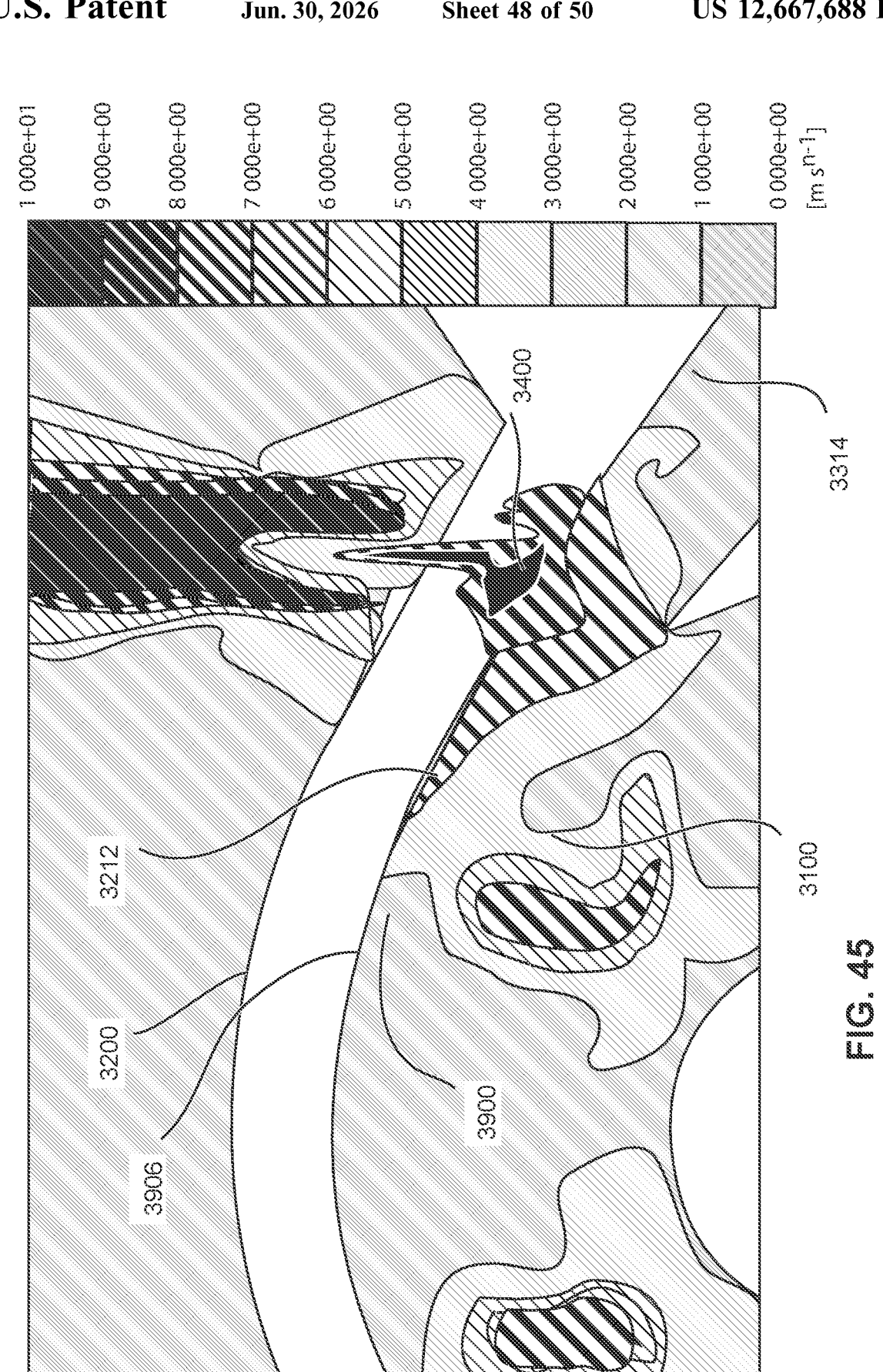

FIG. 45 is a detailed cross-sectional view of a patient interface according to an example of the present technology based on FIG. 22 and showing airflow through the patient interface during breath pause.

4.8 Additional Patient Interface Configurations

Figure 46:
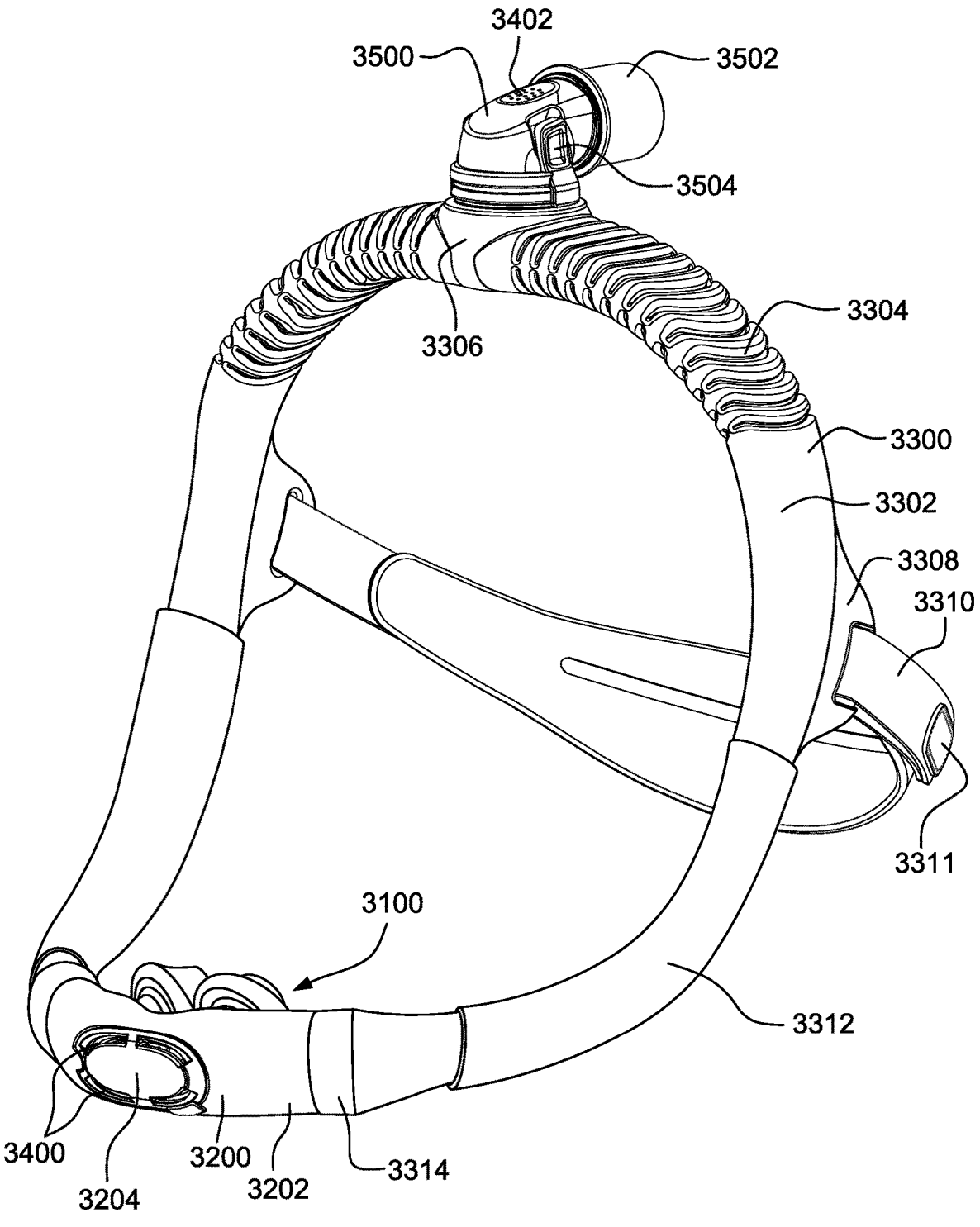

FIG. 46 is an anterolateral view from a superior position of a patient interface according to an example of the present technology.

Figure 47:
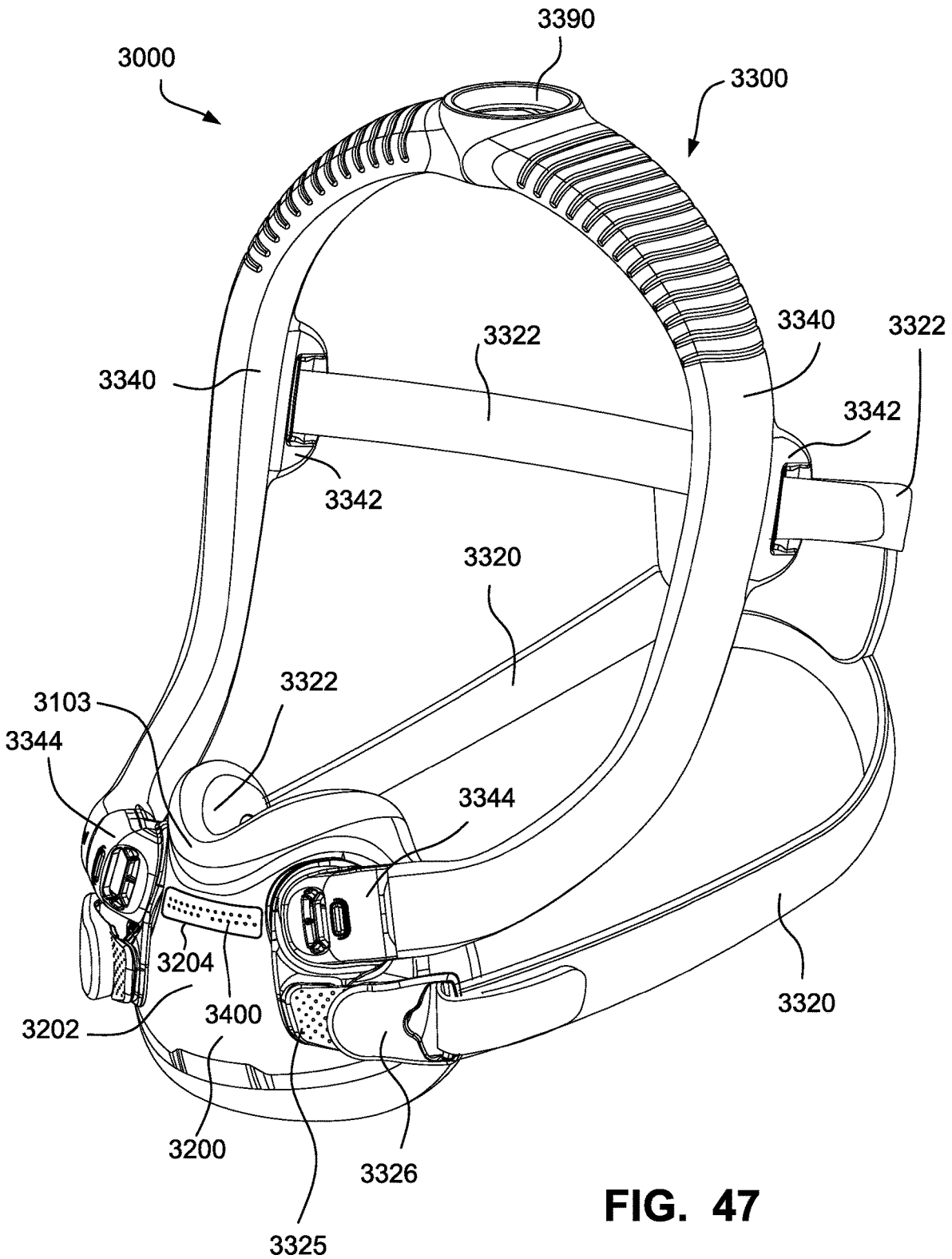

FIG. 47 is a perspective view of a patient interface according to another example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The a respiratory therapy system may comprise an RPT device 4000 for supplying a flow of air to the patient 1000 via an air circuit 4170 and a patient interface 3000 or 3800.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

An unsealed patient interface 3800, in the form of a nasal cannula, includes nasal prongs 3810a, 3810b which can deliver air to respective nares of the patient 1000 via respective orifices in their tips. Such nasal prongs do not generally form a seal with the inner or outer skin surface of the nares. The air to the nasal prongs may be delivered by one or more air supply lumens 3820a, 3820b that are coupled with the nasal cannula 3800. The lumens 3820a, 3820b lead from the nasal cannula 3800 to a respiratory therapy device via an air circuit. The unsealed patient interface 3800 is particularly suitable for delivery of flow therapies, in which the RPT device generates the flow of air at controlled flow rates rather than controlled pressures. The "vent" at the unsealed patient interface 3800, through which excess airflow escapes to ambient, is the passage between the end of the prongs 3810a and 3810b of the cannula 3800 via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Nasal Cradle

FIGS. 7-15 show a seal-forming structure 3100 according to an example of the present technology. The examples of seal-forming structure 3100 may be considered nasal cradle cushions and are intended to provide a flow of pressurised gas to the patient's nares by sealing against at least the underside of the patient's nose. The exemplary seal-forming structures 3100 will engage the patient's face below the bridge of the nose and some examples, depending on the size and shape of the patient's nose, may engage the patient's nose below the pronasale. The exemplary seal-forming structures 3100 will also engage the patient's face at least above the upper vermillion Thus, the exemplary seal-forming structures 3100 may seal against the patient's lip superior in use. Furthermore, the patient's mouth may remain uncovered by the seal-forming structure 3100 of the depicted examples such that the patient may breathe freely, i.e., directly to atmosphere, without interference from the seal-forming structure 3100.

Examples of a nasal cradle cushion, e.g., the exemplary seal-forming structures disclosed herein, may include a superior saddle or concave region that has positive curvature across the cushion. Also, a nasal cradle cushion may be understood to have a single target seal forming region or surface, whereas a pillows cushion may have two target seal forming regions (one for each naris). Cradle cushions may also have a posterior wall that contacts the patient's lip superior and an upper, central, surface contacts the underside of the patient's nose. These two surfaces on the patient's face may form a nasolabial angle between them (see FIG. 2E). A cradle cushion may be shaped to have a nasolabial angle within the range of 90 degrees to 120 degrees.

Furthermore, the exemplary seal-forming structures 3100 may also be shaped and dimensioned such that no portion of the seal-forming structure 3100 enters into the patient's nares during use.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

Each plenum chamber connector 3214 in these examples may include a notch 3216 that is connected to a clip projection of a clip with a snap-fit. Each plenum chamber connector 3214 may be split to form a slot 3220 to allow deformation within the clip during connection. Each clip may be joined to a clip overmold, which is an intermediate component between the end 3314 of the positioning and stabilising structure 3300. Surrounding the ends 3314 of the positioning and stabilising structure 3300 may be a lip that seals with the plenum chamber connector 3214. The lip may surround the entire opening at the end 3314 of the positioning and stabilising structure 3300 to ensure a complete and gas tight seal against the plenum chamber connector 3214 so that the entire flow of pressurised gas passing through the positioning and stabilising structure 3300 reaches the patient via the plenum chamber 3200 and the seal-forming structure 3100. The plenum chamber connector 3214 may also include a chamfered edge 3218 that provides a smooth transition into the end 3314 of the positioning and stabilising structure 3300.

In the examples of FIGS. 7-23, the seal-forming structure 3100 may be constructed from a relatively resilient material, such as an elastomer like silicone as described above, while the plenum chamber 3200 may be constructed from a relatively rigid material, such as polycarbonate. In such an example, the seal-forming structure 3100 may be molded onto the plenum chamber 3200, and this molded connection may be permanent. Alternatively, the seal-forming structure 3100 and the plenum chamber 3200 may be formed separately so as to be removably attachable to one another, e.g., by the patient for cleaning or replacement of the seal-forming structure 3100. In other examples, the seal-forming structure 3100 and the plenum chamber 3200 may each be constructed from a relatively resilient material, such as an elastomer like silicone, and in further examples both components may be molded to form a single, homogeneous piece of the relatively resilient material.

5.3.3 Heat and Moisture Exchanger (HME)

FIGS. 16-23 show examples of a seal-forming structure 3100 and a plenum chamber 3200, as well as a heat and moisture exchanger (HME), according to the present technology. The HME may be in the form of an HME material 3900. The HME material 3900 may be positioned within the plenum chamber 3200 as can be seen in the cross-sectional views.

The plenum chamber 3200 may be a two-part structure that includes a main frame 3202 and a removable frame 3204 that is removable from the main frame 3202. The HME material 3900 may be attached to the removable frame 3204 so that the HME material 3900 can be removed from the plenum chamber 3200 with the removable frame 3204, as will be described further below. FIG. 24 shows the removable frame 3204 removed from the main frame 3202 while the HME material 3900 remains to depict the position of the HME material 3900 within the plenum chamber 3200. FIG. 25 shows the removable frame 3204 and the HME material 3900 removed from the main frame 3202 to depict the interior of the seal-forming structure 3100 and the plenum chamber 3200.

FIGS. 22 and 26-31 show a first variation of the HME material 3900. FIGS. 23 and 32-38 show a second variation of the HME material 3900. The first variation of the HME material 3900 is relatively thinner, i.e., the dimension between an anterior surface 3906 and a posterior surface 3904 of the HME material 3900, than the second variation. The cross-sectional views of FIGS. 22 and 23 show that each variation of the HME material 3900 has a constant thickness, i.e., the dimension between the anterior surface 3906 and the posterior surface 3904, from lateral surface 3912 to lateral surface 3914. However, it should be understood that the thickness dimension can vary at different points along the HME material 3900 between lateral surfaces 3912, 3914 as needed to fit within the plenum chamber 3200.

Additionally, in each variation of the HME material 3900 it can be seen that the height, i.e., the dimension between a superior surface 3908 and an inferior surface 3910, is lowest at the medial or central portion 3916 of the HME material 3900 and increases in each lateral direction towards a respective one of the lateral surfaces 3912, 3914. Likewise, a wall 3226 of the removable frame 3204 can be seen with a height that is lowest at a medial portion 3203 and that increase toward respective lateral portions 3205. Furthermore, the main frame anterior hole 3206, where the removable frame 3204 removably attaches to the main frame 3202, may also be shaped and dimensioned to correspond to the wall 3226 of the removable frame. Also, the HME material 3900 may have a height at various points along its length such that it can fit through the main frame anterior hole 3206 when the removable frame 3204 removably attaches to the main frame 3202. The HME material 3900 may also be a material resilient such that the HME material 3900 can deform, as needed, when inserted into the main frame 3202.

It should be understood that the height dimension of the wall 3226 of the removable frame 3204 and the HME material 3900 can vary at different points between lateral portions 3205 and lateral surfaces 3912, 3914, respectively, as needed to fit within the plenum chamber 3200. For example, the HME material 3900 may have a constant height between lateral surfaces 3912, 3914.

The first variation of the HME material 3900 includes a notched portion 3902 at each lateral side of the posterior surface 3904, while the second variation of the HME material 3900 does not have notched portions 3902. However, it should be understood that the relatively thinner HME material 3900 could have no notched portions 3902 and the relatively thicker HME material 3900 could have notched portions 3902. The notched portions 3902 may be included to provide more clearance for the seal-forming structure 3100 and the plenum chamber 3200 when the HME material 3900 is installed in the plenum chamber 3200. Also, a relatively thinner material, as in the first variation, may provide more clearance from the seal-forming structure 3100 and the patient's face.

FIGS. 39-42 show the removable frame 3204 in isolation. The vents 3400 are shown, which may be formed by two groups of vent holes, each positioned proximal to a corresponding lateral end of the removable frame 3204. The removable frame 3204 may also include supports 3210, and the HME material 3900 may be attached to these supports 3210.

U.S. Publication No. 2016/0175552 A1 discloses positioning an HME within a nasal mask, such as the RESMED® AirFit™ N20, or a full-face mask, such as the RESMED® AirFit™ F20. Due to the configuration of these patient interfaces, there may be adequate space within such patient interfaces for an HME of sufficient size to provide a desired level of performance (i.e., heat and moisture exchange). However, more compact patient interfaces such as nasal cradle masks, like the RESMED® AirFit™ N30i, nasal pillows masks, like the RESMED® AirFit™ P30i or the RESMED® AirFit™ P10, and ultra-compact full-face masks, like the RESMED® AirFit™ F30, may have less volume in the plenum chamber 3200 and as such the size, shape, position, and orientation of the HME may be chosen to provide a desired level of performance (i.e., heat and moisture exchange) in a sufficiently compact form-factor. While the HME material 3900 and associated features are described in the context of a nasal cradle seal-forming structure 3100, it should be understood that the concepts described below may be similarly applicable to nasal pillows patient interfaces and to ultra-compact full-face patient interfaces, e.g., as described below in section 5.3.11. Additionally, while the HME material 3900 and associated features are described in the context of a positioning and stabilising structure 3300 that includes conduits to provide air to the patient's airways, these HME concepts may be similarly applicable to patient interfaces without such conduits and that use a tube connected to the plenum chamber 3200 separately from the positioning and stabilising structure 3300.

For example, it may be advantageous for the HME to be at least one of sized, shaped, positioned, and oriented within the plenum chamber 3200 to avoid contact with the patient's face, e.g., the nose and/or lips, when the patient interface 3000 is worn by the patient. Additionally, while the HME may be constructed and arranged to avoid contact with the patient's face during use, it may be advantageous to include a large enough HME material 3900 to provide a desired level of performance (i.e., heat and moisture exchange). If the HME material 3900 is too small, then it may not be capable of adsorbing a sufficient quantity of moisture and heat from exhaled air to heat and humidify incoming air. It should be understand that in the case of a salted foam, such as examples of the HME material 3900 disclosed herein, the salt content may be more determinative of HME performance, i.e., the ability to adsorb and desorb moisture to and from the air in the plenum chamber 3200, than the size, e.g., volume, of the HME material 3900 itself. Powered humidification, i.e., a water tub that may be heated to vaporize water into the incoming flow of pressurized air after the blower 4142 and before reaching the patient via the air circuit 4170 as described in FIGS. 5A and 5B, may be capable of providing approximately 22 mg/L of water vapor per unit volume of air. The HME material 3900 of the present technology may be configured to provide at least 7 mg/L water vapor per unit volume of air, or at least 14 mg/L of water vapor per unit volume of air, or at least 25 mg/L of water vapor per unit volume of air. At the same time, it may also be advantageous to ensure that a balance is struck with impedance because adding the HME material 3900 to the interior of the plenum chamber 3200 may restrict incoming and outgoing airflow. For example, a large portion of HME material 3900 may increase performance, but may also increase impedance.

The HME material 3900 according to the examples disclosed herein includes a posterior surface 3904, i.e., the surface that faces the patient's face during use, that is concave or shaped so as to be curved positively so that the posterior surface 3904 is spaced away from the patient's face in use, even when the seal-forming structure 3100 is compressed by tension from the positioning and stabilising structure 3300. This shape may provide an increased surface area for the posterior surface 3904 which may enhance performance by providing more surface area to interact with the patient's exhaled air to adsorb moisture and desorb moisture to the incoming flow of air. This shape may also provide additional clearance for the patient's facial features, i.e., nose and/or lips. HME material 3900 constructed from foam or paper may be shaped with this curvature of the posterior surface 3904. The anterior surface 3906 of the HME material 3900 may also be curved negatively, i.e., convex, at a magnitude that allows the HME material 3900 to have a desired thickness, whether constant or varied, as discussed above.

By curving the HME material 3900 as described, the HME material 3900 may follow the general contour of the cradle-type seal-forming structure 3100, e.g., as shown in FIGS. 22 and 23, which may also avoid contact with the seal-forming structure 3100 as well. It should be understood that some degree of contact between the HME material 3900 and the seal-forming structure 3100 may be permissible when the seal-forming structure 3100 is compressed against the patient's face during use, e.g., so long as the HME material 3900 is sufficiently deformable so as not to cause discomfort for the patient and so long as the HME material 3900 is blocked from contacting the patient's skin by the seal-forming structure 3100. Additionally, the thinner HME material 3900 of the first variation shown in FIG. 22 compared with the thicker HME material 3900 of the second variation shown in FIG. 23 shows that the HME material 3900 may extend into the volume bounded by the seal-forming structure 3100, as in the second variation, or it may not, as in the first variation.

The curved shape of the HME material 3900 may be achieved by cutting the HME material 3900 into the curved shape from a bulk quantity of foam (e.g., open cell foam) or paper (e.g., corrugated layers of paper), or by deforming the HME material 3900 into a curved shape and retaining that shape by attaching the HME material 3900 to a relatively rigid structure, such as the removable frame 3204. The removable frame 3204 may be constructed from the same material as the main frame 3202, e.g., when the plenum chamber 3200 is constructed from polycarbonate or a similarly rigid material. Alternatively, the removable frame 3204 may be constructed from a material that is different from that of the main frame 3202, e.g., where the main frame 3202 is constructed in one homogeneous piece of relatively resilient material such as an elastomer like silicone. The removable frame 3204 may be constructed from a material that is sufficiently flexible to permit removable attachment to the main frame 3202, while being sufficiently supportive so as to maintain the shape and position of the HME material 3900 within the plenum chamber 3200.

The HME material 3900 may be attached to the removable frame 3204 at supports 3210 that extend from the wall 3226. The removable frame 3204, including the wall 3226 and the supports 3210, may also have a concave or positively curved shape on the side that faces the patient during use to correspond to and/or impart the desired curvature onto the HME material 3900. The supports 3210 may extend laterally across the removable frame 3204, along the wall 3226, and between lateral portions 3205 such that when the HME material 3900 is attached to the supports 3210 a void 3212 is formed by the wall 3226, the supports 3210, and the anterior surface 3906 of the HME material 3900. The void 3212 may be a passageway for incoming air from the conduits via the plenum chamber connectors 3214 to reach the anterior surface 3906 of the HME material 3900 before traveling to the patient's airways. The void 3212 may also be a passageway for air to exit to ambient via the vents 3400 after passing through the HME material 3900.

The supports 3210 are shown not extending to the full width of the wall 3226 such that the lateral portions 3205 extend beyond the supports 3210 in lateral directions. Also, the supports 3210 are shown being approximately the same width, but each support 3210 may have a different width. There may also be more than two supports 3210, as necessary to support the HME material 3900

When the removable frame 3204 is attached to the HME material 3900, e.g., with an adhesive, these components may be removed from the main frame 3202 and the rest of the patient interface 3000 for replacement of the removable frame 3204 and the HME material 3900 and/or cleaning of the patient interface 3000. If the HME material 3900 has a salt applied to enhance its capacity to adsorb moisture, washing the HME material 3900 may wash away the salt. However, periodic cleaning of the seal-forming structure 3100 that contacts the patient's skin is also recommended. Thus, removing the HME material 3900, e.g., along with the removable frame 3204, may allow for cleaning of the seal-forming structure 3100 without deteriorating performance of the HME material 3900.

Also, the HME material 3900 may be replaced as a single unit with the removable frame 3204 after a prescribed interval because performance of the HME material 3900 may degrade after a period of time and the HME material 3900 may become soiled. Thus, rather than cleaning the HME material 3900, it may be preferable and more cost-effective for the patient to replace it.

The removable frame 3204 may be attached to the main frame 3202 within a main frame anterior hole 3206. The removable frame 3204 may include a inner connecting surface 3222 that contacts the main frame 3202 at the perimeter of the main frame anterior hole 3206. The removable frame 3204 may be removably connected to the main frame 3202 with a friction fit or a snap fit. Close tolerances between the main frame 3202 and the removable frame 3204 may minimize leak between these components. A lip seal, e.g., formed from silicone, may be overmolded to one or more of the removable frame 3204 and the main frame 3202 to seal between these components and minimize leak. The removable frame 3204 may also include an outer grip surface 3224 so that the patient can grasp the removable frame 3204 to install and remove the removable frame 3204 from the main frame 3202. The removable frame 3204 may include clips or pull/push tabs to provide a more positive or user-friendly experience in assembly and removal, e.g., in the form of audible and/or tactile feedback when the components are engaged or disengaged.

An alternative to the curved shape of the HME material 3900 may be a rectangular HME material 3900 that spans the plenum chamber 3200, e.g., from one plenum chamber connector 3214 to the other plenum chamber connector 3214. This straight path is shorter than a curved path spanning the same two points, thereby providing a relatively shorter distance to fit the HME material 3900 and, accordingly, there may be a smaller surface area for heat and moisture exchange, as well as increased risk of contact with the patient's nose and/or mouth, thereby causing comfort issues.

The HME material 3900 may separate the interior of the plenum chamber 3200 from the patient to form the void 3212, and as can be seen in FIGS. 22 and 23 the anterior surface 3906 of the HME material 3900 is positioned so as to be at least partially facing the conduit connectors 3214 to allow incoming airflow to impinge upon the anterior surface

3906 of the HME material 3900. The main frame 3202 of the plenum chamber 3200 may include a main frame posterior hole 3208 into which the HME material 3900 may extend. The HME material 3900 may occupy all or substantially all of the main frame posterior hole 3208 such that all or substantially all of the exhaled air from the patient, which contains heat and moisture, will contact the HME material 3900 at its posterior surface 3904 before passing through the HME material 3900. All or substantially all of the pressurized air entering the plenum chamber 3200 via the plenum chamber connectors 3214 may similarly be forced to pass through the HME material 3900, with the exception of some amount of air that passes through the vents 3400 directly to atmosphere, to take up heat and moisture before passing through the seal-forming structure 3100 for breathing by the patient. There may be no gaps or channels around the HME material 3900 so that the humid/heated air from the patient does not to bypass the HME material 3900 before exiting to ambient via the vents 3400. Alternatively, there may be gaps between the perimeter of the HME material 3900 and the perimeter of the main frame posterior hole 3208 that permit air traveling to and from the patient to bypass the HME material 3900, which may improve washout of carbon dioxide.

Foam may be used for the HME material 3900 and may be relatively easier to deform into the curved shape than a corrugated paper structure, which may be relatively more rigid. The increased flexibility of foam, as compared to a corrugated paper structure, may also perform better at enclosing the spaces around the perimeter of the main frame posterior hole 3208 so that air cannot flow around the HME material 3900. Additionally, an open-cell foam may allow air to flow in any direction through the foam's cells, while a corrugated paper structure may only permit flow through the corrugations.

The location of the vents 3400 may also impact HME performance. There is a risk of incoming airflow, that is relatively dry and cool, taking up moisture and heat from the HME material 3900 and exiting to ambient via the vents 3400 with the heat and moisture instead of being inhaled by the patient. For example, vents 3400 positioned medially may permit such an undesirable effect because air may enter the plenum chamber 3200 from the plenum chamber connectors 3214, then pass over the anterior surface 3906 of the HME material 3900, and then pass through the vents 3400 to ambient. Thus, the heated and humidified air may never reach the patient.

By positioning the vents 3400 at lateral portions 3205 of the wall 3226 of the removable frame 3204 but not at the medial portion 3203, as shown in the depicted examples, the incoming airflow is permitted to have less contact with the anterior surface 3906 of the HME material 3900 before reaching the vents 3400, which in turn mitigates the amount of heat and humidity extracted from the HME material 3900 and taken directly to ambient without reaching the patient's airways. By allowing the incoming flow of air to bypass the HME material 3900, the portion thereof that escapes directly to ambient is less able to receive heat and moisture from the HME material 3900 and take the heat and moisture directly to ambient. Also, by positioning the vents 3400 relatively laterally outward, the vents 3400 may also be proximal to the plenum chamber connectors 3214, which function as the inlet ports for the incoming flow of air. Furthermore, as can be seen in FIGS. 22 and 23 the anterior surface 3906 of the HME material 3900 is positioned so as to be at least partially facing the vents 3400 to allow outgoing airflow passing through the HME material 3900 to reach the vents 3400 and then atmosphere.

While the depicted examples show the vents 3400 on the removable frame 3204 of the plenum chamber 3200, the vents 3400 may be positioned further laterally outward and on the main frame 3202, e.g., proximal to the plenum chamber connectors 3214. Alternatively, the main frame 3202 may include vents 3400 in addition to the removable frame 3204.

FIGS. 43-45 depict the flow of air through the patient interface 3000 according to an example of the present technology during three different stages of breathing, which shows how positioning the vents 3400 laterally outward minimizes airflow over the HME material 3900. The regions with the heaviest hatching show relatively high air velocity. The regions with the lightest hatching show air velocity that is relatively low.

In FIG. 43, which is during breath pause, the lightest hatched regions around the HME material 3900 and in the void 3212 adjacent the HME material 3900 indicate relatively little airflow around the HME material 3900. Thus, moisture lost from the HME material 3900 to directly to ambient may be reduced or minimized During breath pause, a relatively large amount of the incoming airflow from the lateral ends 3314 of the conduits may pass directly to ambient via the vents 3400, as indicated by the regions of higher air velocity at the vents 3400.

FIG. 44 shows the inhalation phase. In this image, a relatively lightly hatched region adjacent the anterior surface 3906 of the HME material 3900 indicates an even distribution of air flow velocity across the anterior surface 3906, which in turn provides consistent desorption of moisture from the HME material 3900 to the incoming flow of air for inhalation by the patient.

FIG. 45 shows the exhalation phase. This image indicates that the location of vents 3400 may maximize the contact area for exhaled air to pass through the HME material 3900 for adsorption of moisture before passing to ambient through the vents 3400.

By positioning the vents 3400 laterally outwards, as compared with vents 3400 positioned medially, testing showed that performance can be improved by a factor of approximately 2. For example, the HME material 3900 was able to provide approximately 6-7 mg/L of water vapor per unit volume of air when the vents 3400 were positioned medially. When the vents 3400 are positioned laterally performance of the HME material 3900 was improved to approximately 14-15 mg/L of water vapor per unit volume of air.

Additionally, by placing the vents 3400 laterally outward as shown in the examples, vent flow remains sufficient despite the increased impedance of the HME material 3900, as compared to a similar patient interface 3000 without the HME material 3900 positioned therein, such that the number of vent holes and/or the vent hole size does not need to be increased.

A patient interface 3000 that includes the HME material 3900 may be included in a system that does not include a humidifier, e.g., as described in section 5.6 below, because the HME material 3900 operates to heat and/or humidify the flow of air directed to the patient.

5.3.4 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

FIGS. 7-15 depict examples of the present technology, including a positioning and stabilising structure 3300. In these examples, the positioning and stabilising structure 3300 includes lateral portions 3302 and superior portions 3304 in the form of conduits that direct a flow pressurised gas from a hub 3306 to ends 3314. The positioning and stabilising structure 3300 may be arranged such that the hub 3306 and the decoupling structure 3500 are positioned superior to the patient's head in use. As described below, the decoupling structure 3500 may be rotatable within the hub 3306 and when the patient is wearing the patient interface 3000, e.g., during therapy, the location of the hub 3306 and the decoupling structure 3500 superior to the patient's head allows the patient to move more freely without becoming entangled with the air circuit 4170.

The positioning and stabilising structure 3300 may be constructed of silicone. For example, the lateral portions 3302, the superior portions 3304, the hub 3306, and the lateral ends 3314 may able constructed or molded from a single piece of silicone.

The superior portions 3304 of the positioning and stabilising structure 3300 have ridges and valleys (or concertina sections) that allow the superior portions 3304 to conform to the shape of the corresponding portion of the patient's head in use. The ridges and valleys of the superior portions 3304 allow the superior portions 3304 to be extended and contracted along the longitudinal axis to accommodate larger or smaller heads. The ridges and valleys of the superior portions 3304 allow the superior portions 3304 to be flexed to different radii of curvature to accommodate patient heads of different shapes and sizes.

The lateral portions 3302 portions of the positioning and stabilising structure 3300 may not be formed with the ridges and valleys of the superior portions 3304. Therefore, the lateral portions 3302 may be less extensible and flexible than the superior portions 3304, which may be advantageous because there is less variability in the shape and size of the lateral sides of a patient's head.

The ends 3314 may connect to respective plenum chamber connectors 3214. As described above, the plenum chamber connectors 3214 receive the flow of pressurised gas from the positioning and stabilising structure 3300, which passes through the plenum chamber 3200, through the seal-forming structure 3100, and on to the patient's airways. As described above, the ends 3314 may include clip overmolds and clips that facilitate connection of the ends 3314 to plenum chamber connectors 3214.

The lateral portions 3302 may also each include a tab 3308 that receives a posterior strap end portion 3311 of a posterior strap 3310. The posterior strap 3310 may be length-adjustable, e.g., with a hook and loop material arrangement whereby one of the posterior strap end portion 3311 and the remainder of the posterior strap 3310 includes hook material on its exterior while the other includes loop material on its exterior. The length adjustability of the posterior strap 3310 allows tension on the lateral portions 3302 to be increased to pull the seal-forming structure 3100 into sealing engagement with the patient's face at a desired amount of pressure (i.e., sufficiently tight to avoid leaks while not so tight as to cause discomfort).

The lateral portions 3302 may also be provided with sleeves 3312 that cushion the patient's face against the lateral portions 3302. The sleeves 3312 may be constructed of a breathable textile material that has a soft feel.

5.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. The plenum chamber vent 3400 may comprise a plurality of holes, as described above. The holes of the plenum chamber vent 3400 may be divided into two groups spaced apart laterally. The axis of the flow path through each of the holes of the plenum chamber vent 3400 may be parallel such that cross-flow is avoided to prevent generation of additional noise. The vent holes may be circular.

The holes of the plenum chamber vent 3400 may decrease in radius from the interior of the plenum chamber 3200 to the exterior. Each vent hole is provided with a draft angle. Each hole has a smaller diameter at its anterior end than at its posterior end. The draft angle means that the holes do not have a small cross section across the entire chassis thickness, which helps to provide effective carbon dioxide wash out at high levels of humidification. Additionally, a larger draft angle may result in a plenum chamber 3200 that is easier to manufacture, especially when the plenum chamber 3200 is formed from an injection moulded plastics material. The draft angle enables relatively thick vent pins to be used in the mould and easier ejection.

The holes of the plenum chamber vent 3400 may be provided in two sets towards the middle of the plenum chamber 3200 and the sets may be symmetrical across the centreline of the plenum chamber 3200. Providing a pattern of multiple vent holes may reduce noise and diffuse the flow concentration.

The holes of the plenum chamber vent 3400 may be placed at an optimum distance away from the centreline of the plenum chamber 3200. Placing the holes of the plenum chamber vent 3400 towards the centreline may advantageously reduce the chance that the vent holes are blocked when the patient is sleeping on their side. However, placing the vent holes too close to the middle of the plenum chamber 3200 may result in excessive weakening of the plenum chamber 3200 at the centre, especially since the cross-section of the plenum chamber 3200 in the depicted examples is smallest at the centre due to the overall shape of the plenum chamber 3200. The location of the holes of the plenum chamber vent 3400 may avoid hole blockage during side sleep while leaving the middle section of the chassis sufficiently strong.

The size of each vent hole and the number of vent holes may be optimised to achieve a balance between noise reduction while achieving the necessary carbon dioxide washout, even at extreme humidification. In the depicted examples, the vent holes of the plenum chamber vent 3400 may not provide the total amount of venting for the system. The decoupling structure 3500 may include a decoupling structure vent 3402. The decoupling structure vent 3402 may include one hole or a plurality of holes through the decoupling structure 3500. The decoupling structure vent 3402 may function to bleed off excess pressure generated by the RPT device 4000 before reaching the patient, while the plenum chamber vent 3400 may function to washout carbon dioxide exhaled by the patient during therapy.

5.3.6 Decoupling Structure(s)

In one form the patient interface 3000 includes at least one decoupling structure, for example, a swivel or a ball and socket.

The hub 3306, described above, is connected to a decoupling structure 3500, which is a rotatable elbow in these examples. The decoupling structure 3500 may be rotatable 360° within the hub 3306 in use. The decoupling structure 3500 may be removable from the hub 3306 by manually depressing buttons 3504 to release catches (not shown) from within the hub 3306.

The decoupling structure 3500 may also include a swivel 3502 that allows for rotatable connection to an air circuit 4170.

The rotatability of the decoupling structure 3500, the decoupling structure 3500 being in the form of an elbow, and the rotatability of the swivel 3502 on the decoupling structure 3500 may all increased the degrees of freedom, which in turn reduce tube drag and torque on the patient interface 3000 caused by the connection to the air circuit 4170.

5.3.7 Connection Port

Connection port 3600 allows for connection to the air circuit 4170.

5.3.8 Forehead Support

In one form, the patient interface 3000 includes a forehead support 3700. In other forms, the patient interface 3000 does not include a forehead support.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.3.11 Patient Interface Configurations

5.3.11.1 Tube-Up, Nasal Pillows Patient Interface

FIG. 46 depicts an example of a tube-up, nasal pillows patient interface. Similar to the example shown in FIGS. 7-15, the tube-up aspect may be understood to describe conduits of the positioning and stabilising structure 3300 that pass along corresponding lateral sides of the patient's head between the corresponding eye and ear to be connected to the air circuit. The nasal pillows aspect may be understood to describe the sealing and face contacting arrangement in which the seal-forming structure 3100 is shaped and dimensioned to contact and seal against the patient's face around the inferior periphery of each of the patient's nares. The seal-forming structure 3100 may leave the mouth uncovered while contacting the ala and the columella, and possibly the patient's upper lip.

The HME features described above in section 5.3.3 may be incorporated into a patient interface 3000 of this configuration.

5.3.11.2 Tube-Up, Ultra-Compact Full-Face Patient Interface

FIG. 47 shows a patient interface 3000 that may be understood to be an ultra-compact full-face arrangement. The sealing arrangement of the seal-forming structure 3100 may be understood to be an ultra-compact full-face or oro-nasal arrangement. Full-face may be understood to mean that the patient's nose and mouth are sealed from atmosphere by the seal-forming structure 3100. Ultra-compact may be understood to mean that the seal-forming structure 3100 does not engage the patient's face above the bridge of the nose or above the pronasale. In an ultra-compact full-face arrangement, at least a portion of the patient's pronasale may remain uncovered. As will be described below, the seal-forming structure 3100 may have an opening that corresponds to the patient's mouth. The seal-forming structure 3100 may have another opening that corresponds to the patient's nose, and that opening may be further divided into separate openings for each naris. Also, this example of patient interface 3000 may not include a forehead support.

The positioning and stabilising structure 3300 in this example comprises a pair of headgear tubes 3340, i.e., conduits. This arrangement may also be understood to be a tube-up system in that the headgear tubes 3340 are in pneumatic communication with the air circuit 4170 above or superior to the patient's head so that the air circuit 4170 avoids overlaying the patient's face during use, which may be bothersome.

The pair of headgear tubes 3340 are connected to each other at their superior ends and are each configured to lie against superior and lateral surfaces of the patient's head in use. Each of the headgear tubes 3340 may be configured to lie between a corresponding eye and ear of the patient in use. The inferior end of each headgear tube 3340 is configured to fluidly connect to the plenum chamber 3200. In this example, the inferior end of each headgear tube 3340 connects to a headgear tube connector 3344, i.e., conduit connector, configured to connect to the shell or main frame 3202 of the plenum chamber 3200. The positioning and stabilising structure 3300 comprises a conduit headgear inlet 3390 at the junction of the two headgear tubes 3340. The conduit headgear inlet 3390 is configured to receive a pressurised flow of gas, for example via an elbow comprising a connection port 3600, and allow the flow of gas into the headgear tubes 3340. The headgear tubes 3340 supply the pressurised flow of gas to the plenum chamber 3200.

The positioning and stabilising structure 3300 may comprise one or more straps in addition to the headgear tubes 3340. In this example the positioning and stabilising structure 3300 comprises a pair of upper straps 3322 and a pair of lower straps 3320. The posterior ends of the upper straps 3322 and lower straps 3320 are joined together. The junction between the upper straps 3322 and lower strap 3320 is configured to lie against a posterior surface of the patient's head in use, providing an anchor for the upper strap 3322 and lower straps 3320. Anterior ends of the upper straps 3322 connect to the headgear tubes 3340. In this example each headgear tube 3340 comprises a tab 3342 having an opening through which a respective upper strap 3322 can be passed through and then looped back and secured onto itself to secure the upper headgear strap 3322 to the headgear tube 3340. The positioning and stabilising structure 3300 also comprises a lower strap clip 3326 provided to the anterior end of each of the lower straps 3320. Each of the lower strap clips 3326 is configured to connect to a lower connection point 3325 on the plenum chamber 3200. In this example, the lower strap clips 3326 are secured magnetically to the lower connection points 3325. In some examples, there is also a mechanical engagement between the lower strap clips 3326 and the lower connection points 3325.

The headgear tube connectors 3344 may be configured to allow the patient to breathe ambient air in the absence of pressure within the plenum chamber 3200. Each headgear tube connector 3344 may comprise an anti-asphyxia valve (AAV). The AAV in each headgear tube connector 3344 may be configured to open in the absence of pressure within the plenum chamber 3200 in order to allow a flow of air between the interior of the plenum chamber 3200 and ambient. Each AAV may be biased into a configuration which blocks the flow of air from the interior of the plenum chamber 3200 into a respective headgear tube 3340 but allows for the exchange of air between the plenum chamber 3200 and ambient. When the headgear tubes 3340 are pressurised, the AAV in each headgear tube connector 3344 may prevent the exchange of air between the interior of the plenum chamber 3200 and ambient but allow for a flow of air from the respective headgear tube 3340 into the plenum chamber 3200 for breathing by the patient.

The plenum chamber 3200 shown in FIG. 47 comprises a vent 3400. In this example, the vent 3400 comprises a plurality of holes. The vent 3400 may be formed on the removable frame 3204. In these examples, the vent 3400 is provided to the main frame 3202. In some examples of the present technology the patient interface 3000 comprises a diffuser configured to diffuse air flowing though the vent

3400. The vent 3400 may be positioned centrally on the main frame 3202 to avoid being covered by the patient's bed or bed clothes during side sleeping.

The HME features described above in section 5.3.3 may be incorporated into a patient interface 3000 of this configuration.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of noncontact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or 3800.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000 or 3800.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal (1 hectopascal=100 Pa=100 N/m$^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.8.4 Anatomy

5.8.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.8.4.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a nonairtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.10 REFERENCE SIGNS LIST | |
|---|---|
| patient | 1000 |
| bed partner | 1100 |
| patient interface | 3000 |
| seal-forming structure | 3100 |
| connecting portion | 3102 |
| plenum chamber | 3200 |
| main frame | 3202 |
| medial portion | 3203 |
| removable frame | 3204 |
| lateral portion | 3205 |
| main frame anterior hole | 3206 |
| main frame posterior hole | 3208 |
| support | 3210 |
| void | 3212 |
| plenum chamber connector | 3214 |
| notch | 3216 |
| chamfered edge | 3218 |
| slot | 3220 |
| inner connecting surface | 3222 |
| outer grip surface | 3224 |
| wall | 3226 |
| inferior point | 3230 |
| chord | 3240 |
| superior point | 3250 |
| positioning and stabilising structure | 3300 |
| lateral portion | 3302 |
| superior portion | 3304 |
| hub | 3306 |
| tab | 3308 |
| posterior strap | 3310 |
| end portion | 3311 |
| sleeve | 3312 |
| lateral end | 3314 |
| lower strap | 3320 |
| upper strap | 3322 |
| connection point | 3325 |
| clip | 3326 |
| headgear tube | 3340 |
| tab | 3342 |
| headgear tube connector | 3344 |
| conduit headgear inlet | 3390 |
| vent | 3400 |
| decoupling structure vent | 3402 |
| decoupling structure | 3500 |
| swivel | 3502 |
| button | 3504 |
| connection port | 3600 |
| forehead support | 3700 |
| cannula | 3800 |
| heat and moisture exchanger (HME) material | 3900 |
| notched portion | 3902 |
| posterior surface | 3904 |
| anterior surface | 3906 |
| superior surface | 3908 |
| inferior surface | 3910 |
| lateral surface | 3912 |
| lateral surface | 3914 |
| medial portion | 3916 |
| RPT device | 4000 |
| external housing | 4010 |
| upper portion | 4012 |
| lower portion | 4014 |
| panel | 4015 |
| chassis | 4016 |
| handle | 4018 |

-continued

| 5.10 REFERENCE SIGNS LIST | |
|---|---|
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| electrical components | 4200 |
| PCBA | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| output device | 4290 |
| display driver | 4292 |
| display | 4294 |
| algorithms | 4300 |
| therapy control module | 4330 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| nasal prongs | 3810a |
| nasal prongs | 3810b |
| air supply lumens | 3820a |
| air supply lumens | 3820b |

The invention claimed is:

1. A patient interface comprising:

a plenum chamber pressurisable to a therapeutic pressure of at least 4 cmH2O above ambient air pressure by a flow of air at the therapeutic pressure for breathing by a patient, the plenum chamber comprising a main frame and a removable frame that is removably connectable to the main frame, the main frame comprising two plenum chamber connectors, and each of the plenum chamber connectors being positioned on a corresponding lateral side of the main frame and configured to receive the flow of air at the therapeutic pressure;

a seal-forming structure connected to the plenum chamber, the seal-forming structure being constructed and arranged to seal with a region of the patient's face at least partly surrounding an entrance to the patient's airways, the seal-forming structure having a sealing flange and a hole in the sealing flange to deliver the flow of air at the therapeutic pressure to at least the patient's nares, and the seal-forming structure being constructed and arranged to maintain the therapeutic pressure in the plenum chamber throughout the patient's respiratory cycle in use;

a positioning and stabilising structure comprising two conduits configured to hold the seal-forming structure in a therapeutically effective position on the patient's head, each of the conduits being configured to be positioned on a corresponding lateral side of the patient's head in use, and each of the conduits being configured to connect to a corresponding one of the two plenum chamber connectors;

a vent structure comprising vent holes configured to allow a continuous flow of gas from an interior of the plenum chamber to ambient while the plenum chamber is pressurized by the flow of air at the therapeutic pressure and during inhalation, exhalation, and breath pause, and the vent holes being sized and shaped to maintain the therapeutic pressure in the plenum chamber in use;

a material configured to adsorb water vapour from gases exhaled by the patient and desorb water vapour into the flow of air at the therapeutic pressure, the material being attached to the removable frame such that the removable frame and the material are removable from the main frame together, and the material being shaped and dimensioned to be positioned within the plenum chamber, when the removable frame is removably connected to the main frame, such that at least a portion of the flow of air at the therapeutic pressure entering the plenum chamber from the two plenum chamber connectors passes through the material before entering the patient's airways, wherein the vent holes are positioned such that, in use, a portion of the flow of air at the therapeutic pressure travels to ambient through the vent holes without passing through the material.

2. The patient interface of claim 1, wherein the material further comprises a salt on a surface of the material.

3. The patient interface of claim 1, wherein the removable frame further comprises the vent holes.

4. The patient interface of claim 3, wherein the material is shaped and dimensioned to be positioned within the plenum chamber, when the removable frame is removably connected to the main frame, so that gas exhaled by the patient must pass through the material before exiting to ambient through the vent holes.

5. The patient interface of claim 3, wherein the vent holes include two groups of vent holes, each of the groups of vent holes being positioned proximal to a corresponding lateral side of the removable frame.

6. The patient interface of claim 3, further comprising two supports extending from the removable frame, the material being attached to the supports such that the material is spaced from the removable frame and a void is at least partly formed by the removable frame, the material, and the supports.

7. The patient interface of claim 6, wherein the two plenum chamber connectors are pneumatically connected to the void to direct the flow of air at the therapeutic pressure to the void.

8. The patient interface of claim 7, wherein the vent holes are pneumatically connected to the void to allow air in the void to pass through the vent holes to ambient.

9. The patient interface of claim 1, wherein the material further comprises a posterior surface that faces the patient's face in use, the posterior surface being positively curved to avoid contact with the patient's face during use.

10. The patient interface of claim 1, wherein the seal-forming structure is configured to leave the patient's mouth uncovered and the seal-forming structure further comprises nasal pillows or a nasal cradle.

11. The patient interface of claim 1, wherein the seal-forming structure is configured to seal around the patient's nose and mouth.

12. The patient interface of claim 1, wherein the material is positioned within the plenum chamber so that any portion of the flow of air at the therapeutic pressure that enters the patient's airways must pass through the material before entering the patient's airways.

13. A respiratory pressure therapy (RPT) system comprising:

the patient interface of claim 1;

a respiratory pressure therapy (RPT) device configured to generate the flow of air at the therapeutic pressure;

an air circuit configured to connect the RPT device and the patient interface to direct the flow of air at the therapeutic pressure from the RPT device to the patient interface, and wherein the RPT system does not include a humidifier.

14. The patient interface of claim 1, wherein the material comprises foam.

15. The patient interface of claim 1, wherein the material comprises paper.

16. The patient interface of claim 1, wherein the removable frame is removably connectable to the main frame with a friction fit or a snap fit.

17. The patient interface of claim 1, wherein the removable frame further comprises a lip seal configured to seal between the removable frame and the main frame when the removable frame is removably connected to the main frame.

18. The patient interface of claim 1, wherein the removable frame further comprises an outer grip surface configured to allow the patient to grasp to remove the removable frame from the main frame or connect the removable frame to the main frame.

19. The patient interface of claim 1, wherein the patient interface is configured to leave the patient's mouth uncovered.

20. The patient interface of claim 1, wherein the seal-forming structure is configured to seal around the patient's nose and mouth, and the patient interface is configured to allow the patient to breath from ambient in the absence of a flow of pressurised air.

21. The patient interface of claim 5, wherein a portion of each of the groups of vent holes is positioned laterally outward of a lateralmost edge of the material.

* * * * *